US011198725B2

(12) United States Patent
Sheridan et al.

(10) Patent No.: US 11,198,725 B2
(45) Date of Patent: Dec. 14, 2021

(54) MONOVALENT ANTI-PROPERDIN ANTIBODIES AND ANTIBODY FRAGMENTS

(71) Applicant: Alexion Pharmaceuticals, Inc., New Haven, CT (US)

(72) Inventors: Douglas L. Sheridan, Branford, CT (US); Paul P. Tamburini, Kensington, CT (US); Taneisha Ann-Tanara Mack, East Hampton, CT (US); Walter C. Voegtli, Killingworth, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 36 days.

(21) Appl. No.: 16/479,335

(22) PCT Filed: Jan. 30, 2018

(86) PCT No.: PCT/US2018/015985
§ 371 (c)(1),
(2) Date: Jul. 19, 2019

(87) PCT Pub. No.: WO2018/140956
PCT Pub. Date: Aug. 2, 2018

(65) Prior Publication Data
US 2019/0352381 A1  Nov. 21, 2019

Related U.S. Application Data

(60) Provisional application No. 62/452,187, filed on Jan. 30, 2017.

(51) Int. Cl.
C07K 16/18 (2006.01)

(52) U.S. Cl.
CPC .......... *C07K 16/18* (2013.01); *C07K 2317/22* (2013.01); *C07K 2317/24* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2006/0093599 A1 | 5/2006 | Gazit-Bornstein et al. | |
| 2007/0071675 A1 | 3/2007 | Wu et al. | |
| 2011/0002931 A1 | 1/2011 | Tamburini | |
| 2011/0008340 A1 | 1/2011 | Bansal | |
| 2012/0252717 A1 | 10/2012 | Besman et al. | |
| 2014/0212427 A1 | 7/2014 | Song | |
| 2014/0235535 A1* | 8/2014 | Erickson | C07K 14/605 514/5.3 |
| 2015/0291686 A1 | 10/2015 | Bansal | |
| 2016/0122419 A1 | 5/2016 | Bansal | |
| 2017/0355756 A1* | 12/2017 | Julien | C12N 15/86 |

FOREIGN PATENT DOCUMENTS

| | | |
|---|---|---|
| WO | WO-01/77342 A1 | 10/2001 |
| WO | WO-2007/056227 A2 | 5/2007 |
| WO | wo 2008068048 * | 7/2008 |
| WO | WO-2010/151526 A1 | 12/2010 |
| WO | WO-2011/112850 A2 | 9/2011 |
| WO | WO-2013/093762 A1 | 6/2013 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Harmsen et al., "Properties, production, and applications of camelid single-domain antibody fragments," Appl Microbiol Biotechnol. 77(1):13-22 (2007).
Stork et al., "Biodistribution of a bispecific single-chain diabody and its half-life extended derivatives," J Biol Chem. 284(38):25612-9 (2009) (9 pages).
International Search Report and Written Opinion for International Application No. PCT/US2018/015985, dated Jun. 11, 2018 (16 pages).
International Preliminary Report on Patentability for International Application No. PCT/US2018/015985, dated Jul. 30, 2019 (9 pages).
Rother et al., "Discovery and development of the complement inhibitor eculizumab for the treatment of paroxysmal nocturnal hemoglobinuria," Nat Biotechnol. 25(11):1256-64 (2007) (10 pages).
Van Roy et al., "The preclinical pharmacology of the high affinity anti-IL-6R Nanobody® ALX-0061 supports its clinical development in rheumatoid arthritis," Arthritis Res Ther. 17:135 (2015) (16 pages).
International Search Report for International Application No. PCT/US2018/041661, dated Sep. 24, 2018 (5 pages).
Written Opinion for International Application No. PCT/US2018/041661, dated Sep. 24, 2018 (8 pages).
Tijink et al., "Improved Tumor Targeting of Anti-Epidermal Growth Factor Receptor Nanobodies Through Albumin Binding: Taking Advantage of Modular Nanobody Technology," Mol Cancer Ther. 7(8):2288-97 (2008).
Pedersen et al., "Recruitment of Properdin by Bi-Specific Nanobodies Activates the Alternative Pathway of Complement," Mol Immunol. 124:200-210 (2020).
Extended European Search Report for European Patent Application No. 18744926.9 dated Jul. 10, 2020 (10 pages).
Office Action for Russian Patent Application No. 2019124873, dated May 14, 2021 (14 pages).

(Continued)

*Primary Examiner* — Adam Weidner
(74) *Attorney, Agent, or Firm* — Clark & Elbing LLP

(57) ABSTRACT

Described herein are isolated monovalent antibodies or antibody fragments thereof that bind human properdin. Such antibodies are useful in methods of treatment for diseases mediated by alternative complement pathway dysregulation.

7 Claims, 12 Drawing Sheets

Specification includes a Sequence Listing.

(56) References Cited

OTHER PUBLICATIONS

Mariuzza et al., "The structural basis of antigen-antibody recognition," Annu Rev Biophys Biophys Chem. 16:139-159 (1987).
Pan et al., "Blocking Neuropilin-1 Function Has an Additive Effect with Anti-VEGF to Inhibit Tumor Growth," Cancer Cell. 11(1):53-67 (2007).
Roitt et al., "Enzymatic digestion of human IgG." Immunologia. Moscow, Mir, 110-111 (2000) (7 pages).
Singer et al., "Section 1.3 Structure of Proteins." Geny I genomy. Moscow, Mir, 1:67-69 (1998) (8 pages).
Office Action for Colombian Patent Application No. NC2019/0007686 dated Jun. 18, 2021 (9 pages, English translation not provided).

\* cited by examiner

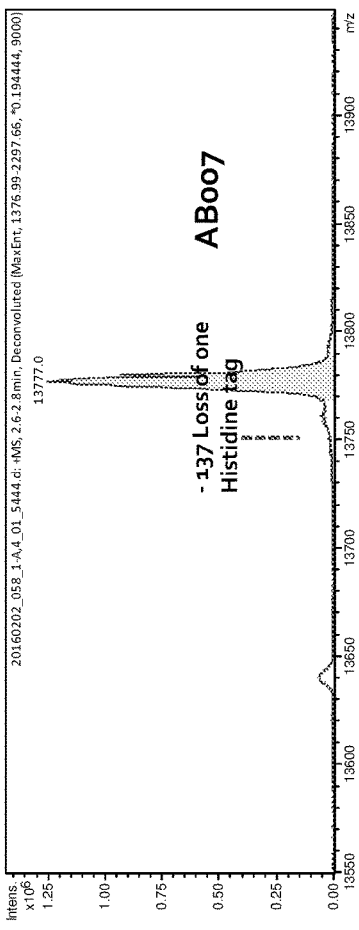
FIG. 5A
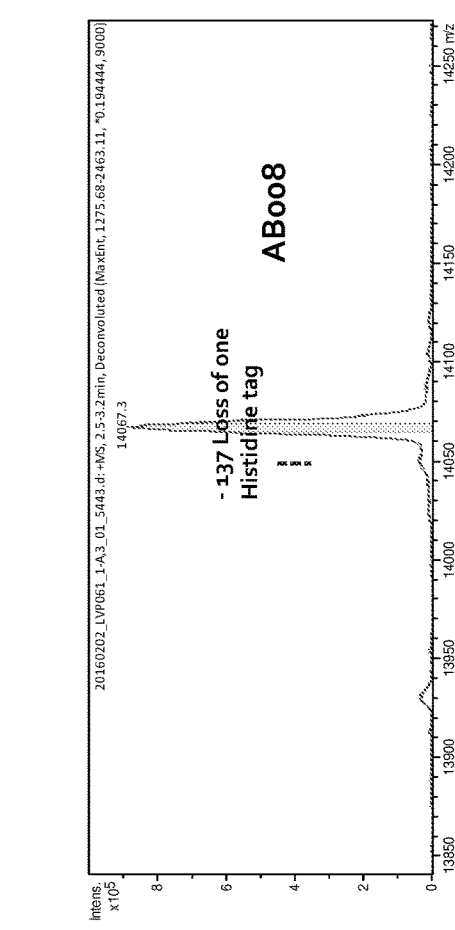
FIG. 5B
| Molecule | Theoretical MW (Da) | Experimental MW (Da) | ppm |
|---|---|---|---|
| AB007 | 13778.3 | 13777.0 | 94.4 |
| AB008 | 14068.6 | 14067.3 | 92.4 |
FIG. 5C

```
                            SEQUENCE LISTING

<160> NUMBER OF SEQ ID NOS: 101

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Gly Gly Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Gly Gly Ser Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Ser Gly Gly Gly
1

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Gly Gly Gly Gly Ser Gly Gly Gly Gly Ser
1               5                  10                  15

<210> SEQ ID NO 5
<211> LENGTH: 14
<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Asp Gly Gly Gly Gly Asp Gly Gly Gly Gly
1               5                  10

<210> SEQ ID NO 6
<211> LENGTH: 14
<212> TYPE: PRT
<213> ORGANISM: Artificial Sequence
<220> FEATURE:
```

<223> OTHER INFORMATION: Synthetic Construct

<400> SEQUENCE: 6

Gly Gly Gly Gly Glu Gly Gly Gly Glu Gly Gly Gly Gly
1               5                   10

<210> SEQ ID NO 7

<400> SEQUENCE: 7

000

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

Leu Cys Gln Pro Cys Arg Ser Pro Arg Trp Ser Leu Trp Ser Thr Trp
1               5                   10                  15

Ala Pro Cys Ser Val Thr Cys Ser Glu Gly Ser Gln Leu Arg Tyr Arg
            20                  25                  30

Arg Cys Val Gly Trp Asn Gly Gln
        35                  40

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Gly Arg Ile Phe Glu Val Asn Met Met Ala
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Ala, Cys, Phe, Gly, His, Ile, Leu, Met,
      Asn, Pro, Gln, Ser, Thr, Val, Trp, or Tyr

<400> SEQUENCE: 10

Arg Val Gly Thr Thr Xaa Tyr Ala Asp Ser Val Lys Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asn, Cys, Gln, His, Met, Ser, Thr, Trp,
      or Tyr

<400> SEQUENCE: 11

Leu Gln Tyr Xaa Arg Tyr Gly Gly Ala Glu Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Arg Val Gly Thr Thr Val Tyr Ala Asp Ser Val Lys Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Leu Gln Tyr Asp Arg Tyr Gly Gly Ala Glu Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Leu Gln Tyr Ser Arg Tyr Gly Gly Ala Glu Tyr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Arg Val Gly Thr Thr Thr Tyr Ala Asp Ser Val Lys Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gly Arg Ile Ser Ser Ile Ile His Met Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Leu Gln Tyr Glu Lys His Gly Gly Ala Asp Tyr

```
1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

```
Gly Tyr Ile Phe Thr Asn Tyr Pro Ile His
1               5                   10
```

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

```
Phe Ile Asp Pro Gly Gly Gly Tyr Asp Glu Pro Asp Glu Arg Phe Arg
1               5                   10                  15

Asp
```

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

```
Arg Gly Gly Gly Tyr Tyr Leu Asp Tyr
1               5
```

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

```
Arg Ala Ser Gln Asp Ile Ser Phe Phe Leu Asn
1               5                   10
```

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

```
Tyr Thr Ser Arg Tyr His Ser
1               5
```

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

```
Gln His Gly Asn Thr Leu Pro Trp Thr
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Gly Phe Ser Leu Thr Thr Tyr Gly Val His
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

Val Ile Trp Ser Gly Gly Asp Thr Asp Tyr Asn Ala Ser Phe Ile Ser
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Asn Lys Asp Tyr Tyr Thr Asn Tyr Asp Phe Thr Met Asp Tyr
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Lys Ser Ser Gln Ser Val Leu Tyr Ser Ser Asn Gln Lys Asn Phe Leu
1               5                   10                  15

Ala

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Trp Ala Ser Thr Arg Glu Ser
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29
```

His Gln Tyr Leu Ser Ser Tyr Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Gly Tyr Thr Phe Ile Asp Tyr Trp Ile Glu
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Glu Ile Phe Pro Gly Ser Gly Thr Ile Asn His Asn Glu Lys Phe Lys
1               5                   10                  15

Asp

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct

<400> SEQUENCE: 32

Glu Gly Leu Asp Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Ser Ala Ser Ser Ser Val Ser Tyr Ile Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Asp Thr Ser Thr Leu Ala Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 35

Gln Gln Trp Ser Arg Asn Pro Phe Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Phe Ser Leu Thr Ser Tyr Gly Val His
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic Construct

<400> SEQUENCE: 37

Val Ile Trp Ser Gly Gly Ser Thr Asp Tyr Asn Ala Ala Phe Ile Ser
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Asn Lys Asp Phe Tyr Ser Asn Tyr Asp Tyr Thr Met Asp Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 39

Gly Tyr Thr Xaa Thr Ala Tyr Gly Ile Asn
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Tyr Ile Tyr Ile Gly Asn Gly Tyr Thr Asp Tyr Asn Glu Lys Phe Lys
1               5                   10                  15

Gly

<210> SEQ ID NO 41
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 41

Ser Gly Trp Asp Glu Asp Tyr Ala Met Asp Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Arg Ala Ser Glu Asn Ile Tyr Ser Tyr Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

His Ala Lys Thr Leu Ala Glu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Gln His His Tyr Gly Pro Pro Pro Thr
1               5

<210> SEQ ID NO 45
<211> LENGTH: 258
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
                20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110
```

```
Trp Gly Gln Gly Thr Leu Val Thr Val Ser Ser Gly Gly Gly Ser
            115                 120                 125

Gly Gly Gly Gly Ser Gly Gly Gly Ser Leu Glu Val Gln Leu Val
        130                 135                 140

Glu Ser Gly Gly Gly Leu Val Gln Ala Gly Ser Leu Arg Leu Ser
145                 150                 155                 160

Cys Ala Ala Ser Gly Arg Ile Ser Ser Ile Ile His Met Ala Trp Tyr
                165                 170                 175

Arg Gln Ala Pro Gly Lys Gln Arg Glu Leu Val Ala Glu Ile Ser Arg
                180                 185                 190

Val Gly Thr Thr Val Tyr Ala Asp Ser Val Lys Gly Arg Phe Thr Ile
            195                 200                 205

Ser Arg Asp Asp Ala Lys Asn Thr Val Thr Leu Gln Met Asn Ser Leu
            210                 215                 220

Lys Pro Glu Asp Thr Ala Val Tyr Tyr Cys Asn Ala Leu Gln Tyr Glu
225                 230                 235                 240

Lys His Gly Gly Ala Asp Tyr Trp Gly Gln Gly Thr Gln Val Thr Val
                245                 250                 255

Ser Ser

<210> SEQ ID NO 46
<211> LENGTH: 257
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Val Gln Leu Leu Glu
        130                 135                 140

Ser Gly Gly Gly Leu Val Gln Pro Gly Gly Ser Leu Arg Leu Ser Cys
145                 150                 155                 160

Ala Ala Ser Gly Arg Ile Ser Ser Ile Ile His Met Ala Trp Phe Arg
                165                 170                 175

Gln Ala Pro Gly Lys Glu Arg Glu Leu Val Ser Glu Ile Ser Arg Val
                180                 185                 190

Gly Thr Thr Val Tyr Ala Asp Ser Val Lys Gly Arg Phe Thr Ile Ser
            195                 200                 205
```

```
Arg Asp Asn Ser Lys Asn Thr Leu Tyr Leu Gln Met Asn Ser Leu Lys
210                 215                 220

Pro Glu Asp Thr Ala Val Tyr Tyr Cys Asn Ala Leu Gln Tyr Glu Lys
225                 230                 235                 240

His Gly Gly Ala Asp Tyr Trp Gly Gln Gly Thr Leu Val Thr Val Ser
                245                 250                 255

Ser

<210> SEQ ID NO 47
<211> LENGTH: 256
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Asp
        115                 120                 125

Gly Gly Gly Gly Asp Gly Gly Gly Glu Val Gln Leu Val Glu Ser
    130                 135                 140

Gly Gly Gly Leu Val Gln Ala Gly Gly Ser Leu Arg Leu Ser Cys Ala
145                 150                 155                 160

Ala Ser Gly Arg Ile Ser Ser Ile Ile His Met Ala Trp Tyr Arg Gln
                165                 170                 175

Ala Pro Gly Lys Gln Arg Glu Leu Val Ala Glu Ile Ser Arg Val Gly
            180                 185                 190

Thr Thr Val Tyr Ala Asp Ser Val Lys Gly Arg Phe Thr Ile Ser Arg
        195                 200                 205

Asp Asp Ala Lys Asn Thr Val Thr Leu Gln Met Asn Ser Leu Lys Pro
210                 215                 220

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Gln Val Thr Val Ser Ser
                245                 250                 255

<210> SEQ ID NO 48
<211> LENGTH: 256
<212> TYPE: PRT
<213> ORGANISM: Artificial Sequence
<220> FEATURE:
<223> OTHER INFORMATION: Synthetic Construct

<400> SEQUENCE: 48
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Glu
        115                 120                 125

Gly Gly Gly Gly Glu Gly Gly Glu Val Gln Leu Val Glu Ser
    130                 135                 140

Gly Gly Gly Leu Val Gln Ala Gly Gly Ser Leu Arg Leu Ser Cys Ala
145                 150                 155                 160

Ala Ser Gly Arg Ile Ser Ser Ile Ile His Met Ala Trp Tyr Arg Gln
            165                 170                 175

Ala Pro Gly Lys Gln Arg Glu Leu Val Ala Glu Ile Ser Arg Val Gly
        180                 185                 190

Thr Thr Val Tyr Ala Asp Ser Val Lys Gly Arg Phe Thr Ile Ser Arg
        195                 200                 205

Asp Asp Ala Lys Asn Thr Val Thr Leu Gln Met Asn Ser Leu Lys Pro
210                 215                 220

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Val Thr Val Ser Ser
            245                 250                 255

<210> SEQ ID NO 49
<211> LENGTH: 257
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

```
Trp Gly Gln Gly Thr Leu Val Thr Val Ser Ser Gly Gly Gly Ser
            115                 120                 125
Gly Gly Gly Gly Ser Gly Gly Gly Ser Glu Val Gln Leu Val Glu
130                 135                 140
Ser Gly Gly Gly Leu Val Gln Pro Gly Gly Ser Leu Arg Leu Ser Cys
145                 150                 155                 160
Ala Ala Ser Gly Arg Ile Ser Ser Ile Ile His Met Ala Trp Val Arg
                165                 170                 175
Gln Ala Pro Gly Lys Gln Arg Glu Leu Val Ser Glu Ile Ser Arg Val
            180                 185                 190
Gly Thr Thr Val Tyr Ala Asp Ser Val Lys Gly Arg Phe Thr Ile Ser
        195                 200                 205
Arg Asp Asn Ser Lys Asn Thr Leu Tyr Leu Gln Met Asn Ser Leu Arg
    210                 215                 220
Ala Glu Asp Thr Ala Val Tyr Tyr Cys Asn Ala Leu Gln Tyr Glu Lys
225                 230                 235                 240
His Gly Gly Ala Asp Tyr Trp Gly Gln Gly Thr Leu Val Thr Val Ser
                245                 250                 255
Ser
```

<210> SEQ ID NO 50
<211> LENGTH: 256
<212> TYPE: PRT
<213> ORGANISM: Artificial Sequence
<220> FEATURE:
<223> OTHER INFORMATION: Synthetic Construct

<400> SEQUENCE: 50

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Arg Pro Val Ser Asn Tyr
            20                  25                  30
Ala Ala Ala Trp Phe Arg Gln Ala Pro Gly Lys Glu Arg Glu Phe Val
        35                  40                  45
Ser Ala Ile Asn Trp Gln Lys Thr Ala Thr Tyr Ala Asp Ser Val Lys
    50                  55                  60
Gly Arg Phe Thr Ile Ser Arg Asp Asn Ala Lys Asn Ser Leu Tyr Leu
65                  70                  75                  80
Gln Met Asn Ser Leu Arg Ala Glu Asp Thr Ala Val Tyr Tyr Cys Ala
                85                  90                  95
Ala Val Phe Arg Val Val Ala Pro Lys Thr Gln Tyr Asp Tyr Asp Tyr
            100                 105                 110
Trp Gly Gln Gly Thr Leu Val Thr Val Ser Ser Gly Gly Gly Gly Asp
        115                 120                 125
Gly Gly Gly Gly Asp Gly Gly Gly Glu Val Gln Leu Leu Glu Ser
    130                 135                 140
Gly Gly Gly Leu Val Gln Pro Gly Gly Ser Leu Arg Leu Ser Cys Ala
145                 150                 155                 160
Ala Ser Gly Arg Ile Ser Ser Ile Ile His Met Ala Trp Phe Arg Gln
                165                 170                 175
Ala Pro Gly Lys Glu Arg Glu Leu Val Ser Glu Ile Ser Arg Val Gly
            180                 185                 190
Thr Thr Val Tyr Ala Asp Ser Val Lys Gly Arg Phe Thr Ile Ser Arg
        195                 200                 205
Asp Asn Ser Lys Asn Thr Leu Tyr Leu Gln Met Asn Ser Leu Lys Pro
```

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Leu Val Thr Val Ser Ser
            245                 250                 255

<210> SEQ ID NO 51
<211> LENGTH: 256
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Glu
        115                 120                 125

Gly Gly Gly Gly Glu Gly Gly Gly Glu Val Gln Leu Leu Glu Ser
130                 135                 140

Gly Gly Gly Leu Val Gln Pro Gly Gly Ser Leu Arg Leu Ser Cys Ala
145                 150                 155                 160

Ala Ser Gly Arg Ile Ser Ser Ile Ile His Met Ala Trp Phe Arg Gln
                165                 170                 175

Ala Pro Gly Lys Glu Arg Glu Leu Val Ser Glu Ile Ser Arg Val Gly
            180                 185                 190

Thr Thr Val Tyr Ala Asp Ser Val Lys Gly Arg Phe Thr Ile Ser Arg
        195                 200                 205

Asp Asn Ser Lys Asn Thr Leu Tyr Leu Gln Met Asn Ser Leu Lys Pro
210                 215                 220

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Leu Val Thr Val Ser Ser
            245                 250                 255

<210> SEQ ID NO 52
<211> LENGTH: 256
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Asp
        115                 120                 125

Gly Gly Gly Gly Asp Gly Gly Gly Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Arg Ile Ser Ser Ile Ile His Met Ala Trp Val Arg Gln
                165                 170                 175

Ala Pro Gly Lys Gln Arg Glu Leu Val Ser Glu Ile Ser Arg Val Gly
            180                 185                 190

Thr Thr Val Tyr Ala Asp Ser Val Lys Gly Arg Phe Thr Ile Ser Arg
        195                 200                 205

Asp Asn Ser Lys Asn Thr Leu Tyr Leu Gln Met Asn Ser Leu Arg Ala
    210                 215                 220

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Leu Val Thr Val Ser Ser
                245                 250                 255

<210> SEQ ID NO 53
<211> LENGTH: 347
<212> TYPE: PRT
<213> ORGANISM: Artificial Sequence
<220> FEATURE:
<223> OTHER INFORMATION: Synthetic Construct

<400> SEQUENCE: 53

Leu Glu Val Gln Leu Val Glu Ser Gly Gly Gly Leu Val Gln Ala Gly
1               5                   10                  15

Gly Ser Leu Arg Leu Ser Cys Ala Ala Ser Gly Arg Ile Ser Ser Ile
            20                  25                  30

Ile His Met Ala Trp Tyr Arg Gln Ala Pro Gly Lys Gln Arg Glu Leu
        35                  40                  45

Val Ala Glu Ile Ser Arg Val Gly Thr Thr Val Tyr Ala Asp Ser Val
    50                  55                  60

Lys Gly Arg Phe Thr Ile Ser Arg Asp Asp Ala Lys Asn Thr Val Thr
65                  70                  75                  80

Leu Gln Met Asn Ser Leu Lys Pro Glu Asp Thr Ala Val Tyr Tyr Cys
                85                  90                  95

Asn Ala Leu Gln Tyr Glu Lys His Gly Gly Ala Asp Tyr Trp Gly Gln
            100                 105                 110

Gly Thr Gln Val Thr Val Ser Ser Arg Lys Cys Cys Val Glu Cys Pro
        115                 120                 125
```

```
Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
                195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 54
<211> LENGTH: 351
<212> TYPE: PRT
<213> ORGANISM: Artificial Sequence
<220> FEATURE:
<223> OTHER INFORMATION: Synthetic Construct

<400> SEQUENCE: 54

Leu Glu Val Gln Leu Val Glu Ser Gly Gly Gly Leu Val Gln Ala Gly
1               5                   10                  15

Gly Ser Leu Arg Leu Ser Cys Ala Ala Ser Gly Arg Ile Ser Ser Ile
            20                  25                  30

Ile His Met Ala Trp Tyr Arg Gln Ala Pro Gly Lys Gln Arg Glu Leu
        35                  40                  45

Val Ala Glu Ile Ser Arg Val Gly Thr Thr Val Tyr Ala Asp Ser Val
    50                  55                  60

Lys Gly Arg Phe Thr Ile Ser Arg Asp Asp Ala Lys Asn Thr Val Thr
65                  70                  75                  80

Leu Gln Met Asn Ser Leu Lys Pro Glu Asp Thr Ala Val Tyr Tyr Cys
                85                  90                  95

Asn Ala Leu Gln Tyr Glu Lys His Gly Gly Ala Asp Tyr Trp Gly Gln
            100                 105                 110

Gly Thr Gln Val Thr Val Ser Ser Pro Lys Ser Cys Asp Lys Thr His
        115                 120                 125

Thr Cys Pro Pro Cys Pro Ala Pro Glu Leu Leu Gly Gly Pro Ser Val
    130                 135                 140
```

```
Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Ala Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 55
<211> LENGTH: 258
<212> TYPE: PRT
<213> ORGANISM: Artificial Sequence
<220> FEATURE:
<223> OTHER INFORMATION: Synthetic Construct

<400> SEQUENCE: 55

Leu Glu Val Gln Leu Val Glu Ser Gly Gly Gly Leu Val Gln Ala Gly
1               5                   10                  15

Gly Ser Leu Arg Leu Ser Cys Ala Ala Ser Gly Arg Ile Ser Ser Ile
            20                  25                  30

Ile His Met Ala Trp Tyr Arg Gln Ala Pro Gly Lys Gln Arg Glu Leu
        35                  40                  45

Val Ala Glu Ile Ser Arg Val Gly Thr Thr Val Tyr Ala Asp Ser Val
    50                  55                  60

Lys Gly Arg Phe Thr Ile Ser Arg Asp Asp Ala Lys Asn Thr Val Thr
65                  70                  75                  80

Leu Gln Met Asn Ser Leu Lys Pro Glu Asp Thr Ala Val Tyr Tyr Cys
                85                  90                  95

Asn Ala Leu Gln Tyr Glu Lys His Gly Gly Ala Asp Tyr Trp Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Glu Val Gln Leu Val Glu Ser Gly Gly
    130                 135                 140

Gly Leu Val Lys Pro Gly Gly Ser Leu Arg Leu Ser Cys Ala Ala Ser
145                 150                 155                 160
```

Gly Arg Pro Val Ser Asn Tyr Ala Ala Trp Phe Arg Gln Ala Pro
                165                 170                 175

Gly Lys Glu Arg Glu Phe Val Ser Ala Ile Asn Trp Gln Lys Thr Ala
            180                 185                 190

Thr Tyr Ala Asp Ser Val Lys Gly Arg Phe Thr Ile Ser Arg Asp Asn
        195                 200                 205

Ala Lys Asn Ser Leu Tyr Leu Gln Met Asn Ser Leu Arg Ala Glu Asp
    210                 215                 220

Thr Ala Val Tyr Tyr Cys Ala Ala Val Phe Arg Val Val Ala Pro Lys
225                 230                 235                 240

Thr Gln Tyr Asp Tyr Asp Tyr Trp Gly Gln Gly Thr Leu Val Thr Val
                245                 250                 255

Ser Ser

<210> SEQ ID NO 56
<211> LENGTH: 214
<212> TYPE: PRT
<213> ORGANISM: Artificial Sequence
<220> FEATURE:
<223> OTHER INFORMATION: Synthetic Construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 448
<212> TYPE: PRT
<213> ORGANISM: Artificial Sequence
<220> FEATURE:
<223> OTHER INFORMATION: Synthetic Construct

<400> SEQUENCE: 57

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Thr Asn Tyr
            20                  25                  30
Pro Ile His Trp Val Arg Gln Ala Pro Gly Gln Gly Leu Glu Trp Met
        35                  40                  45
Gly Phe Ile Asp Pro Gly Gly Tyr Asp Glu Pro Asp Glu Arg Phe
    50                  55                  60
Arg Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Arg Gly Gly Gly Tyr Tyr Leu Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Ala Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
```

```
                    405                 410                 415
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 58
<211> LENGTH: 119
<212> TYPE: PRT
<213> ORGANISM: Artificial Sequence
<220> FEATURE:
<223> OTHER INFORMATION: Synthetic Construct

<400> SEQUENCE: 58

Gln Val Gln Val Val Glu Ser Gly Gly Gly Leu Arg Gln Thr Gly Gly
1               5                   10                  15

Ser Leu Arg Leu Ser Cys Thr Ala Ser Gly Arg Ile Phe Glu Val Asn
            20                  25                  30

Met Met Ala Trp Tyr Arg Gln Ala Pro Gly Lys Gln Arg Glu Leu Val
        35                  40                  45

Ala Glu Ile Ser Arg Val Gly Thr Thr Val Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Asp Arg Tyr Gly Gly Ala Glu Tyr Trp Gly Gln Gly
            100                 105                 110

Thr Gln Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Ala Glu Ser Gly Gly Gly Leu Val Gln Ala Gly Asp
1               5                   10                  15

Ser Leu Lys Leu Ser Cys Thr Ala Ser Gly Arg Ile Phe Glu Val Asn
            20                  25                  30

Met Met Ala Trp Tyr Arg Gln Ala Pro Gly Lys Asp Arg Glu Leu Val
        35                  40                  45

Ala Glu Ile Ser Arg Val Gly Thr Thr Thr Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Ser Arg Tyr Gly Gly Ala Glu Tyr Trp Gly Gln Gly
            100                 105                 110

Thr Gln Val Thr Val Ser Gly
        115

<210> SEQ ID NO 60
<211> LENGTH: 119
```

```
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Ser Ser Ile Ile
            20                  25                  30

His Met Ala Trp Tyr Arg Gln Ala Pro Gly Lys Gln Arg Glu Leu Val
        35                  40                  45

Ala Glu Ile Ser Arg Val Gly Thr Thr Val Tyr Ala Asp Ser Val Lys
    50                  55                  60

Gly Arg Phe Thr Ile Ser Arg Asp Asp Ala Lys Asn Thr Val Thr Leu
65                  70                  75                  80

Gln Met Asn Ser Leu Lys Pro Glu Asp Thr Ala Val Tyr Tyr Cys Asn
                85                  90                  95

Ala Leu Gln Tyr Glu Lys His Gly Gly Ala Asp Tyr Trp Gly Gln Gly
            100                 105                 110

Thr Gln Val Thr Val Ser Gly
        115

<210> SEQ ID NO 61
<211> LENGTH: 119
<212> TYPE: PRT
<213> ORGANISM: Artificial Sequence
<220> FEATURE:
<223> OTHER INFORMATION: Synthetic Construct

<400> SEQUENCE: 61

Gln Val Gln Leu Val Glu Ser Gly Gly Gly Leu Arg Gln Thr Gly Glu
1               5                   10                  15

Ser Leu Arg Leu Ser Cys Thr Ala Ser Gly Arg Ile Phe Glu Val Asn
            20                  25                  30

Met Met Ala Trp Tyr Arg Gln Ala Pro Gly Lys Gln Arg Glu Leu Val
        35                  40                  45

Ala Glu Ile Ser Arg Val Gly Thr Thr Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Asp Arg Tyr Gly Gly Ala Glu Tyr Trp Gly Gln Gly
            100                 105                 110

Thr Gln Val Thr Val Ser Gly
        115

<210> SEQ ID NO 62
<211> LENGTH: 256
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
```

```
                    20                  25                  30
Ala Ala Ala Trp Phe Arg Gln Ala Pro Gly Lys Glu Arg Glu Phe Val
                35                  40                  45

Ser Ala Ile Asn Trp Gln Lys Thr Ala Thr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
                100                 105                 110

Trp Gly Gln Gly Thr Leu Val Thr Val Ser Ser Gly Gly Gly Gly Glu
                115                 120                 125

Gly Gly Gly Gly Glu Gly Gly Glu Val Gln Leu Val Glu Ser
                130                 135                 140

Gly Gly Gly Leu Val Gln Pro Gly Gly Ser Leu Arg Leu Ser Cys Ala
145                 150                 155                 160

Ala Ser Gly Arg Ile Ser Ser Ile Ile His Met Ala Trp Val Arg Gln
                165                 170                 175

Ala Pro Gly Lys Gln Arg Glu Leu Val Ser Glu Ile Ser Arg Val Gly
                180                 185                 190

Thr Thr Val Tyr Ala Asp Ser Val Lys Gly Arg Phe Thr Ile Ser Arg
                195                 200                 205

Asp Asn Ser Lys Asn Thr Leu Tyr Leu Gln Met Asn Ser Leu Arg Ala
210                 215                 220

Glu Asp Thr Ala Val Tyr Tyr Cys Asn Ala Leu Gln Tyr Glu Lys His
225                 230                 235                 240

Gly Gly Ala Asp Tyr Trp Gly Gln Gly Thr Leu Val Thr Val Ser Ser
                245                 250                 255

<210> SEQ ID NO 63
<211> LENGTH: 5
<212> TYPE: PRT
<213> ORGANISM: Artificial Sequence
<220> FEATURE:
<223> OTHER INFORMATION: Synthetic Construct

<400> SEQUENCE: 63

Gly Gly Gly Gly Asp
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct

<400> SEQUENCE: 64

Gly Gly Gly Gly Glu
1               5

<210> SEQ ID NO 65
<211> LENGTH: 40
<212> TYPE: DNA
<213> ORGANISM: Artificial Sequence
<220> FEATURE:
<223> OTHER INFORMATION: Synthetic Construct

<400> SEQUENCE: 65
```
gtcaccgtgt cgagccatca tcaccatcat cactgatgag                                40

<210> SEQ ID NO 66
<211> LENGTH: 45
<212> TYPE: DNA
<213> ORGANISM: Artificial Sequence
<220> FEATURE:
<223> OTHER INFORMATION: Synthetic Construct

<400> SEQUENCE: 66
aattctcatc atttgtcatc atcatcctta tagtcgctcg acacg                          45

<210> SEQ ID NO 67
<211> LENGTH: 36
<212> TYPE: DNA
<213> ORGANISM: Artificial Sequence
<220> FEATURE:
<223> OTHER INFORMATION: Synthetic Construct

<400> SEQUENCE: 67
gtccactccc tcgaggtgca gctggtggag tctggg                                    36

<210> SEQ ID NO 68
<211> LENGTH: 33
<212> TYPE: DNA
<213> ORGANISM: Artificial Sequence
<220> FEATURE:
<223> OTHER INFORMATION: Synthetic Construct

<400> SEQUENCE: 68
gctcgacacg gtgacctggg tcccctggcc cca                                       33

<210> SEQ ID NO 69
<211> LENGTH: 27
<212> TYPE: DNA
<213> ORGANISM: Artificial Sequence
<220> FEATURE:
<223> OTHER INFORMATION: Synthetic Construct

<400> SEQUENCE: 69
cataatagct gacagactaa cagactg                                              27

<210> SEQ ID NO 70
<211> LENGTH: 27
<212> TYPE: DNA
<213> ORGANISM: Artificial Sequence
<220> FEATURE:
<223> OTHER INFORMATION: Synthetic Construct

<400> SEQUENCE: 70
cgaaacaagc gctcatgagc ccgaagt                                              27

<210> SEQ ID NO 71
<211> LENGTH: 122
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Gly Trp Asn Gly Glu Gly Ile Tyr Tyr Ala Asp Ser Val
 50                  55                  60

Lys Gly Arg Phe Thr Ile Ser Arg Asp Asn Ala Lys Asn Thr Gly Tyr
 65                  70                  75                  80

Leu Gln Met Asn Ser Leu Lys Pro Glu Asp Thr Ala Val Tyr Tyr Cys
                 85                  90                  95

Ala Ala Asp Ser Glu Gly Val Val Pro Gly Phe Pro Ile Ala Tyr Trp
            100                 105                 110

Gly Gln Gly Thr Gln Val Thr Val Ser Gly
        115                 120

<210> SEQ ID NO 72
<211> LENGTH: 129
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Leu Asn Ser Tyr
             20                  25                  30

Ala Ile Gly Trp Phe Arg Gln Ala Pro Gly Lys Glu Arg Glu Gly Val
         35                  40                  45

Ser Cys Ile Ser Val Ser Asp Asp Ser Thr Tyr Tyr Thr Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Val Asp Ser Ala Pro Leu Tyr Gly Asp Tyr Val Cys Lys Pro Leu
            100                 105                 110

Glu Asn Glu Tyr Asp Phe Trp Gly Gln Gly Thr Gln Val Thr Val Ser
            115                 120                 125

Gly

<210> SEQ ID NO 73
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: Xaa can be any naturally occurring amino acid

<400> SEQUENCE: 73

Gln Val Gln Leu Val Glu Ser Gly Gly Gly Leu Val Gln Ala Gly Gly
 1               5                  10                  15

Ser Leu Xaa Leu Ser Cys Ala Ala Ser Gly Ser Asp Arg Arg Ile Asn
             20                  25                  30

Gly Met Gly Trp Tyr Arg His Pro Pro Gly Lys Gln Arg Glu Leu Val
         35                  40                  45

Ala Ala Ile Thr Ser Gly Gly Ser Thr Asn Tyr Ala Asp Ser Val Lys
 50                  55                  60

Gly Arg Phe Thr Ile Ser Thr Asn Asn Ala Asn Asn Met Met Tyr Leu
65                  70                  75                  80

Gln Met Asn Ser Leu Lys Pro Glu Asp Thr Ala Val Tyr Tyr Cys Ala
                85                  90                  95

Ile Asp Glu Phe Gly Thr Gly Trp Leu Asp Tyr Cys Gly Gln Gly Thr
            100                 105                 110

Gln Val Thr Val Ser Gly
        115

<210> SEQ ID NO 74
<211> LENGTH: 122
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Pro Phe Ser Ser Tyr
            20                  25                  30

Ala Met Gly Trp Phe Arg Gln Ala Pro Gly Lys Glu Arg Glu Ile Val
        35                  40                  45

Ala Gly Leu Ser Trp Ser Gly Gly Asn Val Tyr Tyr Ala Asp Ser Val
    50                  55                  60

Lys Gly Arg Phe Thr Ile Ser Arg Asp Asn Ala Lys Asn Thr Gly Asp
65                  70                  75                  80

Leu Gln Met Asn Ser Leu Lys Pro Glu Asp Thr Ala Val Tyr Tyr Cys
                85                  90                  95

Ala Ile Gly Pro Lys Leu Thr Thr Gly Pro Thr Ala Tyr Arg Tyr Trp
            100                 105                 110

Gly Gln Gly Thr Gln Val Thr Val Ser Ser
        115                 120

<210> SEQ ID NO 75
<211> LENGTH: 129
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Thr Ser Gly Gly Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Thr Trp Asn Gly Ser Asn Arg Tyr Tyr Ala Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Glu His Ser Thr Arg Tyr Ser Gly Phe Tyr Tyr Tyr Thr Arg
            100                 105                 110

Gly Glu Thr Tyr His Tyr Trp Gly Gln Gly Thr Gln Val Thr Val Ser

```
            115                 120                 125
Gly

<210> SEQ ID NO 76
<211> LENGTH: 129
<212> TYPE: PRT
<213> ORGANISM: Artificial Sequence
<220> FEATURE:
<223> OTHER INFORMATION: Synthetic Construct

<400> SEQUENCE: 76

Gln Val Gln Leu Val Glu Ser Gly Gly Leu Val Gln Ala Gly Gly
1               5                  10                  15

Ser Leu Arg Leu Ser Cys Ala Ala Ser Gly Arg Thr Phe Ser Thr Leu
            20                  25                  30

Gly Met Gly Trp Phe Arg Gln Ala Pro Gly Lys Glu Arg Gln Phe Val
        35                  40                  45

Ala Ala Ile Asn Trp Ser Gly Ser Ser Thr Tyr Tyr Ala Asn Ser Val
    50                  55                  60

Lys Gly Arg Phe Thr Ile Ser Arg Asp Asn Ala Gln Ser Thr Met Tyr
65                  70                  75                  80

Leu Gln Met Asn Ser Leu Lys Pro Glu Asp Thr Ala Val Tyr Tyr Cys
                85                  90                  95

Ala Ala Asp Leu Asp Ser Arg Tyr Ser Ala Tyr Tyr Tyr Tyr Ser Asp
            100                 105                 110

Glu Ser Gln Tyr Asp Tyr Trp Gly Gln Gly Thr Leu Val Thr Val Ser
        115                 120                 125

Gly

<210> SEQ ID NO 77
<211> LENGTH: 129
<212> TYPE: PRT
<213> ORGANISM: Artificial Sequence
<220> FEATURE:
<223> OTHER INFORMATION: Synthetic Construct

<400> SEQUENCE: 77

Gln Val Gln Val Val Glu Ser Gly Gly Gly Leu Val Gln Pro Gly Gly
1               5                  10                  15

Ser Leu Ser Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Thr Trp Asp Gly Ala Asn Ile Tyr Tyr Ala Asp Ser Val
    50                  55                  60

Lys Gly Arg Phe Thr Leu Ser Arg Asp Asn Ala Glu Asn Thr Val Trp
65                  70                  75                  80

Leu Gln Leu Asn Ser Leu Lys Pro Glu Asp Thr Ala Val Tyr Tyr Cys
                85                  90                  95

Ala Ala Ala Glu Ser Gly Arg Tyr Ser Gly Arg Asp Tyr Tyr Ser Ala
            100                 105                 110

Pro Gly Val Tyr Leu Tyr Trp Gly Gln Gly Thr Leu Val Thr Val Ser
        115                 120                 125

Gly

<210> SEQ ID NO 78
<211> LENGTH: 129
```

```
<212> TYPE: PRT
<213> ORGANISM: Artificial Sequence
<220> FEATURE:
<223> OTHER INFORMATION: Synthetic Construct

<400> SEQUENCE: 78

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Asp Ile Asn
            20                  25                  30

Ala Met Gly Trp Tyr Arg Gln Ala Pro Gly Lys Gln Arg Glu Leu Val
        35                  40                  45

Ala Asp Ile Thr Ser Ser Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Thr Cys Ala
                85                  90                  95

Ala Glu Ser Ile Arg Glu Ser Gln Asn Arg His Gln Leu Gly Tyr Met
            100                 105                 110

Gly Pro Leu Tyr Asp Tyr Trp Gly Gln Gly Thr Gln Val Thr Val Ser
        115                 120                 125

Gly

<210> SEQ ID NO 79
<211> LENGTH: 129
<212> TYPE: PRT
<213> ORGANISM: Artificial Sequence
<220> FEATURE:
<223> OTHER INFORMATION: Synthetic Construct

<400> SEQUENCE: 79

Gln Val Gln Leu Ile Glu Ser Gly Gly Gly Leu Val Gln Ala Gly Asp
1               5                   10                  15

Ser Leu Arg Leu Ser Cys Ala Ala Ser Glu Gly Thr Phe Ser Arg Phe
            20                  25                  30

Ala Met Gly Trp Phe Arg Gln Ala Pro Gly Lys Glu Arg Glu Phe Val
        35                  40                  45

Ala Ala Ile Asn Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Glu Thr Thr Thr Arg Tyr Ser Gly Tyr Tyr Tyr Tyr Glu Asp
            100                 105                 110

Asn Lys Ser Tyr Asp Tyr Trp Gly Gln Gly Thr Leu Val Thr Val Ser
        115                 120                 125

Gly

<210> SEQ ID NO 80
<211> LENGTH: 120
<212> TYPE: PRT
<213> ORGANISM: Artificial Sequence
<220> FEATURE:
<223> OTHER INFORMATION: Synthetic Construct

<400> SEQUENCE: 80
```

Gln Val Leu Leu Glu Ser Gly Gly Gly Leu Glu Arg Thr Gly
1               5                   10                  15

Ser Leu Arg Leu Ser Cys Ala Ala Ser Gly Ser Ile Phe Ser Val Asn
            20                  25                  30

Ser Met Thr Trp Tyr Arg Gln Ala Pro Gly Lys Arg Arg Glu Phe Leu
        35                  40                  45

Gly Thr Ile Thr Glu Glu Gly Arg Thr Asn Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Tyr
                85                  90                  95

Ala Asn Leu Ile Ser Ser Glu Asp Arg Thr Phe Gly Val Trp Gly Gln
            100                 105                 110

Gly Thr Gln Val Thr Val Ser Ser
        115                 120

<210> SEQ ID NO 81
<211> LENGTH: 122
<212> TYPE: PRT
<213> ORGANISM: Artificial Sequence
<220> FEATURE:
<223> OTHER INFORMATION: Synthetic Construct

<400> SEQUENCE: 81

Gln Val His Leu Val Glu Ser Gly Gly Gly Leu Val Gln Ala Gly Gly
1               5                   10                  15

Ser Leu Arg Leu Ser Cys Thr Ala Ser Gly Gly Thr Val Gly Asp Tyr
            20                  25                  30

Ala Val Gly Trp Phe Arg Gln Ala Pro Gly Lys Glu Arg Glu Leu Ile
        35                  40                  45

Gly Val Val Ser Arg Leu Gly Ala Arg Thr Gly Tyr Ala Asp Ser Val
    50                  55                  60

Leu Gly Arg Phe Thr Ile Ser Arg Asp Asp Val Lys Asn Thr Val Phe
65                  70                  75                  80

Leu Gln Met Asp Ser Val Lys Pro Glu Asp Thr Ala Val Tyr Tyr Cys
                85                  90                  95

Ala Ala Arg Arg Asp Tyr Ser Phe Glu Val Val Pro Tyr Asp Tyr Trp
            100                 105                 110

Gly Gln Gly Thr Gln Val Thr Val Ser Gly
        115                 120

<210> SEQ ID NO 82
<211> LENGTH: 116
<212> TYPE: PRT
<213> ORGANISM: Artificial Sequence
<220> FEATURE:
<223> OTHER INFORMATION: Synthetic Construct

<400> SEQUENCE: 82

Gln Val Gln Met Val Glu Ser Gly Gly Gly Leu Val Gln Ala Gly Gly
1               5                   10                  15

Ser Leu Arg Leu Ser Cys Ala Ala Ser Gly Leu Thr Asn Arg Ile Arg
            20                  25                  30

Ile Met Gly Trp Tyr Arg Gln Ala Pro Gly Lys Leu Arg Glu Leu Val
        35                  40                  45

Ala Thr Ile Thr Asn Asp Gly Ser Thr His Tyr Ala Asp Ser Val Lys
    50                  55                  60

```
Gly Arg Phe Thr Ile Ser Thr Asp Asn Ala Lys Asn Thr Val Phe Leu
65                  70                  75                  80

Gln Met Asn Ser Leu Lys Pro Glu Asp Thr Ala Val Tyr Ile Cys Asn
                85                  90                  95

Val Gly Glu Asn Trp Gly Pro Ala Tyr Trp Gly Gln Gly Thr Gln Val
            100                 105                 110

Thr Val Ser Gly
        115

<210> SEQ ID NO 83
<211> LENGTH: 128
<212> TYPE: PRT
<213> ORGANISM: Artificial Sequence
<220> FEATURE:
<223> OTHER INFORMATION: Synthetic Construct

<400> SEQUENCE: 83

Gln Val Arg Leu Thr Glu Ser Gly Gly Gly Leu Val Gln Tyr Gly Thr
1               5                   10                  15

Asn Leu Thr Leu Thr Cys Val Ala Ser Gly Leu Ile Ser Thr Arg Asn
            20                  25                  30

Lys Met Gly Trp Phe Arg Arg Ser Gly Gly Gln Arg Glu Phe Val
        35                  40                  45

Ala Ser Ser Thr Val Leu Ser Asp Val Ile Gln Asp Ile Ala
50                  55                  60

Glu Thr Val Lys Gly Arg Phe Ala Val Ala Arg Asn Asp Tyr Lys Asn
65                  70                  75                  80

Ile Leu Tyr Leu Gln Met Thr Ala Val Lys Pro Glu Asp Thr Gly Phe
                85                  90                  95

Tyr Trp Cys Ala Ser Gly Thr Ser Leu Phe Gly Ala Ser Arg Arg Glu
            100                 105                 110

Asp Asp Phe Asn Ala Trp Gly Val Gly Thr Gln Val Thr Val Ser Ala
            115                 120                 125

<210> SEQ ID NO 84
<211> LENGTH: 119
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ala
            20                  25                  30

Asp Met Ser Trp Val Arg Gln Ala Pro Gly Lys Gly Pro Glu Trp Val
        35                  40                  45

Ser Ala Ile Asn Ser Asn Gly Gly Ser Thr Tyr Tyr Ala Ala Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Gln Gly Asn Trp Tyr Thr Glu Glu Tyr His Tyr Trp Gly Gln Gly
            100                 105                 110

Thr Leu Val Thr Val Ser Gly
```

-continued

```
                115

<210> SEQ ID NO 85
<211> LENGTH: 129
<212> TYPE: PRT
<213> ORGANISM: Artificial Sequence
<220> FEATURE:
<223> OTHER INFORMATION: Synthetic Construct

<400> SEQUENCE: 85

Gln Val Arg Leu Val Glu Ser Gly Gly Gly Leu Val Gln Ala Gly Asp
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Ala Pro Gly Lys Glu Arg Glu Phe Val
        35                  40                  45

Ala Ala Thr Thr Trp Arg Asp Thr Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Glu Glu Pro Ser Lys Tyr Ser Gly Arg Asp Tyr Tyr Met Met
            100                 105                 110

Gly Asp Ser Tyr Asp Tyr Trp Gly Gln Gly Thr Gln Val Thr Val Ser
        115                 120                 125

Ser

<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ala
            20                  25                  30

Asp Met Ser Trp Val Arg Gln Ala Pro Gly Lys Gly Pro Glu Trp Val
        35                  40                  45

Ser Ala Ile Asn Ser Asn Gly Gly Ser Thr Tyr Tyr Ala Ala Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Gln Gly Asn Trp Tyr Thr Glu Glu Tyr His Tyr Trp Gly Gln Gly
            100                 105                 110

Thr Gln Val Thr Val Ser Gly
        115

<210> SEQ ID NO 87
<211> LENGTH: 129
<212> TYPE: PRT
<213> ORGANISM: Artificial Sequence
<220> FEATURE:
<223> OTHER INFORMATION: Synthetic Construct
```

<400> SEQUENCE: 87

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Ala Pro Gly Lys Glu Arg Glu Phe Val
        35                  40                  45

Ala Ser Ile Ser Gly Ser Gly Asp Ser Arg Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Thr Asn Ser Pro Lys Pro Glu Asp Thr Ala Val Tyr Tyr Cys
                85                  90                  95

Ala Ala Val Leu Pro Thr Arg Tyr Ser Gly Phe Tyr Tyr Ser Asp
            100                 105                 110

Gly Thr Gln Tyr His Tyr Trp Gly Gln Gly Thr Gln Val Thr Val Ser
            115                 120                 125

Ser

<210> SEQ ID NO 88
<211> LENGTH: 118
<212> TYPE: PRT
<213> ORGANISM: Artificial Sequence
<220> FEATURE:
<223> OTHER INFORMATION: Synthetic Construct

<400> SEQUENCE: 88

Gln Val Asn Leu Val Glu Ser Gly Gly Gly Ser Val Gln Ala Gly Gly
1               5                   10                  15

Ser Leu Arg Leu Ser Cys Ala Ala Ser Glu Asn Ile Asn Val Ile Asn
            20                  25                  30

Asp Met Gly Trp Tyr Arg Gln Ala Pro Gly Lys Gln Arg Glu Leu Val
        35                  40                  45

Ala Val Ile Thr Gly His Asp Asn Ile Asn Tyr Ala Asp Ser Ala Thr
    50                  55                  60

Gly Arg Phe Thr Ile Ser Thr Tyr Thr Trp Asn Thr Glu Asn Leu Gln
65                  70                  75                  80

Met Asn Met Leu Lys Pro Glu Asp Thr Ala Val Tyr Tyr Cys Asn Ala
                85                  90                  95

Asp Ile Thr Tyr Ala Asn Gly Arg Phe Asn Asp Trp Gly Gln Gly Thr
            100                 105                 110

Gln Val Thr Val Ser Ser
            115

<210> SEQ ID NO 89
<211> LENGTH: 129
<212> TYPE: PRT
<213> ORGANISM: Artificial Sequence
<220> FEATURE:
<223> OTHER INFORMATION: Synthetic Construct

<400> SEQUENCE: 89

Gln Val His Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

```
Ala Met Gly Trp Phe Arg Gln Pro Gly Lys Glu Arg Glu Phe Val
            35                  40                  45

Ala Ala Ile Thr Trp Ser Gly Ser Ile Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Glu Thr Ser Lys Tyr Ser Gly Ser Tyr Tyr Met Met
            100                 105                 110

Gly Asp Ser Tyr Asp Tyr Trp Gly Gln Gly Thr Gln Val Thr Val Ser
            115                 120                 125

Gly

<210> SEQ ID NO 90
<211> LENGTH: 130
<212> TYPE: PRT
<213> ORGANISM: Artificial Sequence
<220> FEATURE:
<223> OTHER INFORMATION: Synthetic Construct

<400> SEQUENCE: 90

Gln Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Phe Ser Ser Tyr
             20                  25                  30

Ala Met Gly Trp Phe Arg Gln Ala Pro Gly Lys Glu Arg Glu Phe Val
            35                  40                  45

Ala Ala Val Pro Trp Thr Tyr Gly Ser Lys Tyr Tyr Ala Asp Ser Val
 50                  55                  60

Lys Gly Arg Phe Thr Ile Ser Arg Asp Asp Ala Lys Asn Thr Val Tyr
 65                  70                  75                  80

Leu Gln Met Asn Asn Leu Lys Pro Glu Asp Thr Ala Val Tyr Tyr Cys
                 85                  90                  95

Ala Ala Asp Ser Ser Ala Gly Tyr Tyr Ser Gly Phe Asp Tyr Tyr Ser
            100                 105                 110

Ala Ala Thr Pro Tyr Asp Leu Trp Gly Gln Gly Thr Gln Val Thr Val
            115                 120                 125

Ser Gly
    130

<210> SEQ ID NO 91
<211> LENGTH: 125
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Val Glu Ser Gly Gly Gly Leu Val Gln Pro Gly Gly
  1               5                  10                  15

Ser Leu Arg Leu Ser Cys Ala Ala Ser Gly Ser Asp Tyr Tyr Ala Ile
             20                  25                  30

Gly Trp Phe Arg Gln Ala Pro Gly Lys Glu Arg Glu Gly Val Ser Cys
            35                  40                  45

Met Ser Arg Thr Asp Gly Ser Thr Tyr Tyr Ala Asp Ser Val Lys Asp
 50                  55                  60
```

```
Arg Phe Thr Ile Ser Arg Asp Tyr Ala Lys Asn Thr Val Tyr Leu Gln
 65                  70                  75                  80

Met Asn Ser Leu Lys Pro Glu Asp Thr Ala Val Tyr Tyr Cys Gly Leu
                 85                  90                  95

Asp Arg Ser Tyr Pro Thr Gly Gly Ile Ser Cys Leu Phe Gly Asp Phe
            100                 105                 110

Gly Ser Trp Gly Gln Gly Thr Gln Val Thr Val Ser Gly
        115                 120                 125

<210> SEQ ID NO 92
<211> LENGTH: 124
<212> TYPE: PRT
<213> ORGANISM: Artificial Sequence
<220> FEATURE:
<223> OTHER INFORMATION: Synthetic Construct

<400> SEQUENCE: 92

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
             20                  25                  30

Asn Met Gly Trp Phe Arg Gln His Gly Asn Glu Arg Glu Phe Val
         35                  40                  45

Ala Thr Ile Ser Trp Ser Gly Arg Ser Thr Tyr Tyr Ala Asp Ser Val
     50                  55                  60

Lys Gly Arg Phe Ala Ile Ser Arg Asp Asn Ala Asn Thr Thr Val Tyr
 65                  70                  75                  80

Leu Gln Met Asn Ser Leu Lys Pro Glu Asp Ser Ala Val Tyr Tyr Cys
                 85                  90                  95

Ala Ala Ser Thr Arg Gly Trp Tyr Gly Thr Gln Glu Asp Asp Tyr Asn
            100                 105                 110

Phe Trp Gly Gln Gly Thr Gln Val Thr Val Ser Gly
        115                 120

<210> SEQ ID NO 93
<211> LENGTH: 129
<212> TYPE: PRT
<213> ORGANISM: Artificial Sequence
<220> FEATURE:
<223> OTHER INFORMATION: Synthetic Construct

<400> SEQUENCE: 93

Gln Val Gln Leu Val Glu Ser Gly Gly Gly Leu Val Gln Ala Gly Gly
 1               5                  10                  15

Ser Leu Arg Leu Ser Cys Ala Ala Ser Gly Gly Thr Phe Ser Ser Tyr
             20                  25                  30

Ser Met Gly Trp Phe Arg Gln Ala Pro Gly Lys Glu Arg Glu Phe Val
         35                  40                  45

Ala Ala Ile Thr Trp Asn Gly Val Ser Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Thr Asp Thr Ala Val Tyr Tyr Cys
                 85                  90                  95

Ala Ala Glu Ile Thr Thr Arg Tyr Ser Gly Phe Tyr Tyr Tyr Glu Asp
            100                 105                 110

Asn Lys Ser Tyr Asp Tyr Trp Gly Gln Gly Thr Gln Val Thr Val Ser
        115                 120                 125
```

Ser

<210> SEQ ID NO 94
<211> LENGTH: 127
<212> TYPE: PRT
<213> ORGANISM: Artificial Sequence
<220> FEATURE:
<223> OTHER INFORMATION: Synthetic Construct

<400> SEQUENCE: 94

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Arg Thr Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Asp Ser Tyr Pro Thr Gly Gly Ile Ser Cys Leu Phe Gly
            100                 105                 110

His Phe Gly Ser Trp Gly Gln Gly Thr Gln Val Thr Val Ser Ser
        115                 120                 125
```

<210> SEQ ID NO 95
<211> LENGTH: 129
<212> TYPE: PRT
<213> ORGANISM: Artificial Sequence
<220> FEATURE:
<223> OTHER INFORMATION: Synthetic Construct

<400> SEQUENCE: 95

```
Gln Val Gln Leu Val Glu Ser Gly Gly Gly Leu Val Gln Ala Gly Asp
 1               5                  10                  15

Ser Leu Arg Leu Ser Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Thr Trp Ser Gly Val Ser Thr Tyr Tyr Ala Asp Ser Val
    50                  55                  60

Lys Gly Arg Phe Thr Ile Ser Arg Asp Asn Ala Lys Asn Arg Val Tyr
65                  70                  75                  80

Leu Gln Met Asn Ser Leu Lys Pro Glu Asp Thr Ala Val Tyr Ser Cys
                85                  90                  95

Ala Ala Asp Gly Ser Gly Arg Tyr Ser Gly Met Glu Tyr Tyr Asn Arg
            100                 105                 110

Asp Trp Val Tyr Asp Tyr Trp Gly Gln Gly Thr Gln Val Thr Val Ser
        115                 120                 125

Ser
```

<210> SEQ ID NO 96
<211> LENGTH: 121
<212> TYPE: PRT
<213> ORGANISM: Artificial Sequence
<220> FEATURE:

<223> OTHER INFORMATION: Synthetic Construct

<400> SEQUENCE: 96

```
Gln Val His Met Val Glu Ser Gly Gly Gly Leu Val Gln Ala Gly Gly
1               5                   10                  15

Ser Leu Arg Phe Ser Cys Ala Ala Ser Gly Asn Ile Phe Thr Ile Ser
            20                  25                  30

Thr Leu Asp Trp Tyr Arg Gln Ala Pro Gly Glu Gln Arg Glu Leu Val
        35                  40                  45

Ala Thr Leu Thr Pro Asp Gly Ile Thr Asp Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Trp Arg Tyr Ser Asp Asp Tyr Arg Gly Arg Val Asp Tyr Trp Gly
            100                 105                 110

Gln Gly Thr Gln Val Thr Val Ser Gly
        115                 120
```

<210> SEQ ID NO 97
<211> LENGTH: 126
<212> TYPE: PRT
<213> ORGANISM: Artificial Sequence
<220> FEATURE:
<223> OTHER INFORMATION: Synthetic Construct

<400> SEQUENCE: 97

```
Gln Val Gln Leu Ile Glu Ser Gly Gly Gly Leu Val Gln Glu Gly Ala
1               5                   10                  15

Ser Leu Arg Leu Ser Cys Ala Gly Ser Gly Pro Met Phe Ser Arg Leu
            20                  25                  30

Ala Val Gly Trp Phe Arg Gln Ala Pro Gly Lys Glu Arg Glu Phe Val
        35                  40                  45

Ala Val Ile Asn Trp Ser Gly Ser Ala Asp Phe Tyr Thr Asn Ser Val
    50                  55                  60

Lys Gly Arg Phe Thr Ile Ser Arg Asp Asn Ala Lys Asn Thr Val Tyr
65                  70                  75                  80

Leu Glu Met Asn Thr Leu Lys Pro Glu Asp Ser Ala Val Tyr Tyr Cys
                85                  90                  95

Ala Ala Asp Gln Asn Pro Leu Thr Leu Arg Thr Gly Val Arg Asp Val
            100                 105                 110

Gly Arg Gln Trp Gly Gln Gly Thr Glu Val Thr Val Ser Ser
        115                 120                 125
```

<210> SEQ ID NO 98
<211> LENGTH: 129
<212> TYPE: PRT
<213> ORGANISM: Artificial Sequence
<220> FEATURE:
<223> OTHER INFORMATION: Synthetic Construct

<400> SEQUENCE: 98

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
```

```
                    35                  40                  45
Ala Ala Ile Thr Trp Arg Gly Ala Ser Thr Tyr Tyr Ala Asp Pro Val
    50                  55                  60

Lys Gly Arg Phe Thr Ile Ser Arg Asp Asn Ala Lys Asn Thr Val Tyr
 65                  70                  75                  80

Leu Gln Met Ser Ser Leu Lys Pro Glu Asp Thr Ala Val Tyr Tyr Cys
                 85                  90                  95

Ala Ala Glu Glu Pro Ser Tyr Tyr Ser Gly Ser Tyr Tyr Met Met
            100                 105                 110

Gly Asp Ser Tyr Asn Tyr Trp Gly Gln Gly Thr Gln Val Thr Val Ser
            115                 120                 125

Gly

<210> SEQ ID NO 99
<211> LENGTH: 125
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Glu Ser Gly Gly Gly Leu Val Gln Ala Gly Gly
 1               5                  10                  15

Ser Leu Arg Leu Ser Cys Thr Ala Ser Gly Arg Thr Phe Ser Asn Tyr
             20                  25                  30

Ala Met Gly Trp Phe Arg Gln Ala Pro Gly Lys Glu Arg Glu Phe Leu
         35                  40                  45

Ala Ala Ile Ser Arg Ser Gly Glu Ser Thr Asn Tyr Ala Thr Phe Val
    50                  55                  60

Lys Gly Arg Phe Thr Ile Ala Arg Asp Asn Ala Lys Asn Thr Val Ser
 65                  70                  75                  80

Leu Gln Met Asn Ser Leu Lys Pro Glu Asp Thr Ala Val Tyr Phe Cys
                 85                  90                  95

Ala Ala Lys Val Ala Val Leu Val Ser Thr Thr Tyr Asn Ser Gln Tyr
            100                 105                 110

Asp Tyr Trp Gly Gln Gly Thr Gln Val Thr Val Ser Ser
            115                 120                 125

<210> SEQ ID NO 100
<211> LENGTH: 5
<212> TYPE: PRT
<213> ORGANISM: Artificial Sequence
<220> FEATURE:
<223> OTHER INFORMATION: Synthetic Construct

<400> SEQUENCE: 100

Gly Gly Gly Gly Ala
 1               5

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct

<400> SEQUENCE: 101

Gly Gly Gly Gly Ala Gly Gly Gly Ala Gly Gly Gly Ser
 1               5                  10                  15
```

MONOVALENT ANTI-PROPERDIN ANTIBODIES AND ANTIBODY FRAGMENTS

SEQUENCE LISTING

The instant application contains a Sequence Listing which has been submitted electronically in ASCII format and is hereby incorporated by reference in its entirety. Said ASCII copy, created Jun. 18, 2019, is named 51196-003002_Sequence_Listing_6.18.19_ST25 and is 85,819 bytes in size.

BACKGROUND

The complement system plays a central role in the clearance of immune complexes and in immune responses to infectious agents, foreign antigens, virus-infected cells and tumor cells. Complement activation occurs primarily by three pathways: the classical pathway, the lectin pathway and the alternative pathway. Uncontrolled activation or insufficient regulation of the alternative complement pathway can lead to systemic inflammation, cellular injury and tissue damage. The alternative complement pathway has been implicated in the pathogenesis of a growing number of diverse diseases. Properdin positively regulates alternative complement pathway activation by binding and stabilizing the C3 and C5 convertase complexes (C3bBb and C3bnBb). Inhibition or modulation of properdin activity is an important therapeutic strategy to mitigate symptoms and slow progression of diseases associated with alternative complement pathway dysregulation. There continues to be an unmet need for effectively regulating properdin activity.

SUMMARY

Described herein are isolated monovalent antibodies and antibody fragments thereof that specifically or substantially specifically bind properdin and selectively block alternative complement pathway activation. By inhibiting the functional activity of properdin, the monovalent antibody described herein inhibits alternative complement pathway-induced assembly of the membrane attack complex. In addition, selective binding of a single properdin molecule with a monovalent antibody can reduce undesirable immune complexes, resulting from aggregation. Thus, the selective targeting of a single properdin monomer or multimer can, in turn, improve clinical benefits for patients with disease mediated by alternative complement pathway dysregulation.

In one embodiment, the disclosure is directed to an isolated monovalent antibody or antibody fragment thereof, where the antibody or antibody fragment thereof binds human properdin. In a particular embodiment, the antibody or fragment is a camelid antibody. In a particular embodiment, the antibody or fragment is a single-domain antibody. In a particular embodiment, the antibody or fragment binds to TSR0 and/or TSR1 of human properdin. In a particular embodiment, the antibody or fragment binds an epitope within the amino acid sequence LCQPCRSPRWSLWSTWAPCSVTCSEGSQLRYRRCVGWNGQ (SEQ ID NO: 8). In a particular embodiment, the antibody or fragment binds to mouse properdin with an affinity of less than 50 nM. In a particular embodiment, the antibody or fragment comprises at least one or all three CDRs selected from: a) a CDR-H1 including the amino acid sequence GRIFEVNMMA (SEQ ID NO: 9); b) a CDR-H2 including the amino acid sequence RVGTTX$_1$YADSVKG (SEQ ID NO: 10), where X$_1$ is a polar or a nonpolar amino acid; and c) a CDR-H3 including the amino acid sequence LQYX$_2$RYGGAEY (SEQ ID NO: 11), where X2 is a polar amino acid. In a particular embodiment, CDR-H2 includes the amino acid sequence RVGTTVYADSVKG (SEQ ID NO: 12). In a particular embodiment, CDR-H3 includes the amino acid sequence LQYDRYGGAEY (SEQ ID NO:13). In a particular embodiment, CDR-H2 includes the amino acid sequence RVGTTTYADSVKG (SEQ ID NO: 15). In a particular embodiment, CDR-H3 has the amino acid sequence LQYSRYGGAEY (SEQ ID NO: 14). In a particular embodiment, CDR-H3 has the amino acid sequence LQYDRYGGAEY (SEQ ID NO: 13). In a particular embodiment, CDR-H3 has the amino acid sequence LQYSRYGGAEY (SEQ ID NO: 14). In a particular embodiment, the antibody or fragment includes 3 CDRs with the following sequences: a) a CDR-H1 having the amino acid sequence GRISSIIHMA (SEQ ID NO: 16); b) a CDR-H2 having the amino acid sequence RVGTTVYADSVKG (SEQ ID NO: 12); and c) a CDR-H3 having the amino acid sequence LQYEKHGGADY (SEQ ID NO: 17). In a particular embodiment, the antibody includes 6 CDRs with the following sequences: a) a CDR-H1 having the amino acid sequence GYIFTNYPIH (SEQ ID NO: 18); b) a CDR-H2 having the amino acid sequence FIDPGGGYDEPDERFRD (SEQ ID NO: 19); c) a CDR-H3 having the amino acid sequence RGGGYYLDY (SEQ ID NO: 20); d) a CDR-L1 having the amino acid sequence RASQDISFFLN (SEQ ID NO: 21); e) a CDR-L2 having the amino acid sequence YTSRYHS (SEQ ID NO: 22); and f) a CDR-L3 having the amino acid sequence QHGNTLPWT (SEQ ID NO: 23). In a particular embodiment, the antibody includes 6 CDRs with the following sequences: a) a CDR-H1 having the amino acid sequence GFSLTTYGVH (SEQ ID NO: 24); b) a CDR-H2 having the amino acid sequence VIWSGGDTDYNASFIS (SEQ ID NO: 25); c) a CDR-H3 having the amino acid sequence NKDYYTNYDFTMDY (SEQ ID NO: 26); d) a CDR-L1 having the amino acid sequence KSSQSVLYSSNQKNFLA (SEQ ID NO: 27); e) a CDR-L2 having the amino acid sequence WASTRES (SEQ ID NO: 28); and f) a CDR-L3 having the amino acid sequence HQYLSSYT (SEQ ID NO: 29). In a particular embodiment, the antibody includes 6 CDRs with the following sequences: a) a CDR-H1 having the amino acid sequence GYTFIDYWIE (SEQ ID NO: 30); b) a CDR-H2 having the amino acid sequence EIFPGSGTINHNEKFKD (SEQ ID NO: 31); c) a CDR-H3 having the amino acid sequence EGLDY (SEQ ID NO: 32); d) a CDR-L1 having the amino acid sequence SASSSVSYIY (SEQ ID NO: 33); e) a CDR-L2 having the amino acid sequence DTSTLAS (SEQ ID NO: 34); and f) a CDR-L3 having the amino acid sequence QQWSRNPFT (SEQ ID NO: 35). In a particular embodiment, the antibody includes 6 CDRs with the following sequences: a) a CDR-H1 having the amino acid sequence GFSLTSYGVH (SEQ ID NO: 36); b) a CDR-H2 having the amino acid sequence VIWSGGSTDYNAAFIS (SEQ ID NO: 37); c) a CDR-H3 having the amino acid sequence NKDFYSNYDYTMDY (SEQ ID NO: 38); d) a CDR-L1 having the amino acid sequence KSSQSVLYSSNQKNFLA (SEQ ID NO: 27); e) a CDR-L2 having the amino acid sequence WASTRES (SEQ ID NO: 28); and f) a CDR-L3 having the amino acid sequence HQYLSSYT (SEQ ID NO: 29). In a particular embodiment, the antibody includes 6 CDRs with the following sequences: a) a CDR-H1 having the amino acid sequence GYTXTAYGIN (SEQ ID NO: 39); b) a CDR-H2 having the amino acid sequence YIYIGNGYTDYNEKFKG (SEQ ID NO: 40); c) a CDR-H3 having the amino acid sequence SGWDEDYAMDF (SEQ ID NO: 41); d) a CDR-L1 having the amino acid sequence RASENIYSYLA (SEQ ID NO: 42); e) a CDR-L2 having the amino acid sequence HAKTLAE (SEQ ID NO: 43); and f) a CDR-L3 having the amino acid sequence QHHYGPPPT (SEQ ID NO: 44). In a particular embodiment, the antibody or fragment inhibits an activity of human properdin.

In one embodiment, the disclosure is directed to use of an isolated monovalent antibody or antibody fragment thereof that binds human properdin in a method of treating a disease mediated by alternative complement pathway dysregulation or in the manufacture of a medicament for treating a disease mediated by alternative complement pathway dysregulation.

In one embodiment, the disclosure is directed to a method of treating a disease mediated by alternative complement pathway dysregulation. The methods includes administering an effective amount of the antibody of an isolated monovalent antibody or antibody fragment thereof, where the antibody or antibody fragment binds human properdin to a patient in need thereof. In a particular embodiment, the disease is autoimmune thrombotic thrombocytopenic purpura (TTP), hemolytic uremic syndrome (HUS), atypical hemolytic uremic syndrome (aHUS), paroxysmal nocturnal hemoglobinuria (PNH), IgA nephropathy (Berger's disease), asthma (e.g., severe asthma), C3 glomerulopathy (C3G), Gaucher disease, Hidradentitis suppurativa, Behcet's disease, severe burn, early sepsis, dermatomyositis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMD), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, rheumatoid arthritis, dialysis (cardiovascular risk), cardiovascular disease, placental malaria, antiphospholipid syndrome (APS) pregnancy loss, membranoproliferative (MP) glomerulonephritis, membranous nephritism, encephalitis, brain injury, N-methyl-D-aspartate (NMDA) receptor antibody encephalitis, malaria hemolytic crisis, abdominal aortic aneurysm (AAA), or thoracoabdominal aortic aneurysm (TAA). In one embodiment, the disclosure is directed to a method of inhibiting alternative complement pathway membrane attack complex assembly. The method includes administering an effective amount of an antibody, antibody derivative or fragment thereof to a patient in need thereof. In a particular embodiment, the method inhibits alternative complement pathway dependent hemolysis.

In some embodiments, the antibody or fragment thereof includes the sequence of:

(SEQ ID NO: 45)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGSGGGGSGGGGSLEVQLVESGGGL

VQAGGSLRLSCAASGRISSIIHMAWYRQAPGKQRELVAEISRVGTTVYAD

SVKGRFTISRDDAKNTVTLQMNSLKPEDTAVYYCNALQYEKHGGADYWGQ

GTQVTVSS.

In some embodiments, the antibody or fragment thereof includes the sequence of:

(SEQ ID NO: 46)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGSGGGGSGGGGSEVQLLESGGGLV

QPGGSLRLSCAASGRISSIIHMAWFRQAPGKERELVSEISRVGTTVYADS

VKGRFTISRDNSKNTLYLQMNSLKPEDTAVYYCNALQYEKHGGADYWGQG

TLVTVSS.

In some embodiments, the antibody or fragment thereof includes the sequence of:

(SEQ ID NO: 47)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGDGGGGDGGGGEVQLVESGGGLVQ

AGGSLRLSCAASGRISSIIHMAWYRQAPGKQRELVAEISRVGTTVYADSV

KGRFTISRDDAKNTVTLQMNSLKPEDTAVYYCNALQYEKHGGADYWGQGT

QVTVSS.

In some embodiments, the antibody or fragment thereof includes the sequence of:

(SEQ ID NO: 48)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGEGGGGEGGGGEVQLVESGGGLVQ

AGGSLRLSCAASGRISSIIHMAWYRQAPGKQRELVAEISRVGTTVYADSV

KGRFTISRDDAKNTVTLQMNSLKPEDTAVYYCNALQYEKHGGADYWGQGT

QVTVSS.

In some embodiments, the antibody or fragment thereof includes the sequence of:

(SEQ ID NO: 49)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGSGGGGSGGGGSEVQLVESGGGLV

QPGGSLRLSCAASGRISSIIHMAWVRQAPGKQRELVSEISRVGTTVYADS

VKGRFTISRDNSKNTLYLQMNSLRAEDTAVYYCNALQYEKHGGADYWGQG

TLVTVSS.

In some embodiments, the antibody or fragment thereof includes the sequence of:

(SEQ ID NO: 50)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGDGGGGDGGGGEVQLLESGGGLVQ

PGGSLRLSCAASGRISSIIHMAWFRQAPGKERELVSEISRVGTTVYADSV

KGRFTISRDNSKNTLYLQMNSLKPEDTAVYYCNALQYEKHGGADYWGQGT

LVTVSS.

In some embodiments, the antibody or fragment thereof includes the sequence of:

(SEQ ID NO: 51)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGEGGGGEGGGGEVQLLESGGGLVQ

PGGSLRLSCAASGRISSIIHMAWFRQAPGKERELVSEISRVGTTVYADSV

KGRFTISRDNSKNTLYLQMNSLKPEDTAVYYCNALQYEKHGGADYWGQGT

LVTVSS.

In some embodiments, the antibody or fragment thereof includes the sequence of:

(SEQ ID NO: 52)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGDGGGGDGGGGEVQLVESGGGLVQ

PGGSLRLSCAASGRISSIIHMAWVRQAPGKQRELVSEISRVGTTVYADSV

KGRFTISRDNSKNTLYLQMNSLRAEDTAVYYCNALQYEKHGGADYWGQGT

LVTVSS.

In some embodiments, the antibody or fragment thereof includes the sequence of:

(SEQ ID NO: 53)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSRKCCVECPPCPAPPVAGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.

In some embodiments, the antibody or fragment thereof is an LVP058 anti-properdin monovalent antibody VHH linked to an hG1 without a C1q binding domain and includes the sequence of:

(SEQ ID NO: 54)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCAVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

In some embodiments, the antibody or fragment thereof is an LVP058 anti-properdin monovalent antibody $V_{HH}$ linked to an anti-albumin $V_{HH}$ by a $(G4S)_3$ linker and includes includes the sequence of:

(SEQ ID NO: 55)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSGGGGSGGGGSGGGGSEVQLVESGGGLVKPG

GSLRLSCAASGRPVSNYAAAWFRQAPGKEREFVSAINWQKTATYADSVKG

RFTISRDNAKNSLYLQMNSLRAEDTAVYYCAAVFRVVAPKTQYDYDYWGQ

GTLVTVSS.

Definitions

As used herein, the term "monovalent antibody or antibody fragment thereof" refers to an antibody or antigen binding fragment thereof comprising a single binding domain, e.g., $V_H$ or $V_{HH}$, for an antigen, e.g., a single properdin molecule. In one embodiment, the bound antigen molecule is part of a multimer, e.g., a trimer or higher order multimer of properdin monomers. Antibodies generally, including monovalent antibodies or antibody fragments thereof, bind with a high degree of specificity to a particular antigen.

As used herein, the term "single domain antibody" defines molecules where the antigen binding site is present on, and formed by, a single immunoglobulin domain. Generally, the antigen binding site of an immunoglobulin single variable domain is formed by no more than three CDRs. The single variable domain may, for example, include a light chain variable domain sequence (a $V_L$ sequence) or a suitable fragment thereof; or a heavy chain variable domain sequence (e.g., a $V_H$ sequence or $V_{HH}$ sequence) or a suitable fragment thereof; as long as it is capable of forming a single antigen binding unit (i.e., a functional antigen binding unit that essentially is the single variable domain, such that the single antigen binding domain does not need to interact with another variable domain to form a functional antigen binding unit).

As used herein, the term "camelid antibody" refers to an antibody derived from a camelid species, for example, in a camel, dromedary, llama, alpaca or guanaco. Camelid antibodies differ from those of most other mammals in that they lack a light chain, and thus include only heavy chains with complete and diverse antigen binding capabilities (Hamers-Casterman, C. et al., *Nature*, 363:446-8, 1993).

As used herein, the term "$V_{HH}$" refers to a single heavy chain variable domain antibody devoid of light chains. $V_{HH}$ chains, for example, can be of the type that can be found in Camelidae or cartilaginous fish that are naturally devoid of light chains or to a synthetic and non-immunized $V_{HH}$ that can be constructed accordingly. Each heavy chain includes a variable region encoded by V-, D- and J-exons. A $V_{HH}$ may be a natural $V_{HH}$ antibody, e.g., a camelid antibody, or a recombinant protein including a heavy chain variable domain.

As used herein, the term an "isolated antibody" refers to an antibody that is substantially free of other antibodies having different antigenic specificities (e.g., an isolated antibody that binds to properdin is substantially free of contaminants, e.g., antibodies that do not bind to properdin). In addition, an "isolated" antibody is one that has been identified and separated and/or recovered from a component of its natural environment. Contaminant components of its natural environment are materials that could interfere with diagnostic or therapeutic uses for the antibody, and may include enzymes, hormones, and other proteinaceous or nonproteinaceous solutes.

As used herein, the term "specific binding" of an antibody or fragment thereof, polypeptide, or peptidomimetic is binding to a target molecule that is measurably different from binding to molecules that are not target molecules. As used herein, specific binding refers to a greater than 95% preference for binding a particular antigen versus background ("non-specific") binding. "Substantially specific" binding refers to a greater than about 80% preference for binding a particular antigen versus background. Binding can be measured using a variety of methods including, but not limited to, Western blot, immunoblot, enzyme-linked immunosorbant assay ("ELISA"), radioimmunoassay ("RIA"), immunoprecipitation, surface plasmon resonance, bio-layer interferometry, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS") and flow cytometry.

As used herein, the term "human properdin" refers to a 469 amino acid soluble glycoprotein found in plasma that has seven thrombospondin type I repeats (TSR) with the N-terminal domain, TSR0, being a truncated domain. Human properdin, a 53 kDa protein, includes a signal peptide (amino acids 1-28), and six, non-identical TSR repeats about 60 amino acids each, as follows: amino acids 80-134 (TSR1), amino acids 139-191 (TSR2), amino acids 196-255 (TSR3), amino acids 260-313 (TSR4), amino acids 318-377 (TSR5), and amino acids 382-462 (TSR6). Properdin is formed by oligomerization of a rod-like monomer into cyclic dimers, trimers, and tetramers. The amino acid sequence of human properdin is found in the GenBank database under the following accession numbers: for human properdin, see, e.g., GenBank Accession Nos. AAA36489, NP_002612, AAH15756, AAP43692, S29126 and CAA40914. Properdin is a positive regulator of the alternative complement activation cascade. Known binding ligands for properdin include C3b, C3bB and C3bBb (Blatt, A. et al., Immunol. Rev., 274:172-90, 2016).

As used herein, the term "mouse properdin" refers to a 457 amino acid soluble glycoprotein found in plasma that has seven TSRs with the N-terminal domain, TSR0, being truncated. Mouse properdin, a 50 kDa protein, includes a signal peptide (amino acids 1-24), and six, non-identical TSRs of about 60 amino acids each, as follows: amino acids 73-130 (TSR1), amino acids 132-187 (TSR2), amino acids 189-251 (TSR3), amino acids 253-309 (TSR4), amino acids 311-372 (TSR5), and amino acids 374-457 (TSR6). Mouse properdin is formed by oligomerization of a rod-like monomer into cyclic dimers, trimers, and tetramers. The amino acid sequence of mouse properdin is found, for example, in the GenBank database (Gen Bank Accession Nos. P11680 and S05478).

As used herein, the term "TSR0 domain" refers to the truncated domain of properdin that precedes the TSR1 domain of properdin. For example, the TSR0 domain of human properdin includes amino acids 28-76.

As used herein, the term "TSR1 domain" refers to the domain of properdin adjacent to the TSR0 domain of properdin. For example, the TSR0 domain of human properdin includes amino acids 77-134.

As used herein, the term "an activity of properdin" refers to the biological activity of properdin including, but not limited to, binding interactions that lead to the stability of the C3/C5 convertase. Properdin binds most avidly to C3b,Bb—the alternative pathway C3/C5 convertase, but also binds to C3b; C3b,B and C3b,Bb. One function is to stabilize the C3b,Bb complex allowing increased alternative pathway activation (Pangburn, M., Methods Enzymol., 162: 639-53, 1988; Nolan, K. & Reid, K., Methods Enzymol., 223:35-46, 1993). Properdin enhances formation of the alternative pathway C3 convertase by increasing binding of factor B to P,C3b complexes. Thus, properdin is an accelerator (positive regulator) of complement activation. Properdin also has been implicated in initiating activation of the alternative pathway by binding to the target surface and initiating C3/C5 convertase formation (Kemper C. & Hourcade, D., Mol. Immunol., 45:4048-56, 2008).

As used herein, the term "alternative complement pathway" refers to one of three pathways of complement activation (the others being the classical pathway and the lectin pathway). The alternative complement pathway is typically activated by bacteria, parasites, viruses or fungi, although IgA Abs and certain IgL chains have also been reported to activate this pathway.

As used herein, the term "alternative complement pathway dysregulation" refers to any aberration in the ability of the alternative complement pathway to provide host defense against pathogens and clear immune complexes and damaged cells and for immunoregulation. Alternative complement pathway dysregulation can occur both in fluid phase as well as at cell surface and can lead to excessive complement activation or insufficient regulation, both causing tissue injury.

As used herein, the term "a disease mediated by alternative complement pathway dysregulation" refers to an interruption, cessation or disorder of body functions, systems or organs caused by alternative complement pathway dysregulation. Such diseases would benefit from treatment with a composition or formulation described herein. In some embodiments, the disease is caused by any aberration in the ability of the alternative complement pathway to provide host defense against pathogens and clear immune complexes and damaged cells, and for immunoregulation. Also encompassed herein are diseases, directly or indirectly, mediated by dysregulation of one or more components of the alternative complement pathway, or a product generated by the alternative complement pathway.

As used herein, the term "alternative complement pathway-dependent membrane attack complex assembly" refers to a terminal complex formed as a result of alternative complement pathway activation and includes complement components C5, C6, C7, C8 and C9. Assembly of the membrane attack complex (MAC) leads to cell lysis.

As used herein, the term "alternative complement pathway dependent hemolysis" refers to the lysis of red blood cells mediated by increased alternative complement pathway-dependent MAC assembly and/or deposition on red blood cells.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. A linker may refer to a moiety (e.g., a polyethylene glycol (PEG) polymer) or an amino acid sequence (e.g., a 3-200 amino acid, 3-150 amino acid, or 3-100 amino acid sequence) occurring between two polypeptides or polypeptide domains to provide space and/or flexibility between the two polypeptides or polypeptide domains. An amino acid spacer may be part of the primary sequence of a polypeptide (e.g., joined to the spaced polypeptides or polypeptide domains via the polypeptide backbone). A linker may comprise one or more glycine and serine residues.

BRIEF DESCRIPTION OF THE DRAWINGS

FIG. 5A to FIG. 5C show the characterization of selected anti-properdin antibodies by mass spectrometry.

DETAILED DESCRIPTION

Figure 1:
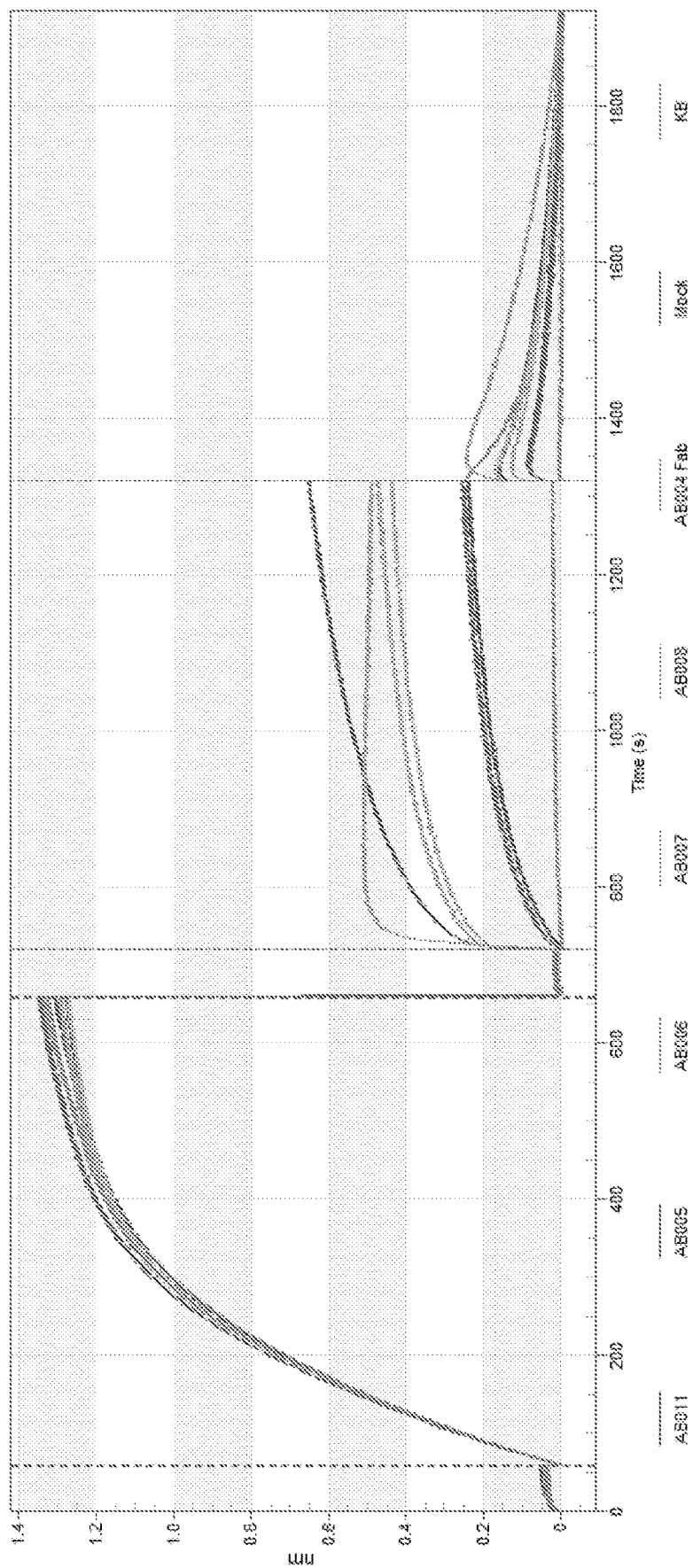
FIG. 1 depicts bio-layer interferometry data obtained using an Octet™ biosensor with a model system in which selected anti-properdin antibodies specifically bind human properdin. The graph shows equilibrium dissociation over time.

Properdin is a positive regulator of the alternative complement pathway. Described herein are novel monovalent antibodies that bind to a single properdin molecule and are useful for treating diseases mediated by dysregulation of the alternative complement pathway. Described herein is the discovery that immune complexes resulting from bivalent antibodies binding more than one properdin multimer exhibit toxicity as therapeutic agents for inhibiting aberrant activation of the alternative complement pathway. Monovalent antibodies described herein have a 1:1 binding ratio to properdin and, by design, cannot form antibody/properdin aggregates containing more than one properdin multimer, providing an advantage over bivalent and multivalent antibodies.

The sections that follow provide a description of monovalent antibodies or antibody fragments that can be administered to a patient with disease mediated by alternative complement pathway dysregulation.

Anti-Properdin Antibodies

Described herein are monovalent anti-properdin antibodies, antibody derivatives (e.g., engineered antibodies, humaneered antibodies, chimeric antibodies, substituted antibodies, humanized antibodies etc.) and antibody fragments thereof that inhibit properdin, a positive regulator of the alternate pathway of complement, and subsequently destabilize the C3- and C5-convertase enzyme complexes. The antibodies described herein can inhibit, for example, properdin binding to C3b, C3Bb, and C3bBb. Inhibition of properdin leads to reduced alternative pathway complement activation, indicating a therapeutic benefit for patients afflicted with a disease of alternative pathway dysregulation wherein the alternative pathway is hyper-activated.

Anti-properdin antibodies described herein can be produced by using full-length properdin, properdin polypeptides, and/or using antigenic properdin epitope-bearing peptides, for example, a fragment of the properdin polypeptide. Properdin peptides and polypeptides can be isolated and used to generate antibodies as natural polypeptides, recombinant or synthetic recombinant polypeptides. All antigens useful for producing anti-properdin antibodies can be used to generate monovalent antibodies. Suitable monovalent antibody formats, and methods for producing them, are known in the art (e.g., WO 2007/048037 and WO 2007/059782, the entire contents of which are incorporated herein by reference).

The anti-properdin antibody may be a monoclonal antibody or derived from a monoclonal antibody. Suitable monoclonal antibodies to selected antigens may be prepared by known techniques ("Monoclonal Antibodies: A manual of techniques," Zola (CRC Press, 1988); "Monoclonal Hybridoma Antibodies: Techniques and Applications," Hurrell (CRC Press, 1982), the entire contents of which are incorporated herein by reference).

In other embodiments, the antibody may be a single-domain antibody, such as a $V_{HH}$. Such antibodies exist naturally in camelids and sharks (Saerens, D. et al., *Curr. Opin. Pharmacol.*, 8:600-8, 2008). Camelid antibodies are described in, for example, U.S. Pat. Nos. 5,759,808; 5,800,988; 5,840,526; 5,874,541; 6,005,079; and 6,015,695, the entire contents of each of which are incorporated herein by reference. The cloned and isolated V$_{HH}$ domain is a stable polypeptide that features the full antigen-binding capacity of the original heavy-chain antibody. V$_{HH}$ domains, with their unique structural and functional properties, combine the advantages of conventional antibodies (high target specificity, high target affinity and low inherent toxicity) with important features of small molecule drugs (the ability to inhibit enzymes and access receptor clefts). Furthermore, they are stable, have the potential to be administered by means other than injection, are easier to manufacture, and can be humanized (U.S. Pat. Nos. 5,840,526; 5,874,541; 6,005,079, 6,765,087; EP 1589107; WO 97/34103; WO 97/49805; U.S. Pat. Nos. 5,800,988; 5,874,541 and 6,015,695, the entire contents of each of which are incorporated herein by reference).

In some embodiments, the antibody or antibody fragment thereof includes the following sequence as its heavy chain variable domain:

(SEQ ID NO: 71)
QVQLVESGGGLVQAGGSLRLSCAASGRTFSSYAMGWFRQAPGKEREFVAA

IGWNGEGIYYADSVKGRFTISRDNAKNTGYLQMNSLKPEDTAVYYCAADS

EGVVPGFPIAYWGQGTQVTVSG

In some embodiments, the antibody or antibody fragment thereof includes the following sequence as its heavy chain variable domain:

(SEQ ID NO: 72)
QVQLVESGGGLVQPGGSLRLSCAASGFPLNSYAIGWFRQAPGKEREGVSC

ISVSDDSTYYTDSVKGRFTISRDNAKNTVYLQMNSLKPEDTAVYYCAVDS

APLYGDYVCKPLENEYDFWGQGTQVTVSG.

In some embodiments, the antibody or antibody fragment thereof includes the following sequence as its heavy chain variable domain:

(SEQ ID NO: 73)
QVQLVESGGGLVQAGGSLXLSCAASGSDRRINGMGWYRHPPGKQRELVAA

ITSGGSTNYADSVKGRFTISTNNANNMMYLQMNSLKPEDTAVYYCAIDEF

GTGWLDYCGQGTQVTVSG.

In some embodiments, the antibody or antibody fragment thereof includes the following sequence as its heavy chain variable domain:

(SEQ ID NO: 74)
QVQLVESGGGLVQPGGSLRLSCAASGRPFSSYAMGWFRQAPGKEREIVAG

LSWSGGNVYYADSVKGRFTISRDNAKNTGDLQMNSLKPEDTAVYYCAIGP

KLTTGPTAYRYWGQGTQVTVSS

In some embodiments, the antibody or antibody fragment thereof includes the following sequence as its heavy chain variable domain:

(SEQ ID NO: 75)
QVQLVESGGGLVQPGGSLRLSCATSGGTFSSYAMGWFRQAPGKEREFVAA

ITWNGSNRYYADSVKGRFTISRDNAKSTVYLQMNSLKPEDTAVYYCAAEH

STRYSGFYYYTRGETYHYWGQGTQVTVSG

In some embodiments, the antibody or antibody fragment thereof includes the following sequence as its heavy chain variable domain:

(SEQ ID NO: 76)
QVQLVESGGGLVQAGGSLRLSCAASGRTFSTLGMGWFRQAPGKERQFVAA

INWSGSSTYYANSVKGRFTISRDNAQSTMYLQMNSLKPEDTAVYYCAADL

DSRYSAYYYYSDESQYDYWGQGTLVTVSG

In some embodiments, the antibody or antibody fragment thereof includes the following sequence as its heavy chain variable domain:

(SEQ ID NO: 77)
QVQVVESGGGLVQPGGSLSLSCAASGRTFSSYAMGWFRQAPGKEREFVAA

ITWDGANIYYADSVKGRFTLSRDNAENTVWLQLNSLKPEDTAVYYCAAAE

SGRYSGRDYYSAPGVYLYWGQGTLVTVSG

In some embodiments, the antibody or antibody fragment thereof includes the following sequence as its heavy chain variable domain:

(SEQ ID NO: 78)
QVQLVESGGGLVQAGGSLRLSCAASGSIFDINAMGWYRQAPGKQRELVAD

ITSSGSTNYADSVKGRFTISRDNAKNTVYLQMNSLKPEDTAVYTCAAESI

RESQNRHQLGYMGPLYDYWGQGTQVTVSG

In some embodiments, the antibody or antibody fragment thereof includes the following sequence as its heavy chain variable domain:

(SEQ ID NO: 79)
QVQLIESGGGLVQAGDSLRLSCAASEGTFSRFAMGWFRQAPGKEREFVAA

INWSGGITYYADSVKGRFTISRDNAKNTVYLQMNSLKPEDTADYYCAAET

TTRYSGYYYYEDNKSYDYWGQGTLVTVSG

In some embodiments, the antibody or antibody fragment thereof includes the following sequence as its heavy chain variable domain:

(SEQ ID NO: 58)
QVQVVESGGGLRQTGGSLRLSCTASGRIFEVNMMAWYRQAPGKQRELVAE

ISRVGTTVYADSVKGRFTISRDSAKNTVTLQMNSLKSEDTAVYYCNALQY

DRYGGAEYWGQGTQVTVSS

In some embodiments, the antibody or antibody fragment thereof includes the following sequence as its heavy chain variable domain:

(SEQ ID NO: 80)
QVLLEESGGGLERTGGSLRLSCAASGSIFSVNSMTWYRQAPGKRREFLGT

ITEEGRTNYADSVKGRFTISRDNAKNTMYLQMNSLKPEDTAVYYCYANLI

SSEDRTFGVWGQGTQVTVSS

In some embodiments, the antibody or antibody fragment thereof includes the following sequence as its heavy chain variable domain:

(SEQ ID NO: 81)
QVHLVESGGGLVQAGGSLRLSCTASGGTVGDYAVGWFRQAPGKERELIGV

VSRLGARTGYADSVLGRFTISRDDVKNTVFLQMDSVKPEDTAVYYCAARR

DYSFEVVPYDYWGQGTQVTVSG

In some embodiments, the antibody or antibody fragment thereof includes the following sequence as its heavy chain variable domain:

(SEQ ID NO: 82)
QVQMVESGGGLVQAGGSLRLSCAASGLTNRIRIMGWYRQAPGKLRELVAT

ITNDGSTHYADSVKGRFTISTDNAKNTVFLQMNSLKPEDTAVYICNVGEN

WGPAYWGQGTQVTVSG

In some embodiments, the antibody or antibody fragment thereof includes the following sequence as its heavy chain variable domain:

(SEQ ID NO: 72)
QVQLVESGGGLVQPGGSLRLSCAASGFPLNSYAIGWFRQAPGKEREGVSC

ISVSDDSTYYTDSVKGRFTISRDNAKNTVYLQMNSLKPEDTAVYYCAVDS

APLYGDYVCKPLENEYDFWGQGTQVTVSG

In some embodiments, the antibody or antibody fragment thereof includes the following sequence as its heavy chain variable domain:

(SEQ ID NO: 83)
QVRLTESGGGLVQYGTNLTLTCVASGLISTRNKMGWFRRRSGGQREFVAS

STVLSDDVIQDDIAETVKGRFAVARNDYKNILYLQMTAVKPEDTGFYWCA

SGTSLFGASRREDDFNAWGVGTQVTVSA

In some embodiments, the antibody or antibody fragment thereof includes the following sequence as its heavy chain variable domain:

(SEQ ID NO: 59)
QVQLAESGGGLVQAGDSLKLSCTASGRIFEVNMMAWYRQAPGKDRELVAE

ISRVGTTTYADSVKGRFTISRDSAKNTVTLQMNSLKSEDTAVYYCNALQY

SRYGGAEYWGQGTQVTVSG

In some embodiments, the antibody or antibody fragment thereof includes the following sequence as its heavy chain variable domain:

(SEQ ID NO: 84)
EVQLVESGGGLVQPGGSLRLSCAASGFTFGSADMSWVRQAPGKGPEWVSA

INSNGGSTYYAASVKGRFTISRDNAKNTLYLQMNSLKPEDTAVYYCAQGN

WYTEEYHYWGQGTLVTVSG

In some embodiments, the antibody or antibody fragment thereof includes the following sequence as its heavy chain variable domain:

(SEQ ID NO: 85)
QVRLVESGGGLVQAGDSLRLSCAASGRTLSSYAMGWFRQAPGKEREFVAA

TTWRDTSTYYADSVKGRFTISRDNAKNTVYLQMNSLKPEDTAAYYCAAEE

PSKYSGRDYYMMGDSYDYWGQGTQVTVSS

In some embodiments, the antibody or antibody fragment thereof includes the following sequence as its heavy chain variable domain:

(SEQ ID NO: 86)
EVQLVESGGGLVQPGGSLRLSCAASGFTFGSADMSWVRQAPGKGPEWVSA

INSNGGSTYYAASVKGRFTISRDNAKNTLYLQMNSLKPEDTAVYYCAQGN

WYTEEYHYWGQGTQVTVSG

In some embodiments, the antibody or antibody fragment thereof includes the following sequence as its heavy chain variable domain:

(SEQ ID NO: 87)
QVQLVESGGGLVQAGGSLRLSCAASGRTFSNYAMAWFRQAPGKEREFVAS

ISGSGDSRYYADSVKGRFTISRDNAKNTVYLQTNSPKPEDTAVYYCAAVL

PTRYSGFYYYSDGTQYHYWGQGTQVTVSS

In some embodiments, the antibody or antibody fragment thereof includes the following sequence as its heavy chain variable domain:

(SEQ ID NO: 88)
QVNLVESGGGSVQAGGSLRLSCAASENINVINDMGWYRQAPGKQRELVAV

ITGHDNINYADSATGRFTISTYTWNTENLQMNMLKPEDTAVYYCNADITY

ANGRFNDWGQGTQVTVSS

In some embodiments, the antibody or antibody fragment thereof includes the following sequence as its heavy chain variable domain:

(SEQ ID NO: 89)
QVHLVESGGGLVQAGGSLRLSCAASGRTFSSYAMGWFRQPPGKEREFVAA

ITWSGSSIYYADSVKGRFTISRDNAKNTVYLQMNSLKPEDTAVYYCAAEE

TSKYSGSYYYMMGDSYDYWGQGTQVTVSG

In some embodiments, the antibody or antibody fragment thereof includes the following sequence as its heavy chain variable domain:

(SEQ ID NO: 90)
QVQLVESGGGLVQAGGSLRLSCAASGRTFSSYAMGWFRQAPGKEREFVAA

VPWTYGSKYYADSVKGRFTISRDDAKNTVYLQMNNLKPEDTAVYYCAADS

SAGYYSGFDYYSAATPYDLWGQGTQVTVSG

In some embodiments, the antibody or antibody fragment thereof includes the following sequence as its heavy chain variable domain:

(SEQ ID NO: 91)
QVQLVESGGGLVQPGGSLRLSCAASGSDYYAIGWFRQAPGKEREGVSCMS

RTDGSTYYADSVKDRFTISRDYAKNTVYLQMNSLKPEDTAVYYCGLDRSY

PTGGISCLFGDFGSWGQGTQVTVSG

In some embodiments, the antibody or antibody fragment thereof includes the following sequence as its heavy chain variable domain:

(SEQ ID NO: 92)
QVQLVESGGGLVQAGGSLRLSCAASGRTFSSYNMGWFRQRHGNEREFVAT

ISWSGRSTYYADSVKGRFAISRDNANTTVYLQMNSLKPEDSAVYYCAAST

RGWYGTQEDDYNFWGQGTQVTVSG

In some embodiments, the antibody or antibody fragment thereof includes the following sequence as its heavy chain variable domain:

(SEQ ID NO: 60)
QVQLVESGGGLVQAGGSLRLSCAASGRISSIIHMAWYRQAPGKQRELVAE

ISRVGTTVYADSVKGRFTISRDDAKNTVTLQMNSLKPEDTAVYYCNALQY

EKHGGADYWGQGTQVTVSG

In some embodiments, the antibody or antibody fragment thereof includes the following sequence as its heavy chain variable domain:

(SEQ ID NO: 93)
QVQLVESGGGLVQAGGSLRLSCAASGGTFSSYSMGWFRQAPGKEREFVAA

ITWNGVSTYYADSVKGRFTISRDNAKNTVYLQMNSLKPTDTAVYYCAAEI

TTRYSGFYYYEDNKSYDYWGQGTQVTVSS

In some embodiments, the antibody or antibody fragment thereof includes the following sequence as its heavy chain variable domain:

(SEQ ID NO: 61)
QVQLVESGGGLRQTGESLRLSCTASGRIFEVNMMAWYRQAPGKQRELVAE

ISRVGTTTYADSVKGRFTISRDSAKNTVTLQMNSLKSEDTAVYYCNALQY

DRYGGAEYWGQGTQVTVSG

In some embodiments, the antibody or antibody fragment thereof includes the following sequence as its heavy chain variable domain:

(SEQ ID NO: 94)
EVQLVESGGGLVQPGGSLRLSCAASGFTLDYYAIGWFRQAPGKEREGVSC

ISRTDGSTYYADSVKGRFTISRDNAKNTVYLQMNSLKPEDTAVYYCAVDD

SYPTGGISCLFGHFGSWGQGTQVTVSS

In some embodiments, the antibody or antibody fragment thereof includes the following sequence as its heavy chain variable domain:

(SEQ ID NO: 95)
QVQLVESGGGLVQAGDSLRLSCAASGFTFSSYAMGWFRQAPGKEREFVAA

ITWSGVSTYYADSVKGRFTISRDNAKNRVYLQMNSLKPEDTAVYSCAADG

SGRYSGMEYYNRDWVYDYWGQGTQVTVSS

In some embodiments, the antibody or antibody fragment thereof includes the following sequence as its heavy chain variable domain:

(SEQ ID NO: 96)
QVHMVESGGGLVQAGGSLRFSCAASGNIFTISTLDWYRQAPGEQRELVAT

LTPDGITDYAGSVKGRFTISRDNAKNTVYLQMNSLKPEDTAVYYCNAWRY

SDDYRGRVDYWGQGTQVTVSG

In some embodiments, the antibody or antibody fragment thereof includes the following sequence as its heavy chain variable domain:

(SEQ ID NO: 97)
QVQLIESGGGLVQEGASLRLSCAGSGPMFSRLAVGWFRQAPGKEREFVAV

INWSGSADFYTNSVKGRFTISRDNAKNTVYLEMNTLKPEDSAVYYCAADQ

NPLTLRTGVRDVGRQWGQGTEVTVSS

In some embodiments, the antibody or antibody fragment thereof includes the following sequence as its heavy chain variable domain:

(SEQ ID NO: 98)
QVQLVESGGGLVQAGGSLRLSCAASGRTFSSYAMGWFRQAPGKEREFVAA

ITWRGASTYYADPVKGRFTISRDNAKNTVYLQMSSLKPEDTAVYYCAAEE

PSYYSGSYYYMMGDSYNYWGQGTQVTVSG

In some embodiments, the antibody or antibody fragment thereof includes the following sequence as its heavy chain variable domain:

(SEQ ID NO: 99)
QVQLVESGGGLVQAGGSLRLSCTASGRTFSNYAMGWFRQAPGKEREFLAA

ISRSGESTNYATFVKGRFTIARDNAKNTVSLQMNSLKPEDTAVYFCAAKV

AVLVSTTYNSQYDYWGQGTQVTVSS.

Anti-properdin antibodies, antibody derivatives and fragments thereof disclosed herein include those that have one or more, or all, of the following CDRs:

a. a CDR-H1 having the amino acid sequence
                                          (SEQ ID NO: 9)
      GRIFEVNMMA;

b. a CDR-H2 having the amino acid sequence
                                          (SEQ ID NO: 12)
      RVGTTVYADSVKG;

c. a CDR-H3 having the amino acid sequence
                                          (SEQ ID NO: 13)
      LQYDRYGGAEY.

Additional anti-properdin antibodies, antibody derivatives and fragments thereof disclosed herein include those that have one or more, or all, of the following CDRs:

a. a CDR-H1 having the amino acid sequence
(SEQ ID NO: 9)
GRIFEVNMMA;

b. a CDR-H2 having the amino acid sequence
(SEQ ID NO: 15)
RVGTTTYADSVKG;
and c. a CDR-H3 having the amino acid sequence
(SEQ ID NO: 14)
LQYSRYGGAEY.

Additional anti-properdin antibodies, antibody derivatives and fragments thereof disclosed herein include those that have one or more, or all, of the following CDRs:

a. a CDR-H1 having the amino acid sequence
(SEQ ID NO: 9)
GRIFEVNMMA;

b. a CDR-H2 having the amino acid sequence
(SEQ ID NO: 15)
RVGTTTYADSVKG;
and c. a CDR-H3 having the amino acid sequence
(SEQ ID NO: 13)
LQYDRYGGAEY.

Additional anti-properdin antibodies, antibody derivatives and fragments thereof disclosed herein include those that have one or more, or all, of the following CDRs:

a. a CDR-H1 having the amino acid sequence
(SEQ ID NO: 16)
GRISSIIHMA;

b. a CDR-H2 having the amino acid sequence
(SEQ ID NO: 12)
RVGTTVYADSVKG;
and c. a CDR-H3 having the amino acid sequence
(SEQ ID NO: 17)
LQYEKHGGADY.

Humanized camelid $V_{HH}$ polypeptides are taught, for example in WO04/041862, the teachings of which are incorporated herein in their entirety. It will be understood by one of skill in the art that naturally occurring camelid antibody single variable domain polypeptides can be modified (e.g., amino acid. substitutions at positions 45 and 103 (WO04/041862)) to generate humanized camelid $V_{HH}$ polypeptides. Also included herein are antibody single variable domain polypeptides that are nurse shark $V_{HH}$ (Greenberg, A. et al., Nature, 374:168-73, 1995; U.S. Patent Publication No. 20050043519).

Additional anti-properdin antibodies, antibody derivatives and fragments thereof disclosed herein include those that have one or more, or all (e.g., to create a scFv or dAb), of the following CDRs:

a) a CDR-H1 having the amino acid sequence
(SEQ ID NO: 18)
GYIFTNYPIH;

b) a CDR-H2 having the amino acid sequence
(SEQ ID NO: 19)
FIDPGGGYDEPDERFRD;

c) a CDR-H3 having the amino acid sequence
(SEQ ID NO: 20)
RGGGYYLDY;

d) a CDR-L1 having the amino acid sequence
(SEQ ID NO: 21)
RASQDISFFLN;

e) a CDR-L2 having the amino acid sequence
(SEQ ID NO: 22)
YTSRYHS;
and f) a CDR-L3 having the amino acid sequence
(SEQ ID NO: 23)
QHGNTLPWT.

Additional anti-properdin antibodies, antibody derivatives and fragments thereof disclosed herein include those that have one or more, or all (e.g., to create a scFv), of the following CDRs:

a) a CDR-H1 having the amino acid sequence
(SEQ ID NO: 24)
GFSLTTYGVH;

b) a CDR-H2 having the amino acid sequence
(SEQ ID NO: 25)
VIWSGGDTDYNASFIS;

c) a CDR-H3 having the amino acid sequence
(SEQ ID NO: 26)
NKDYYTNYDFTMDY;

d) a CDR-L1 having the amino acid sequence
(SEQ ID NO: 27)
KSSQSVLYSSNQKNFLA;

e) a CDR-L2 having the amino acid sequence
(SEQ ID NO: 28)
WASTRES;
and f) a CDR-L3 having the amino acid sequence
(SEQ ID NO: 29)
HQYLSSYT.

Additional anti-properdin antibodies, antibody derivatives and fragments thereof disclosed herein include those that have one or more, or all (e.g., to create a scFv), of the following CDRs:

a) a CDR-H1 having the amino acid sequence
(SEQ ID NO: 30)
GYTFIDYWIE;

b) a CDR-H2 having the amino acid sequence
(SEQ ID NO: 31)
EIFPGSGTINHNEKFKD;

c) a CDR-H3 having the amino acid sequence
(SEQ ID NO: 32)
EGLDY;

d) a CDR-L1 having the amino acid sequence
(SEQ ID NO: 33)
SASSSVSYIY;

e) a CDR-L2 having the amino acid sequence
(SEQ ID NO: 34)
DTSTLAS;
and f) a CDR-L3 having the amino acid sequence
(SEQ ID NO: 35)
QQWSRNPFT.

Additional anti-properdin antibodies, antibody derivatives and fragments thereof disclosed herein include those that have one or more, or all (e.g., to create a scFv), of the following CDRs:

```
a) a CDR-H1 having the amino acid sequence
                                    (SEQ ID NO: 36)
   GFSLTSYGVH;

b) a CDR-H2 having the amino acid sequence
                                    (SEQ ID NO: 37)
   VIWSGGSTDYNAAFIS;

c) a CDR-H3 having the amino acid sequence
                                    (SEQ ID NO: 38)
   NKDFYSNYDYTMDY;

d) a CDR-L1 having the amino acid sequence
                                    (SEQ ID NO: 27)
   KSSQSVLYSSNQKNFLA;

e) a CDR-L2 having the amino acid sequence
                                    (SEQ ID NO: 28)
   WASTRES;
and f) a CDR-L3 having the amino acid sequence
                                    (SEQ ID NO: 29)
   HQYLSSYT.
```

Additional anti-properdin antibodies, antibody derivatives and fragments thereof disclosed herein include those that have one or more, or all (e.g., to create a scFv), of the following CDRs:

```
a) a CDR-H1 having the amino acid sequence
                                    (SEQ ID NO: 39)
   GYTXTAYGIN;

b) a CDR-H2 having the amino acid sequence
                                    (SEQ ID NO: 40)
   YIYIGNGYTDYNEKFKG;

c) a CDR-H3 having the amino acid sequence
                                    (SEQ ID NO: 41)
   SGWDEDYAMDF;

d) a CDR-L1 having the amino acid sequence
                                    (SEQ ID NO: 42)
   RASENIYSYLA;

e) a CDR-L2 having the amino acid sequence
                                    (SEQ ID NO: 43)
   HAKTLAE;
and f) a CDR-L3 having the amino acid sequence
                                    (SEQ ID NO: 44)
   QHHYGPPPT.
```

In some embodiments, the antibody or antibody fragment thereof includes the following sequence:

```
                                                (SEQ ID NO: 53)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSRKCCVECPPCPAPPVAGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK
```

In some embodiments, the antibody or antibody fragment thereof includes the following sequence:

```
                                                (SEQ ID NO: 54)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCAVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K
```

In some embodiments, the antibody or antibody fragment thereof includes the following light chain and heavy chain sequences:

```
                                                (SEQ ID NO: 56)
DIQMTQSPSSLSASVGDRVTITCRASQDISFFLNWYQQKPGKAPKLLIYY

TSRYHSGVPSRFSGSGSGTDFTLTISSLQPEDFATYYCQHGNTLPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC;
and (SEQ ID NO: 57)
QVQLVQSGAEVKKPGASVKVSCKASGYIFTNYPIHWVRQAPGQGLEWMGF

IDPGGGYDEPDERFRDRVTMTRDTSTSTVYMELSSLRSEDTAVYYCARRG

GGYYLDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCAVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK
```

In some embodiments, the antibody or antibody fragment thereof includes the following sequence:

```
                                                (SEQ ID NO: 55)
LEVQLVESGGGLVQAGGSLRLSCAASGRISSIIHMAWYRQAPGKQRELVA

EISRVGTTVYADSVKGRFTISRDDAKNTVTLQMNSLKPEDTAVYYCNALQ

YEKHGGADYWGQGTQVTVSSGGGGSGGGGSGGGGSEVQLVESGGGLVKPG

GSLRLSCAASGRPVSNYAAAWFRQAPGKEREFVSAINWQKTATYADSVKG

RFTISRDNAKNSLYLQMNSLRAEDTAVYYCAAVFRVVAPKTQYDYDYWGQ

GTLVTVSS
```

In some embodiments, the antibody or antibody fragment thereof includes the following sequence:

(SEQ ID NO: 45)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYWGQGTLVTVSSGGGGSGGGGSGGGGSLEVQLVESGGGL

VQAGGSLRLSCAASGRISSIIHMAWYRQAPGKQRELVAEISRVGTTVYAD

SVKGRFTISRDDAKNTVTLQMNSLKPEDTAVYYCNALQYEKHGGADYWGQ

GTQVTVSS

Anti-Properdin Antibody Fragments and Derivatives

Some naturally occurring antibodies include two antigen binding domains and are therefore divalent. A number of smaller antigen binding fragments of naturally occurring antibodies have been identified following protease digestion. These include, for example, the "Fab fragment" ($V_L$-$C_L$-$C_H1$-$V_H$), "Fab' fragment" (a Fab with the heavy chain hinge region), and "F(ab')$_2$ fragment" (a dimer of Fab' fragments joined by the heavy chain hinge region). Recombinant methods have been used to generate such fragments and to generate even smaller antibody fragments, e.g., those referred to as "single chain Fv" (variable fragment) or "scFv," consisting of $V_L$ and $V_H$ joined by a synthetic peptide linker ($V_L$-linker-$V_H$). Fab fragments, Fab' fragments and scFv fragments are monovalent for antigen binding, as they each include only one antigen binding domain including one $V_H$/$V_L$ dimer. Even smaller monovalent antibody fragments are the dAbs, which include only a single immunoglobulin variable domain, e.g., $V_H$ or $V_L$, that alone specifically binds antigen, i.e., without the need for a complementary $V_L$ or $V_H$ domain, respectively. A dAb binds antigen independently of other V domains; however, a dAb can be present in a homo- or hetero-multimer with other $V_H$ or $V_L$ domains where the other domains are not required for antigen binding by the dAb, i.e., where the dAb binds antigen independently of the additional $V_H$ or $V_L$ domains.

Linkers

In the present invention, a linker is used to describe a linkage or connection between polypeptides or protein domains and/or associated non-protein moieties. In some embodiments, a linker is a linkage or connection between at least two polypeptide constructs, e.g., such that the two polypeptide constructs are joined to each other in tandem series (e.g., a monovalent antibody linked to a second polypeptide or monovalent antibody). A linker can attach the N-terminus or C-terminus of one antibody construct to the N-terminus or C-terminus of a second polypeptide construct.

A linker can be a simple covalent bond, e.g., a peptide bond, a synthetic polymer, e.g., a polyethylene glycol (PEG) polymer, or any kind of bond created from a chemical reaction, e.g., chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two antibody constructs, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

In the present invention, a linker between two peptide constructs can be an amino acid linker including from 1-200 (e.g., 1-4, 1-10, 1-20, 1-30, 1-40, 2-10, 2-12, 2-16, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200) amino acids. Suitable peptide linkers are known in the art, and include, for example, peptide linkers containing flexible amino acid residues such as glycine and serine. In certain embodiments, a linker can contain single motifs or multiple different or repeating motifs, of GS, GGS, GGGGS (SEQ ID NO: 1), GGSG (SEQ ID NO: 2), or SGGG (SEQ ID NO: 3). Exemplary motifs have the sequence of $(G4S)_n$, $(G4D)_n$, $(G4E)_n$, $(G4A)_n$ where n=1, 2, 3, 4, 5, or more, and combinations thereof. Other linkers include the sequences GGGGD (SEQ ID NO: 63), GGGGE (SEQ ID NO: 64), and GGGGA (SEQ ID NO: 100). Linkers can be designed by combining these various motifs. Such linkers include (SEQ ID NO: 4)
GGGGSGGGGSGGGGS, (SEQ ID NO: 5)
GGGGDGGGGDGGGG, (SEQ ID NO: 6)
GGGGEGGGGEGGGG,
and (SEQ ID NO: 101)
GGGGAGGGGAGGGGS.

Bispecific Constructs

The invention also features bispecific constructs where two antigen binding polypeptides are linked (e.g., by a linker such as the linker of any one of SEQ ID NOs: 1-6, 63-64, and 100-101). Such bispecific constructs may include an anti-properdin binding polypeptide (e.g., a monovalent antibody) connected by a linker to a second polypeptide (e.g., a second monovalent antibody). The second polypeptide can enhance in vivo stability of the bispecific construct. In some embodiments, the second polypeptide is an albumin binding molecule, an albumin binding peptide, or an anti-albumin antibody (e.g., a monovalent antibody), or a modified form thereof. Albumin binding peptides are known in the art and are described, for example, in WO 2007/106120 (see Tables 1 to 9) and Dennis et al., 2002, J Biol. Chem. 277: 35035-35043, the disclosures of which are hereby incorporated by reference.

In some embodiments, the second polypeptide is a Fc domain that enhances in vivo stability of the construct.

Exemplary bispecific constructs are shown below in Example 5.

In some embodiments, a monovalent anti-properdin antibody is linked to a monovalent anti-albumin antibody. The monovalent anti-properdin antibody may be linked by its N-terminus or C-terminus to the N-terminus or C-terminus of the monovalent anti-albumin antibody.

The monovalent anti-properdin antibody may be linked by its N-terminus or C-terminus to the N-terminus or C-terminus of the monovalent anti-albumin antibody with a linker with the amino acid sequence of any one of SEQ ID NOs: 1-6, 63-64, and 100-101.

In some embodiments, a monovalent anti-properdin antibody including the amino acid sequence of SEQ ID NO: 58 is linked to a monovalent anti-albumin antibody. The monovalent anti-properdin antibody including the sequence of SEQ ID NO: 58 may be linked by its N-terminus or C-terminus to the N-terminus or C-terminus of the monovalent anti-albumin antibody with a linker including the amino acid sequence of any one of SEQ ID NOs: 1-6, 63-64, and 100-101.

In some embodiments, a monovalent anti-properdin antibody including the amino acid sequence of SEQ ID NO: 59 is linked to a monovalent anti-albumin antibody. The monovalent anti-properdin antibody including the sequence of SEQ ID NO: 59 may be linked by its N-terminus or C-terminus to the N-terminus or C-terminus of the monovalent anti-albumin antibody with a linker including the amino acid sequence of any one of SEQ ID NOs: 1-6, 63-64, and 100-101.

In some embodiments, a monovalent anti-properdin antibody including the amino acid sequence of SEQ ID NO: 60 is linked to a monovalent anti-albumin antibody. The monovalent anti-properdin antibody including the sequence of SEQ ID NO: 60 may be linked by its N-terminus or C-terminus to the N-terminus or C-terminus of the monovalent anti-albumin antibody with a linker including the amino acid sequence of any one of SEQ ID NOs: 1-6, 63-64, and 100-101.

In some embodiments, a monovalent anti-properdin antibody including the amino acid sequence of SEQ ID NO: 61 is linked to a monovalent anti-albumin antibody. The monovalent anti-properdin antibody including the sequence of SEQ ID NO: 61 may be linked by its N-terminus or C-terminus to the N-terminus or C-terminus of the monovalent anti-albumin antibody with a linker including the amino acid sequence of any one of SEQ ID NOs: 1-6, 63-64, and 100-101.

In some embodiments, a monovalent anti-properdin antibody including the amino acid sequence of SEQ ID NO: 60 is linked at its N-terminus to a monovalent anti-albumin antibody with a linker including the sequence of SEQ ID NO: 4.

In some embodiments, a monovalent anti-properdin antibody including the amino acid sequence of SEQ ID NO: 60 is linked at its N-terminus to a monovalent anti-albumin antibody with a linker including the sequence of SEQ ID NO: 5.

In some embodiments, a monovalent anti-properdin antibody including the amino acid sequence of SEQ ID NO: 60 is linked at its N-terminus to a monovalent anti-albumin antibody with a linker including the sequence of SEQ ID NO: 6.

In some embodiments, the bispecific construct includes the amino acid sequence of any one of SEQ ID NOs: 45-55, and 62.

In some embodiments, a monovalent anti-properdin antibody is linked at its N-terminus to a monovalent anti-albumin antibody with a linker including the sequence of SEQ ID NO: 1.

In some embodiments, a monovalent anti-properdin antibody is linked at its N-terminus to a monovalent anti-albumin antibody with a linker including the sequence of SEQ ID NO: 2.

In some embodiments, a monovalent anti-properdin antibody is linked at its N-terminus to a monovalent anti-albumin antibody with a linker including the sequence of SEQ ID NO: 3.

In some embodiments, a monovalent anti-properdin antibody is linked at its N-terminus to a monovalent anti-albumin antibody with a linker including the sequence of SEQ ID NO: 4.

In some embodiments, a monovalent anti-properdin antibody is linked at its N-terminus to a monovalent anti-albumin antibody with a linker including the sequence of SEQ ID NO: 5.

In some embodiments, a monovalent anti-properdin antibody is linked at its N-terminus to a monovalent anti-albumin antibody with a linker including the sequence of SEQ ID NO: 6.

In some embodiments, a monovalent anti-properdin antibody is linked at its N-terminus to a monovalent anti-albumin antibody with a linker including the sequence of SEQ ID NO: 63.

In some embodiments, a monovalent anti-properdin antibody is linked at its N-terminus to a monovalent anti-albumin antibody with a linker including the sequence of SEQ ID NO: 64.

In some embodiments, a monovalent anti-properdin antibody is linked at its C-terminus to a monovalent anti-albumin antibody with a linker including the sequence of SEQ ID NO: 1.

In some embodiments, a monovalent anti-properdin antibody is linked at its C-terminus to a monovalent anti-albumin antibody with a linker including the sequence of SEQ ID NO: 2.

In some embodiments, a monovalent anti-properdin antibody is linked at its C-terminus to a monovalent anti-albumin antibody with a linker including the sequence of SEQ ID NO: 3.

In some embodiments, a monovalent anti-properdin antibody is linked at its C-terminus to a monovalent anti-albumin antibody with a linker including the sequence of SEQ ID NO: 4.

In some embodiments, a monovalent anti-properdin antibody is linked at its C-terminus to a monovalent anti-albumin antibody with a linker including the sequence of SEQ ID NO: 5.

In some embodiments, a monovalent anti-properdin antibody is linked at its C-terminus to a monovalent anti-albumin antibody with a linker including the sequence of SEQ ID NO: 6.

In some embodiments, a monovalent anti-properdin antibody is linked at its C-terminus to a monovalent anti-albumin antibody with a linker including the sequence of SEQ ID NO: 63.

In some embodiments, a monovalent anti-properdin antibody is linked at its C-terminus to a monovalent anti-albumin antibody with a linker including the sequence of SEQ ID NO: 64.

Generation of Single Domain Antibodies

In one embodiment, compositions and methods use a single domain antibody that is a heavy chain variable domain ($V_H$, e.g., $V_{HH}$) or a light chain domain ($V_L$). Thus, one means of generating monovalent single domain antibodies specific for properdin is to amplify and express the $V_H$ and $V_L$ regions of the heavy chain and light chain gene sequences isolated, for example, from a hybridoma (e.g., a mouse hybridoma) that expresses anti-properdin monoclonal antibody. The boundaries of $V_H$ and $V_L$ domains are set out, for example, by Kabat et al. (Sequences of Proteins of Immunological Interest (National Institutes of Health, Bethesda, Md., 1991). The information regarding the boundaries of the $V_H$ and $V_L$ domains of heavy and light chain genes is used to design PCR primers that amplify the V domain from a heavy or light chain coding sequence encoding an antibody known to bind properdin. The amplified V domains are inserted into a suitable expression vector, e.g., pHEN-1 (Hoogenboom, H. et al., *Nucleic Acids Res.,* 19:4133-7, 1991) and expressed, for example, as a fusion of the $V_H$ and $V_L$ in a scFv or other suitable monovalent format. The resulting polypeptide can then be screened for high affinity monovalent binding to properdin. Screening for binding can be performed by methods known in the art. Single domain antibodies can be generated using methods known in the art (WO2005118642; Ward, E. et al., *Nature,* 341:544-6, 1989; Holt, L. et al., *Trends Biotechnol.,* 21:484-90, 2003). Each light chain domain may be either of the kappa or lambda subgroup. Methods for isolating $V_H$ and $V_L$ domains have been described in the art (EP0368684).

In one embodiment, the single domain antibody is obtained from a human, humanized rodent, camelid or shark. Any such single domain antibody can be optionally humanized. Humanization of camelid single domain antibodies requires the introduction and mutagenesis of a limited number of amino acids in a single polypeptide chain. This is in contrast to humanization of scFv, Fab, (Fab')2 and IgG, which requires the introduction of amino acid changes in two chains, the light and the heavy chain and the preservation of the assembly of both chains. In some embodiments, the single domain antibody includes $V_{HH}$ domains. In some embodiments, the $V_{HH}$ domains correspond to the $V_{HH}$ domains of naturally occurring heavy chain antibodies directed against properdin. Such $V_{HH}$ sequences can be generated, for example, by suitably immunizing a species of camelid with properdin (i.e., so as to raise an immune response and/or heavy chain antibodies directed against properdin), by obtaining a suitable biological sample from said camelid (such as a blood sample, serum sample or sample of B-cells), and by generating $V_{HH}$ sequences directed against properdin, starting from said sample, using any suitable technique known in the art (e.g., the gene encoding the single domain antibody may be cloned by single cell PCR, or the B-cell(s) encoding the single domain antibody may be immortalized by EBV transformation, or by fusion to an immortal cell line).

Alternatively, such naturally occurring $V_{HH}$ domains against properdin, can be obtained from naive libraries of camelid $V_{HH}$ sequences, for example by screening such a library using properdin, or at least one part, fragment, antigenic determinant or epitope thereof using one or more screening techniques known in the art (WO 99/37681, WO 01/90190, WO 03/025020 and WO 03/035694). Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling (WO 00/43507). In a certain embodiment, a $V_{HH}$ library is constructed and expressed on phages after infection with helper phages. After several rounds of bio-panning, single domain antibodies against human properdin can be isolated and efficiently expressed.

A library of fusion proteins including $V_{HH}$ or $V_{HH}$ fragments can be displayed on a phage, phagemid, ribosome or suitable microorganism (such as yeast), to facilitate screening. Suitable methods, techniques and host organisms for displaying and screening (a set, collection or library of) fusion proteins including $V_{HH}$ or $V_{HH}$ fragments are known in the art (WO 03/054016; Hoogenboom, H., *Nat. Biotechnol.,* 23:1105-16, 2005).

In an additional embodiment, the method for generating fusion proteins including $V_{HH}$ or $V_{HH}$ fragment sequences includes at least the steps of: a) providing a collection or sample of cells derived from a species of camelid that express immunoglobulin sequences; b) screening the collection or sample of cells for (i) cells that express an immunoglobulin sequence that can bind to and/or have affinity for properdin; and (ii) cells that express heavy chain antibodies, in which substeps (i) and (ii) can be performed essentially as a single screening step or in any suitable order as two separate screening steps, to provide at least one cell that expresses a heavy chain antibody that can bind to and/or has affinity for properdin; and c) either (i) isolating from the cell the $V_{HH}$ sequence present in the heavy chain antibody; or (ii) isolating from the cell a nucleic acid sequence that encodes the $V_{HH}$ sequence present in the heavy chain antibody, followed by expressing the $V_{HH}$ domain.

The method for generating an amino acid sequence directed against properdin can include at least the steps of: a) providing a set, collection or library of nucleic acid sequences encoding heavy chain antibodies or $V_{HH}$ sequences; b) screening the set, collection or library of nucleic acid sequences for nucleic acid sequences that encode a heavy chain antibody or a fusion protein including the $V_{HH}$ sequence that can bind to and/or has affinity for properdin; and c) isolating the nucleic acid sequence, followed by expressing the $V_{HH}$ sequence present in the heavy chain antibody or by expressing the fusion protein including the $V_{HH}$ sequence, respectively.

Other suitable methods and techniques for obtaining the single domain antibodies and/or nucleic acids encoding the same, starting from naturally occurring $V_H$ sequences or $V_{HH}$ sequences may, for example, include combining one or more parts of one or more naturally occurring $V_{HH}$ sequences (such as one or more framework region (FR) sequences and/or CDR sequences), one or more parts of one or more naturally occurring $V_{HH}$ sequences (such as one or more framework region sequences or CDR sequences), and/or one or more synthetic or semi-synthetic sequences, in a suitable manner, so as to provide a monovalent anti-properdin single domain antibody or a nucleotide sequence or nucleic acid encoding the same. Nucleotide sequences encoding framework sequences of $V_{HH}$ or single domain antibodies are known in the art and may alternatively be obtained polymerase chain reaction (PCR) starting from the nucleotide sequences obtained using the methods described herein. Such compositions can be suitably combined with nucleotide sequences that encode the desired CDRs (for example, by PCR assembly using overlapping primers), to provide a single domain antibody, or antibody fragment fused with a regulator of the alternative complement pathway or fragment thereof.

Generation of Antibody Fragments

Antibody fragments that recognize the same epitope as a parent antibody can be generated by known techniques. For example, antibody fragments can be prepared by proteolytic hydrolysis of an antibody or by expression in E. coli of the DNA coding for the fragment. The antibody fragments are antigen binding portions of an antibody, such as Fab, F(ab')$_2$, and scFV can be obtained by pepsin or papain digestion of whole antibodies by conventional methods or by genetic engineering techniques.

An antibody fragment can be produced by enzymatic cleavage of antibodies with pepsin to provide a 100 kDa fragment denoted F(ab')$_2$. This fragment can be further cleaved using a thiol reducing agent, and optionally a blocking group for the sulfhydryl groups resulting from cleavage of disulfide linkages, to produce 50 kDa Fab' monovalent fragments. Alternatively, an enzymatic cleavage using papain produces two monovalent Fab fragments and an Fc fragment directly (U.S. Pat. Nos. 4,036,945 and 4,331,647; Nisonoff, A. et al., Arch. Biochem. Biophys., 89:230-44, 1960; Porter, R., Biochem. J., 73:119-26, 1959; Edelman et al., in Methods in Enzymology Vol. I, page 422 (Academic Press 1967), and Coligan el al., Current Protocols in Immunology, Vol. 1, pages 2.8.1-2.8.10 and 2.10.-2.10.4 (John Wiley & Sons 1991).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Another form of an antibody fragment is a peptide coding for a single complementarity-determining region (CDR). CDR peptides can be obtained by constructing genes encoding the CDR of an antibody of interest. Such genes are prepared, for example, by using the polymerase chain reaction to synthesize the variable region from RNA of antibody producing cells (Larrick, J & Fry, K. METHODS—a companion to Methods in Enzymology Volume: New Techniques in Antibody Generation, 2:106-110, 1991); Courtenay-Luck, "Genetic Manipulation of Monoclonal Antibodies," in Monoclonal Antibodies: Production, Engineering and Clinical Application, Ritter et al. (eds.), pages 166-179 (Cambridge University Press 1995); and Ward et al., "Genetic Manipulation and Expression of Antibodies," in Monoclonal Antibodies: Principles And Applications, Birch et al., (eds.), pages 137-185 (Wiley-Liss, Inc. 1995)).

Other antibody fragments, for example single domain antibody fragments, are known in the art and may be used in the claimed constructs (Muyldermans, S. et al., Trends Biochem. Sci., 26:230-5, 2001; Yau, K. et al., J. Immunol. Methods, 281:161-75, 2003; Maass, D. et al., J. Immunol. Methods, 324:13-25, 2007). The V$_{HH}$ may have potent antigen binding capacity and can interact with novel epitopes that are inaccessible to conventional V$_H$-V$_L$ pairs. Camelidae may be immunized with known antigens, such as properdin, and VHHs can be isolated that bind to and neutralize the target antigen.

Screening Monovalent Antibodies for Antigen Binding

Library screening methods can be used to identify monovalent properdin-specific binding antibodies or fragments. Phage display technology provides an approach for the selection of antibodies that bind a desired target (e.g., human properdin) from among large, diverse repertoires of antibodies (Smith, G., Science, 228:1315-7, 1985; Scott, J. & Smith, G., Science, 249:386-90, 1990; McCafferty, J. et al., Nature, 348:552-4, 1990). These phage-antibody libraries can be grouped into two categories: natural libraries that use rearranged V genes harvested from human B-cells (Marks, J. et al., J. Mol. Biol., 222:581-97, 1991; Vaughan, T. et al., Nat. Biotechnol., 14:309-14, 1996) or synthetic libraries whereby germline V gene segments or other antibody polypeptide coding sequences are 'rearranged' in vitro (Hoogenboom, H. & Winter, G., J. Mol. Biol., 227:381-8, 1992; Nissim, A. et al., EMBO J., 13:692-8, 1994; Griffiths, A. et al., EMBO J., 13:3245-60, 1994; de Kruif, J. et al., J. Mol. Biol., 248:97-105, 1995) or where synthetic CDRs are incorporated into a single rearranged V gene (Barbas, C. et al., Proc. Natl. Acad. Sci. USA, 89:4457-61, 1992). Methods involving genetic display packages (e.g., phage display, polysome display) are suited for the selection of monovalent properdin-specific antibody constructs because they generally express only monovalent fragments, rather than whole, divalent antibodies, on the display packages. Methods for the preparation of phage display libraries displaying various antibody fragments are described in the preceding references and, for example, in U.S. Pat. No. 6,696,245, which is incorporated herein by reference in its entirety.

Following expression of a repertoire of single domain antibodies on the surface of phage, selection is performed by contacting the phage repertoire with immobilized target antigen (e.g., properdin), washing to remove unbound phage, and propagation of the bound phage, the whole process frequently referred to as "panning." This process is applicable to the screening of monovalent single domain antibodies and antibody fragments that can be expressed on a display library (e.g., scFv, Fab, (Fab')2, and V$_{HH}$; Harrison, J. et al., Meth. Enzymol., 267:83-109, 1996). Alternatively, phages are pre-selected for the expression of properly folded member variants by panning against an immobilized generic ligand (e.g., protein A or protein L) that is only bound by folded members (WO 99/20749). This has the advantage of reducing the proportion of non-functional members, thereby increasing the proportion of members likely to bind a target antigen. The screening of phage antibody libraries is generally described, for example, by.

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks, J. et al., Biotechnology (NY), 11:1145-9, 1993; de Kruif, J. et al., Proc. Natl. Acad. Sci. USA, 92:3938-42, 1995). Another alternative involves selection by binding biotinylated antigen in solution, followed by capture on streptavidin-coated beads. V$_{HH}$ coding sequences are known in the art and may be used to construct camelid V$_{HH}$ phage display libraries, which can be used for antibody fragment isolation by bio-panning techniques known in the art.

Expression of Anti-Properdin Antibodies

The manipulation of nucleic acids can be carried out in recombinant vectors. As used herein, "vector" refers to a discrete element that is used to introduce heterologous DNA into cells for the expression and/or replication thereof. Methods to select or construct and, subsequently, use such vectors are known to one of skill in the art. Numerous vectors are publicly available, including bacterial plasmids, bacteriophage, artificial chromosomes and episomal vectors. Such vectors may be used for simple cloning and mutagenesis. A vector is selected to accommodate a polypeptide coding sequence of a desired size. A suitable host cell is transformed with the vector after in vitro cloning manipulations. Each vector contains various functional components, which generally include a cloning (or "polylinker") site and an origin of replication. An expression vector can further comprise one or more of the following: enhancer element, promoter, transcription termination and signal sequences—each positioned in the vicinity of the cloning site such that they are operatively linked to the gene encoding the polypeptide.

Both cloning and expression vectors generally contain nucleic acid sequences that enable the vector to replicate in one or more selected host cells. Typically cloning vectors comprise sequence elements that enable the vector to replicate independently of the host chromosomal DNA and includes origins of replication or autonomously replicating sequences. Such sequences are known for a variety of bacteria, yeast and viruses.

For screened libraries described herein, the vectors can be expression vectors that enable the expression of a polypeptide library member. Selection is performed by separate propagation and expression of a single clone expressing the polypeptide library member or by use of any selection display system. For bacteriophage display, phage or phagemid vectors can be used. Phagemid vectors have an *E. coli* origin of replication (for double stranded replication) and also a phage origin of replication (for production of single-stranded DNA).

Purification and Concentration of Monovalent Antibodies

Monovalent antibodies secreted into the periplasmic space or into the medium of bacteria are harvested and purified according to known methods (Skerra, A. & Plückthun, A., Science, 240:1038-41, 1988; and Breitling, F. et al. (Gene, 104:147-53, 1991) describe the harvest of antibody polypeptides from the periplasm; Better, M. et al. (Science, 240:1041-3, 1988) describe harvest from the culture supernatant). For some antibody polypeptides, purification can also be achieved by binding to generic ligands, such as protein A or Protein L. Alternatively, the variable domains can be expressed with a peptide tag, e.g., the Myc, HA or 6×His tags, which facilitates purification by affinity chromatography. If necessary, monovalent anti-properdin antibodies are concentrated by any of several methods well known in the art, including, for example, ultrafiltration, diafiltration and tangential flow filtration. The process of ultrafiltration uses semi-permeable membranes and pressure to separate molecular species on the basis of size and shape. The pressure is provided by gas pressure or by centrifugation. By selection of a molecular weight cutoff smaller than the target antibody (usually ⅓ to ⅙ the molecular weight of the target polypeptide, the anti-properdin antibody is retained when solvent and smaller solutes pass through the membrane.

Pharmaceutical Compositions, Dosage and Administration

The antibodies described herein can be incorporated into pharmaceutical compositions suitable for administration to a subject. Typically, the pharmaceutical composition includes a monovalent anti-properdin antibody, antibody derivative or fragment thereof and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The term "pharmaceutically acceptable carrier" excludes tissue culture medium including bovine or horse serum. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol or sodium chloride in the composition. Pharmaceutically acceptable substances include minor amounts of auxiliary substances such as wetting or emulsifying agents, preservatives or buffers, which enhance the shelf life or effectiveness of the antibody.

The compositions as described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The final form depends on the intended mode of administration and therapeutic application. Typical compositions are in the form of injectable or infusible solutions, such as compositions similar to those used for passive immunization of humans with other antibodies. The composition(s) can delivered by, for example, parenteral injection (e.g., intravenous, subcutaneous, intraperitoneal, intramuscular).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the monovalent anti-properdin antagonist in the required amount in an appropriate solvent with one or a combination of ingredients enumerated above, as required, followed by filter sterilization. Generally, dispersions are prepared by incorporating the monovalent anti-properdin antagonist into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

The antibodies described herein can be administered by a variety of methods known in the art, although for many therapeutic applications, the preferred route/mode of administration is intravenous injection or infusion. The polypeptide can also be administered by intramuscular or subcutaneous injection.

As will be appreciated by the skilled artisan, the route and/or mode of administration will vary depending upon the desired results. In certain embodiments, the antibody may be prepared with a carrier that will protect the antibody against rapid release, such as a controlled release formulation, including implants, transdermal patches, and microencapsulated delivery systems. Monovalent single domain antibodies are suited for formulation as extended release preparations due, in part, to their small size—the number of moles per dose can be significantly higher than the dosage of, for example, full sized antibodies. Biodegradable, biocompatible polymers can be used, such as ethylene vinyl acetate, polyanhydrides, polyglycolic acid, collagen, polyorthoesters and polylactic acid. Prolonged absorption of injectable compositions can be attained by including in the composition an agent that delays absorption, for example, monostearate salts and gelatin. Many methods for the preparation of such formulations are known to those skilled in the art (e.g., Sustained and Controlled Release Drug Delivery Systems, J. R. Robinson, ed., Marcel Dekker, Inc., New York, 1978). Methods applicable to the controlled or extended release of antibodies such as the monovalent single domain antibodies disclosed herein are known (U.S. Pat. Nos. 6,306,406 and 6,346,274; U.S. Patent Application Nos: US20020182254 and US20020051808, the entire teachings of each of which are incorporated herein by reference).

In certain embodiments, a monovalent anti-properdin antibody, antibody derivative or fragment thereof can be orally administered, for example, with an inert diluent or an assimilable edible carrier. To administer a composition described herein by a method other than parenteral administration, it may be necessary to coat the compound with, or co-administer the compound with a material to prevent its inactivation.

Additional active compounds can also be incorporated into the compositions. In certain embodiments, a monovalent anti-properdin antibody, antibody derivative or fragment thereof is co-formulated with and/or co-administered with one or more additional therapeutic agents. For example, a monovalent anti-properdin antibody, antibody derivative or fragment thereof can be co-formulated and/or co-administered with one or more additional antibodies that bind other targets (e.g., antibodies that bind regulators of the alternative complement pathway). Such combination therapies may utilize lower dosages of the administered therapeutic agents, thus avoiding possible toxicities or complications associated with the various monotherapies. Additionally, the compositions described herein can be co-formulated or co-administered with other therapeutic agents to ameliorate side effects of administering the compositions described herein (e.g., therapeutic agents that minimize risk of infection in an immunocompromised environment, for example, anti-bacterial agents, anti-fungal agents and anti-viral agents).

The pharmaceutical compositions can include a "therapeutically effective amount" or a "prophylactically effective amount" of a monovalent anti-properdin antagonist (e.g., an antibody or derivative or fragment thereof). A "therapeutically effective amount" refers to an amount effective, at dosages and for periods of time necessary, to achieve the desired therapeutic result. A therapeutically effective amount of the antibody can vary according to factors such as the disease state, age, sex, and weight of the individual, and the ability of the monovalent anti-properdin antagonist to elicit a desired response in the individual. A "prophylactically effective amount" refers to an amount effective, at dosages and for periods of time necessary, to achieve the desired prophylactic result. In some embodiments, a prophylactic dose is used in subjects prior to or at an earlier stage of disease where the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. It is to be noted that dosage values can vary with the type and severity of the condition to be alleviated. It is to be further understood that for any particular subject, specific dosage regimens should be adjusted over time according to the individual need and the professional judgment of the administering clinician.

A non-limiting range for a therapeutically or prophylactically effective amount of a monovalent anti-properdin antibody, antibody derivative or fragment thereof is 0.1-20 mg/kg, more preferably 1-10 mg/kg. It is to be noted that dosage values can vary with the type and severity of the condition to be alleviated. It is to be further understood that for any particular subject, specific dosage regimens should be adjusted over time according to the individual need and the professional judgment of the administering clinician.

The efficacy of treatment with a monovalent anti-properdin antibody, antibody derivative or fragment thereof as described herein is judged by the skilled clinician on the basis of improvement in one or more symptoms or indicators of the disease state or disorder being treated. An improvement of at least 10% (increase or decrease, depending upon the indicator being measured) in one or more clinical indicators is considered "effective treatment," although greater improvements are preferred, such as 20%, 30%, 40%, 50%, 75%, 90%, or even 100%, or, depending upon the indicator being measured, more than 100% (e.g., two-fold, three-fold, ten-fold, etc., up to and including attainment of a disease-free state).

Use of Monovalent Anti-Properdin Antibodies

The compositions described herein can be used in methods of treating a disease or disorder mediated by alternative complement pathway dysfunction in an individual in need of such treatment, the method including administering to the individual a therapeutically effective amount of a composition that includes a monovalent anti-properdin antibody, antibody derivative or fragment thereof, preferably a composition including a single human immunoglobulin variable domain that binds human properdin. In one embodiment, the monovalent anti-properdin antibodies, antibody derivatives or fragments thereof described herein are useful in treating diseases mediated by alternative complement pathway dysregulation by inhibiting the alternative complement pathway activation in a mammal (e.g., a human). Such disorders include, without limitation, systemic lupus erythromatosus and lupus nephritis, rheumatoid arthritis, antiphospholipid (aPL) Ab syndrome, glomerulonephritis, paroxysmal nocturnal hemoglobinuria (PNH) syndrome, inflammation, organ transplantation, intestinal and renal I/R injury, asthma (e.g., severe asthma), atypical hemolytic-uremic syndrome (aHUS), spontaneous fetal loss, DDD, Macular degeneration, TTP, IgA nephropathy (Berger's disease), C3 glomerulopathy (C3G), Gaucher disease, Hidradentitis suppurativa, Behcet's disease, dermatomyositis, severe burn, early sepsis, pneumococcal meningitis, Alzheimer's disease, cancer metastasis, acute respiratory distress syndrome (ARDS), acute lung injury (ACI), transfusion-related lung injury (TRALI), hemodialysis induced thrombosis, epidermolysis bullosa acquisita (EBA), uveitis, Parkinson's disease, primary biliary atresia, antineutrophil cytoplasmic antibodies (ANCA) vasculitis, retinal degeneration, broad thrombotic microangiopathy (TMA), broad TMA (APS), hematopoietic stem cell therapy (HSCT) TMA, age-related macular degeneration (AMD), pre-eclampsia, hemolysis, elevated liver enzymes, and low platelet (HELLP) syndrome, multiple sclerosis, antiphospholipid syndrome (APS), relapsing polychondritis, ischemic injury, stroke, graft versus host disease (GvHD), chronic obstructive pulmonary disease (COPD), emphysema, atherosclerosis, acute coronary syndrome, hemorrhagic shock, dialysis (cardiovascular risk), cardiovascular disease, placental malaria, APS pregnancy loss, membranoproliferative (MP) glomerulonephritis, membranous nephritis, encephalitis, brain injury, NMDA receptor antibody encephalitis, malaria hemolytic crisis, abdominal aortic aneurysm (AAA), and thoracoabdominal aortic aneurysm (TAA).

EXAMPLES

The following examples are put forth so as to provide those of ordinary skill in the art with a disclosure and description of how the methods and compounds claimed herein are performed, made. They are intended to be purely exemplary and are not intended to limit the scope of the disclosure.

Example 1. Generation of $V_{HH}$-his in-Fusion Cloning Vector

The pBNJ391 vector was digested with the restriction enzymes BstEII and EcoRI to remove the hinge and Fc. The vector was gel purified, which produced a 1000 bp release product. Annealed oligos UDEC6629/6630 were cloned into the pBNJ391 vector with BstEII/EcoRI. The annealed oligos contained the following sequences:

```
UDEC 6629 forward primer:
                                    (SEQ ID NO: 65)
GTCACCGTGTCGAGCCATCATCACCATCATCACTGATGAG UDEC 6630 reverse primer:
                                    (SEQ ID NO: 66)
AATTCTCATCATTTGTCATCATCATCCTTATAGTCGCTCGACACG
```

The final vector contained a BstEII-6xHis-EcoRI Site.

Next, the pNGH0320 vector was digested with XhoI/BstEII (producing a 13 bp release product) and column purified. Next, a $V_{HH}$ phage clone template was used to PCR amplify an insert. Forward primer UDEC 6438 (GTCCACTCCCTCGAGGTGCAGCTGGTGGAGTCTGGG; SEQ ID NO: 67) and reverse primer UDEC 6442 (GCTCGACACGGTGACCTGGGTCCCCTGGCCCCA; SEQ ID NO: 68), were used. The PCR products were purified and subsequently used in an In-Fusion protocol for cloning.

The pBNJ391 vector was digested with BstEII/EcoRI (50 ng/µL). Both complementary oligonucleotides were re-suspended at the same molar concentration, using TE Buffer. Equal volumes of both complementary oligonucleotides (at equimolar concentration) were mixed in a 1.5 mL tube. The tube was placed in a standard heat block at 90-95° C. for 3-5 minutes. The tube was removed from the apparatus and allowed to cool to room temperature (or at least below 30° C.). The tube was stored on ice or at 4° C. until further use. A mix of 1 µL insert DNA (from the above nucleotide used for ligation to pBNJ391), 2 µL of pBNJ391 (EcoRI/BstEII, 100 ng), 1 µL of 10× Ligase Buffer (NEB B0202S Lot: 1091410), 1 µL of T4 DNA Ligase (NEB M0202L Lot: 0671502), and 5 µL of water formed the ligation reaction. The ligation reaction was incubated for 30 minutes at room temperature. 1 µL of the ligation reaction was transformed into 30 µL of DH10 chemical competent cells (InVitrogen 18297 Lot #1552241) and 750 µL of SOC (NEBB9020S Lot #2971403) was added. The tube was shaken for 1 hour at 37° C. and 10 µL and 100 µL were plated on an LB-carb/glucose plate. Plates were incubated over the weekend at room temperature.

Colonies were picked for PCR for insertion of the 6×His into pNGH0320. Eight colonies were screened and pBNJ391 was used as a negative control. 300 µL of TB/Carb/Glucose culture was added to isolated colonies and grown at 37° C. Forward primer UDEC5276 (CATAATAGCTGACAGACTAACAGACTG; SEQ ID NO: 69) and reverse primer UDEC1977 (CGAAACAAGCGCTCATGAGCCCGAAGT; SEQ ID NO: 70), were used. For a 20 µL PCR reaction, DNA from a single colony was added to 10 µL Go Taq Green PCR Mix, 0.2 µL Forward Primer (100 µM), 0.2 pt Reverse Primer (100 uM), and 9.6 µL H$_2$O, totaling 20 µL. PCR conditions are as follows: 95° C. for 3 minutes, 95° C. for 20 seconds, 50° C. for 20 seconds, and 72° C. for 1 minute 15 seconds. The cycle was repeated 30 times, followed by incubation at 72° C. for 5 minutes, and 4° C. until further use. 5 µL of the PCR product was mixed with 15 µL of water and run on a 2% E-gel. Two clones matched the predicted size. Plasmid maxi prep was performed using the overnight cultures with the Promega maxi prep kit.

To clone anti-properdin $V_{HH}$ antibodies in $V_{HH}$-His tag format using in-fusion ligation of $V_{HH}$ into pNGH0320, PCR was used to generate the $V_{HH}$ insert with UDEC 6438-Infusion Forward Primer and UDEC 6442-Infusion reverse Primer for amplification of $V_H$ phagemids from the Llama anti-properdin library pLNJ with an XhoI site for cloning into pNGH0317 by infusion. For a 60 µL PCR reaction, 30 µL 2×phusion PCR mix (NEB M0531s Lot: 0211412), 1 µL of bacterial culture, 0.1 µL Forward Primer UDEC 6438 (100 µM), 0.1 µL Reverse Primer UDEC 6442 (100 µM), and 28.8 µL H$_2$O, totaling 20 µL. PCR conditions are as follows: 98° C. for 3 minutes, 98 C for 10 seconds, 52 C for 15 seconds, 72 C for 30-60 seconds, followed by 72° C. for 5 minutes. The cycle was repeated 30 times and held at 4 C until further use. 5 µL of the PCR product was mixed with 15 µL of water and were run on a 2% E-gel. All clones matched the predicted size. Clones were pooled in reactions of eight and column purified using the Promega Wizard® SV Gel and PCR Clean-Up System, according to manufacturer's instructions. Plasmid maxi prep was performed using the overnight cultures with the Promega maxi prep kit.

For ligation of the insert, 2 µL of 5× In-Fusion HD Enzyme Premix (Clontech 639650 Lot: 1501713A), 2.5 µL of Vector pNGH0320 (XhoI/BstEII) 39.1 ng/µL (100 ng), 1 µL of purified PCR fragment (10-200 ng), and 4.5 µL of water formed the ligation reaction. The ligation reaction was incubated for 15 minutes at 50° C.

For transformation, Stellar™ competent cells (Clontech) were thawed in an ice bath just before use. After thawing, cells were mixed gently to ensure even distribution, and then 50 µL of competent cells were moved into a 14 mL round bottom tube (falcon tube). 1 (less than 5 ng of DNA) was added to the cells. The tube was placed on ice for 30 min. Next, the cells were heat shocked for exactly 45 sec at 42° C. Tubes were then placed on ice for 1-2 min. SOC medium was added to bring the final volume to 500 µL (SOC medium was warmed to 37 C before using). The tube was incubated while shaking (160-225 rpm) for 1 hr at 37° C. 10 μL of the solution was then place on LB plate containing carbenicillin. The plate was incubated overnight at 37 C.

A colony PCR screen was performed for insertion of the 24 $V_{HH}$ colonies for each pool. A total of 48 clones were picked for each pool. Vector pNGH0320.1 was used as a positive control. Forward primer UDEC5276 and reverse primer UDEC1977 were used. For a 20 μL PCR reaction, DNA from a single colony was added to 10 μL Go Taq Green PCR Mix, 0.2 μL Forward Primer (100 μM), 0.2 μL Reverse Primer (100 μM), and 9.6 μL H$_2$O, totaling 20 μL. PCR conditions are as follows: 95° C. for 3 minutes, 95° C. for 20 seconds, 50° C. for 20 seconds, and 72° C. for 1 minute 15 seconds. Repeat for 30 cycles, followed by 72° C. for 5 minutes, and hold 4° C. until further use. 5 μL of the PCR products was mixed with 15 μL of water and were run on a 2% E-gel. Sequence analysis was performed on all 48 clones.

Preliminary screening of an immunization-biased llama $V_{HH}$ phage display library resulted in identification of 192 VHHs that were ELISA positive for binding properdin. 57 VHHs were cloned and expressed with a 6× histidine tag. Of these, 34 VHHs were Octet-positive for binding properdin. A summary is shown below in Table 1.

TABLE 1

Summary of screening assay

| | Screening on h-IP | | Cross reactive screening on mouse and human IP | | Cross reactive screening on monkey and human IP | |
|---|---|---|---|---|---|---|
| | Standard Procedure | NGS | Standard Procedure | NGS | Standard Procedure | NGS |
| ELISA positive | 193 | | 233 | | 284 | |
| Unique sequence (>3 different a.a. in CDR-H$_3$) | 72 | NA | 134 | NA | 90 | NA |
| Cloned and expressed (with 6xhistidine tag) | 57 | NA | NA | NA | NA | NA |
| Octet positive | 34 | NA | NA | NA | NA | NA |
| Hemolysis positive (by using the purified VHH) | 4 | NA | NA | NA | NA | NA |

Four functional $V_{HH}$s were found to effectively inhibit alternative complement pathway-mediated hemolysis and are shown below in Table 2.

TABLE 2

Anti-properdin $V_{HH}$ sequences

```
Clone
ID      V_HH sequence

AB005   QVQVVESGGGLRQTGGSLRLSCTASGRIFEVNMMAWYRQAPGKQRELVAEISRVGTTVYA

DSVKGRFTISRDSAKNTVTLQMNSLKSEDTAVYYCNALQYDRYGGAEYWGQGTQVTVSS (SEQ ID NO: 58)

AB006   QVQLAESGGGLVQAGDSLKLSCTASGRIFEVNMMAWYRQAPGKDRELVAEISRVGTTTYAD

SVKGRFTISRDSAKNTVTLQMNSLKSEDTAVYYCNALQYSRYGGAEYWGQGTQVTVSG (SEQ ID NO: 59)

AB007   QVQLVESGGGLVQAGGSLRLSCAASGRISSIIHMAWYRQAPGKQRELVAEISRVGTTVYADS

VKGRFTISRDDAKNTVTLQMNSLKPEDTAVYYCNALQYEKHGGADYWGQGTQVTVSG (SEQ ID NO: 60)

AB008   QVQLVESGGGLRQTGESLRLSCTASGRIFEVNMMAWYRQAPGKQRELVAEISRVGTTTYAD

SVKGRFTISRDSAKNTVTLQMNSLKSEDTAVYYCNALQYDRYGGAEYWGQGTQVTVSG (SEQ ID NO: 61)
```

Example 2. Binding of Anti-Properdin $V_{HH}$ Antibodies to Human Properdin

FIG. 1 shows kinetic binding measurements can be performed on an Octet instrument (FortéBio Inc.). All washes, dilutions, and measurements are performed in Kinetic buffer (FortéBio cat 185032) with the plate shaking at 1000 rpm. Streptavidin Biosensors (Forté Bio Cat:18-5019 lot: 1405301) were equilibrated in Kinetic buffer for 10 min and then loaded with 50 nm of biotinylated human properdin. For the association phase, 10 µg/mL of selected anti-properdin antibody or kinetics buffer blank was added to the biosensors preloaded with biotinylated human properdin respectively. Results show binding of AB005, AB006, AB007 and AB008 to human properdin.

Figure 2:
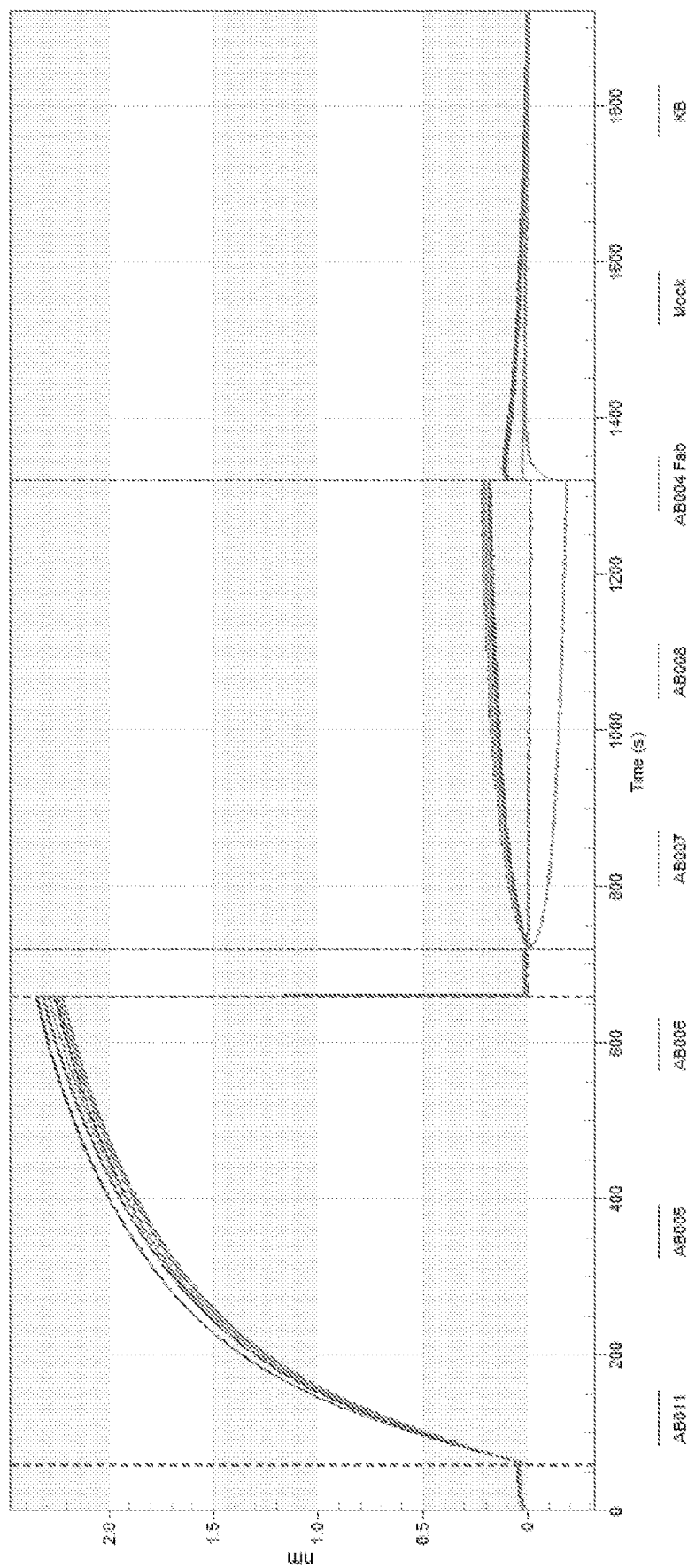
FIG. 2 depicts bio-layer interferometry data obtained using an Octet™ biosensor with a model system in which selected anti-properdin antibodies showed weak or no binding to mouse properdin. The graph shows equilibrium dissociation over time.

FIG. 2 shows kinetic binding measurements can be performed on an Octet instrument (FortéBio Inc). All washes, dilutions, and measurements are performed in Kinetic buffer (FortéBio cat 185032) with the plate shaking at 1000 rpm. Streptavidin Biosensors (Forté Bio Cat:18-5019 lot: 1405301) were equilibrated in Kinetic buffer for 10 min and then loaded with 50 nm of biotinylated mouse properdin. For the association phase, 10 µg/mL of selected anti-properdin antibody or kinetics buffer blank was added to the biosensors preloaded with biotinylated human properdin respectively. Results show weak binding or no binding of AB005, AB006, AB007, and AB008.

Figure 3:
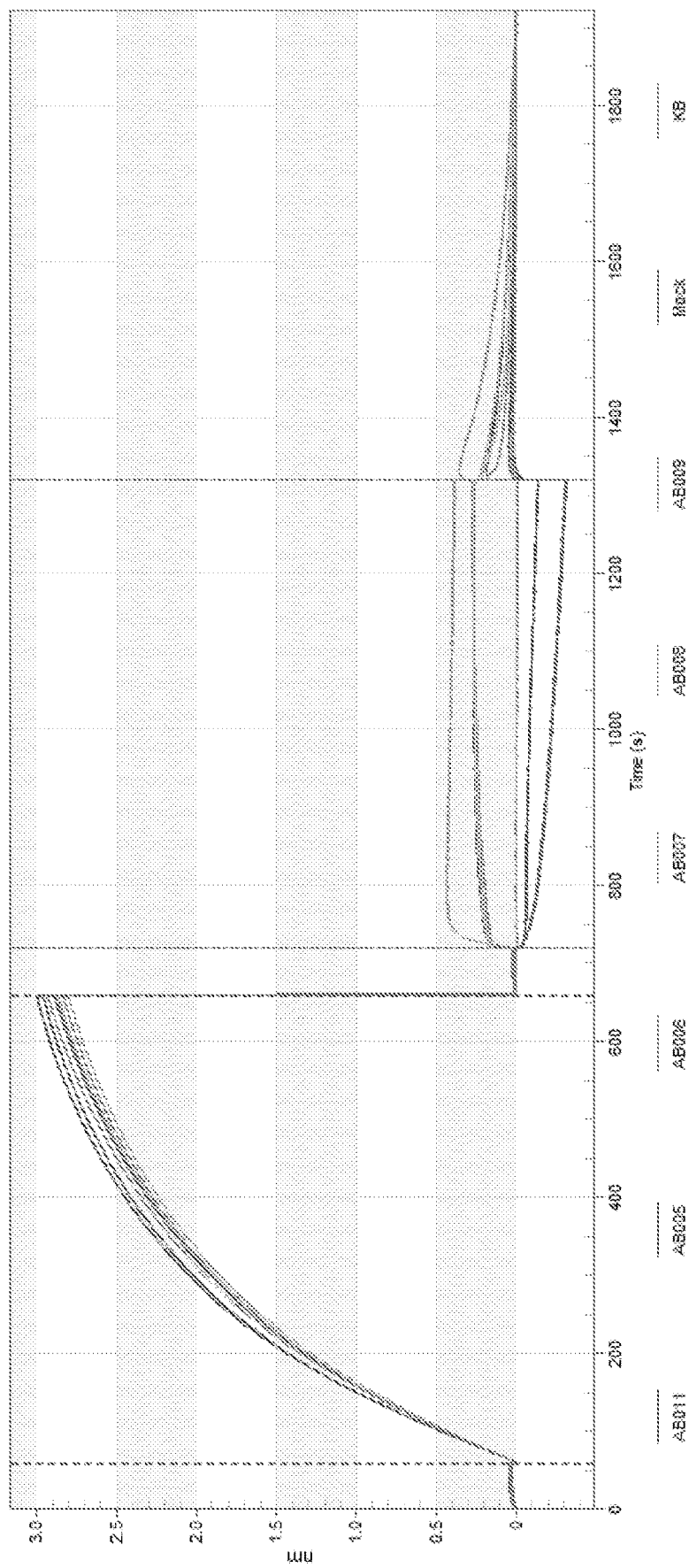
FIG. 3 depicts bio-layer interferometry data obtained using an Octet™ biosensor with a model system in which selected anti-properdin antibodies showed specific, but weak binding to cynomolgus properdin. The graph shows equilibrium dissociation over time.

FIG. 3 shows kinetic binding measurements can be performed on an Octet instrument (FortéBio Inc.). All washes, dilutions, and measurements are performed in Kinetic buffer (FortéBio cat 185032) with the plate shaking at 1000 rpm. Streptavidin Biosensors (Forte Bio Cat:18-5019 lot: 1405301) were equilibrated in Kinetic buffer for 10 min and then loaded with 50 nm of biotinylated cynomolgus properdin. For the association phase, 10 µg/mL of selected anti-properdin antibody or kinetics buffer blank was added to the biosensors preloaded with biotinylated human properdin respectively. Results show weak binding of AB005, AB006, AB007, and AB008 to cynomolgus properdin.

Example 3. Alternative Complement Hemolysis Assay

Figure 4:
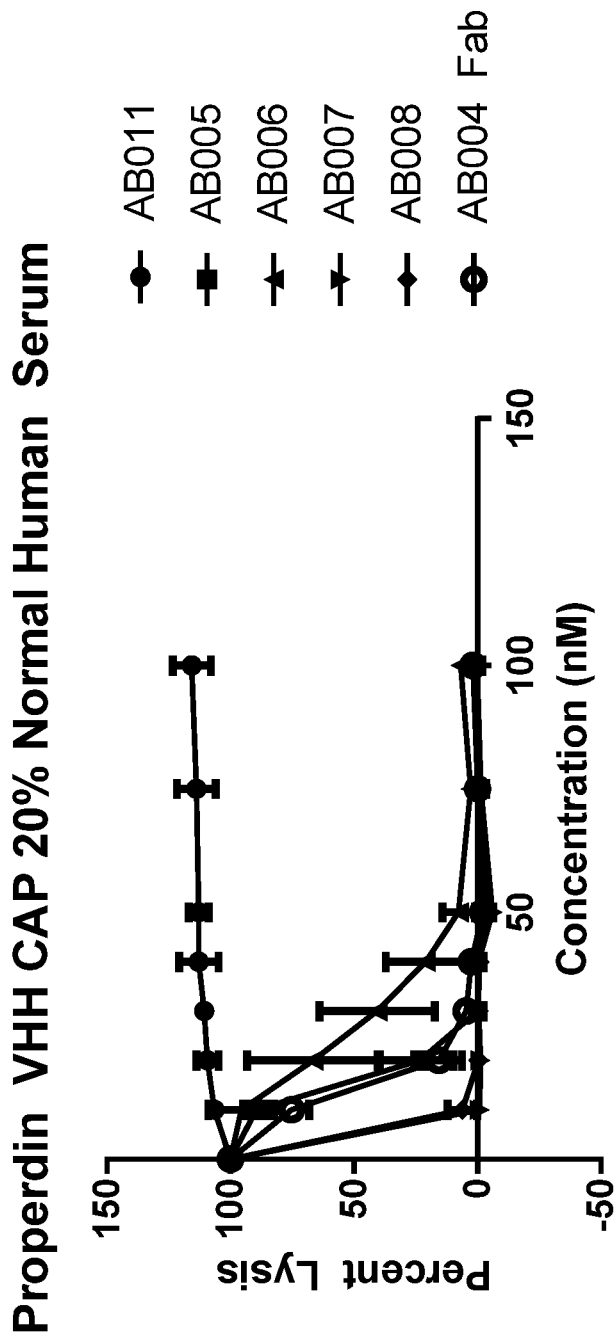
FIG. 4 shows that selected anti-properdin antibodies inhibit activity of human properdin in an alternative complement pathway hemolysis assay.

FIG. 4 shows an alternative complement pathway-mediated hemolysis assay based on the formation of a terminal complement-complex on the surface of the rabbit red blood cell (rRBC). As a result of the formation of this complex, the rRBCs are lysed. Agents that inhibit the formation of complement complexes are expected to inhibit cellular lysis. Various anti-properdin antigen binding fragments were tested to evaluate the effect on cellular lysis mediated by alternative complement activation. An "assay plate" was prepared by diluting 40% normal human serum with Gelatin veronal buffer (GVB) supplemented with 10 mM EGTA and 10 mM MgCl$_2$ (e.g., 1600 µL normal human serum into 2400 µLGVB supplemented with 10 mM EGTA and 10 mM MgCl$_2$). 50 µL of this solution was distributed into each well of the assay plate (polystyrene). Next, the dilution plate (polypropylene) was prepared by adding 50 µL/well of 2× mAbs (e.g., anti-properdin Fab) in GVB supplemented with 10 mM EGTA and 10 mM MgCl$_2$ at a concentration ranging from 0-100 nM to appropriate wells. As a positive control rabbit red blood cells were incubated in distilled water (100% lysis of cells) and for the negative control the red blood cells were incubated in GVB with 10 mM EDTA and 10 mM MgCl$_2$, respectively (0% lysis of cells).

50 µL/well was transferred from the dilution plate to assay plate. The assay plate was left at room temperature while proceeding to the next step. 400 µL of rRBCs were washed 4 times, each with 1 mL of GVB supplemented with 10 mM EGTA and 10 mM MgCl$_2$. rRBCs were spun at 2600 rpm for 1 minute after each wash. After the final wash, rRBCs were resuspend to a volume of 400 µL by adding 300 µL GVB supplemented with 10 mM EGTA and 10 mM MgCl$_2$. 50 µL of washed rRBCs were resuspended to 1 mL with GVB supplemented with 10 mM EGTA and 10 mM MgCl$_2$. 30 µL of this dilute solution was added to 100 µL of the prepared sample in the assay plate, yielding 1.5×10$^6$ cells/well. The plate was incubated for 30 minutes at 37° C. The plate was then centrifuged at 1000×g for 5 min and 85 µL of the supernatant was transferred to a flat bottom 96 well plate. Hemolysis was determined by measuring OD at 415 nm. A progressive decrease in light scatter (due to the lysis of intact cells) was measured at 415 nm as a function of concentration. For the calculation, the total inhibition was calculated at each concentration of the anti-properdin $V_{HH}$ and the results were expressed as a percentage of unlisted controls.

Figure 6B:
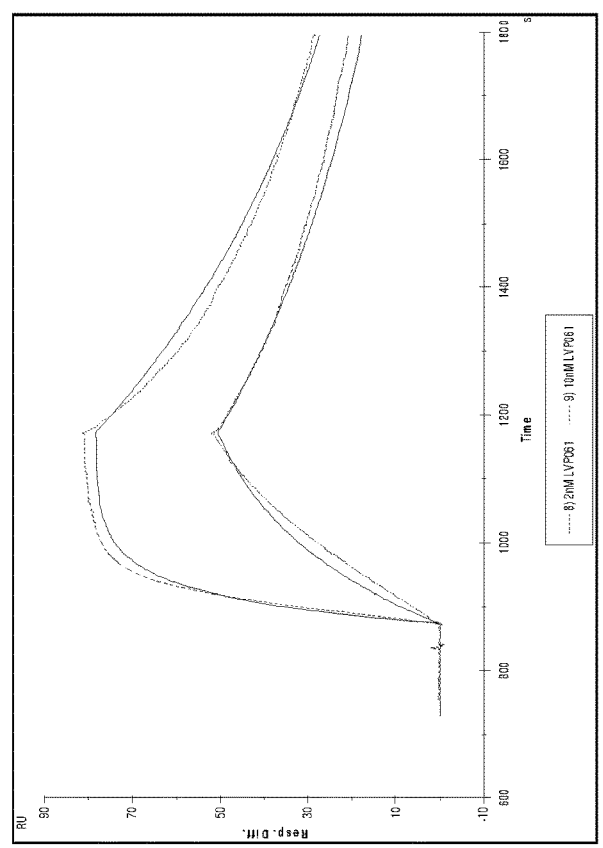
FIG. 6A and FIG. 6B show the binding affinity of selected anti-properdin antibodies to biotinylated properdin using a properdin capture method.
Figure 6A:
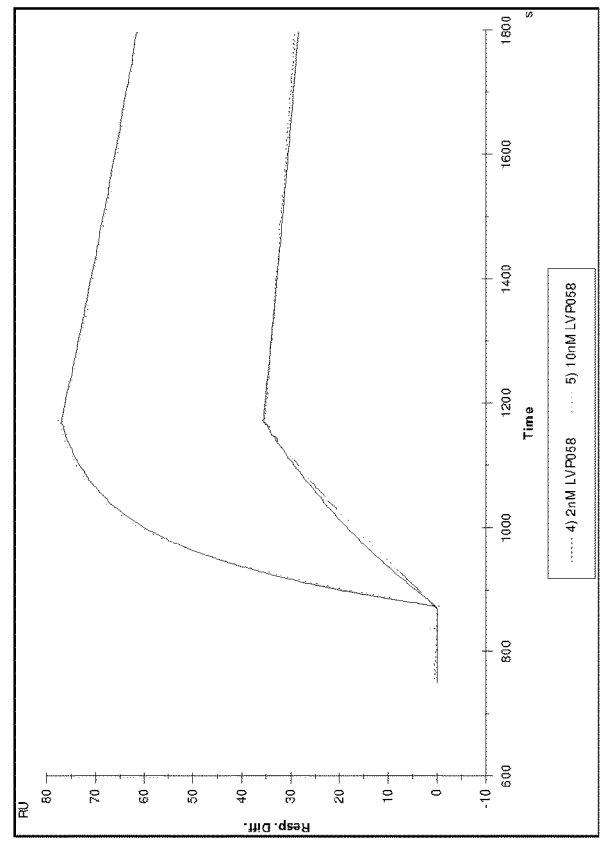

Example 4. Binding Kinetics of Monovalent Anti-Properdin $V_{HH}$ Antibodies to Properdin In FIG. 6, anti-properdin $V_{HH}$ antibodies AB007 and AB008, respectively, were run at known concentrations over an immobilized sensor surface. Response level (RU) was plotted against time in the sensorgrams.

The binding affinities of anti-properdin $V_{HH}$ antibodies were determined. The results are summarized in Table 3 below.

TABLE 3

| | Binding kinetics | | | |
|---|---|---|---|---|
| Sample | $k_a$ (1/Ms) | $k_d$ (1/s) | $K_D$ (M) | Chi$^2$ |
| AB007 | 1.04e6 | 3.59e−4 | 3.44e−10 | 0.36 |
| AB008 | 2.11e6 | 1.69e−3 | 8.03e−10 | 5.29 |

| Sample | Antigen | $k_a$ (1/Ms) | $k_d$ (1/s) | $K_D$ (M) | Chi$^2$ | Comments |
|---|---|---|---|---|---|---|
| AB009 | Human Properdin | 1.69E+06 | 4.33E−05 | 2.55E−11 | 0.18 | Good Fit |
| AB010 | Human Properdin | 1.09E+07 | 7.17E−05 | 6.59E−12 | 0.11 | Good Fit |

Example 5. Binding Kinetics of Bispecific Anti-Properdin Antibodies to Properdin and Alternative Complement Hemolysis Assay Bispecific constructs were created based on the anti-properdin constructs described above linked with a linker to an anti-albumin construct. The binding to properdin and alternative complement hemolysis was measured in similar assays as described above. The sequences of the constructs are shown in Table 4 below.

TABLE 4 anti-properdin construct sequences

| Molecule | Description | AA Sequence |
|---|---|---|
| TPP-2225 | anti-Albumin LVP058 (G4S)₃ Linker | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGSGGGGSGGGGSLEVQLVE SGGGLVQAGGSLRLSCAASGRISSIIHMAWYRQAPGKQRELVAEISRVGT TVYADSVKGRFTISRDDAKNTVTLQMNSLKPEDTAVYYCNALQYEKHGG ADYWGQGTQVTVSS (SEQ ID NO: 45) |
| TPP-2951 | Humanized anti-Albumin LVP058 (G4S)₃ Linker (7-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGSGGGGSGGGGSEVQLLES GGGLVQPGGSLRLSCAASGRISSIIHMAWFRQAPGKERELVSEISRVGTT VYADSVKGRFTISRDNSKNTLYLQMNSLKPEDTAVYYCNALQYEKHGGA DYWGQGTLVTVSS (SEQ ID NO: 46) |
| TPP-3071 | anti-Albumin LVP058 (G4D)₂ (G4) Linker | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGDGGGGDGGGGEVQLVESG GGLVQAGGSLRLSCAASGRISSIIHMAWYRQAPGKQRELVAEISRVGTTV YADSVKGRFTISRDDAKNTVTLQMNSLKPEDTAVYYCNALQYEKHGGAD YWGQGTQVTVSS (SEQ ID NO: 47) |
| TPP-3072 | anti-Albumin LVP058 (G4E)₂ (G4) Linker | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGEGGGGEGGGGEVQLVESG GGLVQAGGSLRLSCAASGRISSIIHMAWYRQAPGKQRELVAEISRVGTTV YADSVKGRFTISRDDAKNTVTLQMNSLKPEDTAVYYCNALQYEKHGGAD YWGQGTQVTVSS (SEQ ID NO: 48) |
| TPP-3261 | Humanized anti-Albumin LVP058 (G4S)₃ Linker (3-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGSGGGGSGGGGSEVQLVES GGGLVQPGGSLRLSCAASGRISSIIHMAWVRQAPGKQRELVSEISRVGTT VYADSVKGRFTISRDNSKNTLYLQMNSLRAEDTAVYYCNALQYEKHGGA DYWGQGTLVTVSS (SEQ ID NO: 49) |
| TPP-3341 | Humanized anti-Albumin LVP058 (G4D)₂ (G4) Linker (7-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGDGGGGDGGGGEVQLVESG GGLVQPGGSLRLSCAASGRISSIIHMAWFRQAPGKERELVSEISRVGTTV YADSVKGRFTISRDNSKNTLYLQMNSLKPEDTAVYYCNALQYEKHGGAD YWGQGTLVTVSS (SEQ ID NO: 50) |
| TPP-3342 | Humanized anti-Albumin LVP058 (G4E)₂ (G4) Linker (7-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGEGGGGEGGGGEVQLLESG GGLVQPGGSLRLSCAASGRISSIIHMAWFRQAPGKERELVSEISRVGTTV YADSVKGRFTISRDNSKNTLYLQMNSLKPEDTAVYYCNALQYEKHGGAD YWGQGTLVTVSS (SEQ ID NO: 51) |
| TPP-3343 | Humanized anti-Albumin LVP058 (G4D)₂ (G4) Linker (3-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGDGGGGDGGGGEVQLVESG GGLVQPGGSLRLSCAASGRISSIIHMAWVRQAPGKQRELVSEISRVGTTV YADSVKGRFTISRDNSKNTLYLQMNSLRAEDTAVYYCNALQYEKHGGAD YWGQGTLVTVSS (SEQ ID NO: 52) |
| TPP-3344 | Humanized anti-Albumin-LVP058 (G4E)₂ (G4) Linker (3-backmutations) | EVQLVESGGGLVKPGGSLRLSCAASGRPVSNYAAAWFRQAPGKEREFV SAINWQKTATYADSVKGRFTISRDNAKNSLYLQMNSLRAEDTAVYYCAAV FRVVAPKTQYDYDYWGQGTLVTVSSGGGGEGGGGEGGGGEVQLVESG GGLVQPGGSLRLSCAASGRISSIIHMAWVRQAPGKQRELVSEISRVGTTV YADSVKGRFTISRDNSKNTLYLQMNSLRAEDTAVYYCNALQYEKHGGAD YWGQGTLVTVSS (SEQ ID NO: 62) |
| TP-2221 | LVP058_hG2-G4-V$_{HH}$ on silent human Fc | LEVQLVESGGGLVQAGGSLRLSCAASGRISSIIHMAWYRQAPGKQRELVA EISRVGTTVYADSVKGRFTISRDDAKNTVTLQMNSLKPEDTAVYYCNALQ YEKHGGADYWGQGTQVTVSSRKCCVECPPCPAPPVAGPSVFLFPPKPK DTLMISRTPEVTCVVVDVSQEDPEVQFNWYVDGVEVHNAKTKPREEQFN STYRVVSVLTVLHQDWLNGKEYKCKVSNKGLPSSIEKTISKAKGQPREPQ VYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSL GK (SEQ ID NO: 53) |
| TP-2222 | LVP058_hG1_noC1q-V$_{HH}$ on human Fc without C1q | LEVQLVESGGGLVQAGGSLRLSCAASGRISSIIHMAWYRQAPGKQRELVA EISRVGTTVYADSVKGRFTISRDDAKNTVTLQMNSLKPEDTAVYYCNALQ YEKHGGADYWGQGTQVTVSSPKSCDKTHTCPPCPAPELLGGPSVFLFPP KPKDTLMISRTPEVTCVVVDVSHEDPEVKFNWYVDGVEVHNAKTKPREE |

TABLE 4-continued anti-properdin construct sequences

| Molecule | Description | AA Sequence |
|---|---|---|
| | binding | QYNSTYRVVSVLTVLHQDWLNGKEYKCAVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 54) |
| TPP-2224 | LVP058 (G4S)$_3$-anti-Alb-tandem V$_{HH}$ | LEVQLVESGGGLVQAGGSLRLSCAASGRISSIIHMAWYRQAPGKQRELVA<br>EISRVGTTVYADSVKGRFTISRDDAKNTVTLQMNSLKPEDTAVYYCNALQ<br>YEKHGGADYWGQGTQVTVSSGGGGSGGGGSGGGGSEVQLVESGGGL<br>VKPGGSLRLSCAASGRPVSNYAAAWFRQAPGKEREFVSAINWQKTATYA<br>DSVKGRFTISRDNAKNSLYLQMNSLRAEDTAVYYCAAVFRVVAPKTQYDY<br>DYWGQGTLVTVSS (SEQ ID NO: 55) |
| TPP-2223 | Anti-properdin control antibody without C1q binding domain | Light Chain Sequence:<br>DIQMTQSPSSLSASVGDRVTITCRASQDISFFLNWYQQKPGKAPKLLIYYT<br>SRYHSGVPSRFSGSGSGTDFTLTISSLQPEDFATYYCQHGNTLPWTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQ<br>GLSSPVTKSFNRGEC (SEQ ID NO: 56)<br>Heavy Chain Sequence:<br>QVQLVQSGAEVKKPGASVKVSCKASGYIFTNYPIHWVRQAPGQGLEWM<br>GFIDPGGGYDEPDERFRDRVTMTRDTSTSTVYMELSSLRSEDTAVYYCA<br>RRGGGGYYLDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCAVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 57) |

Figure 7:
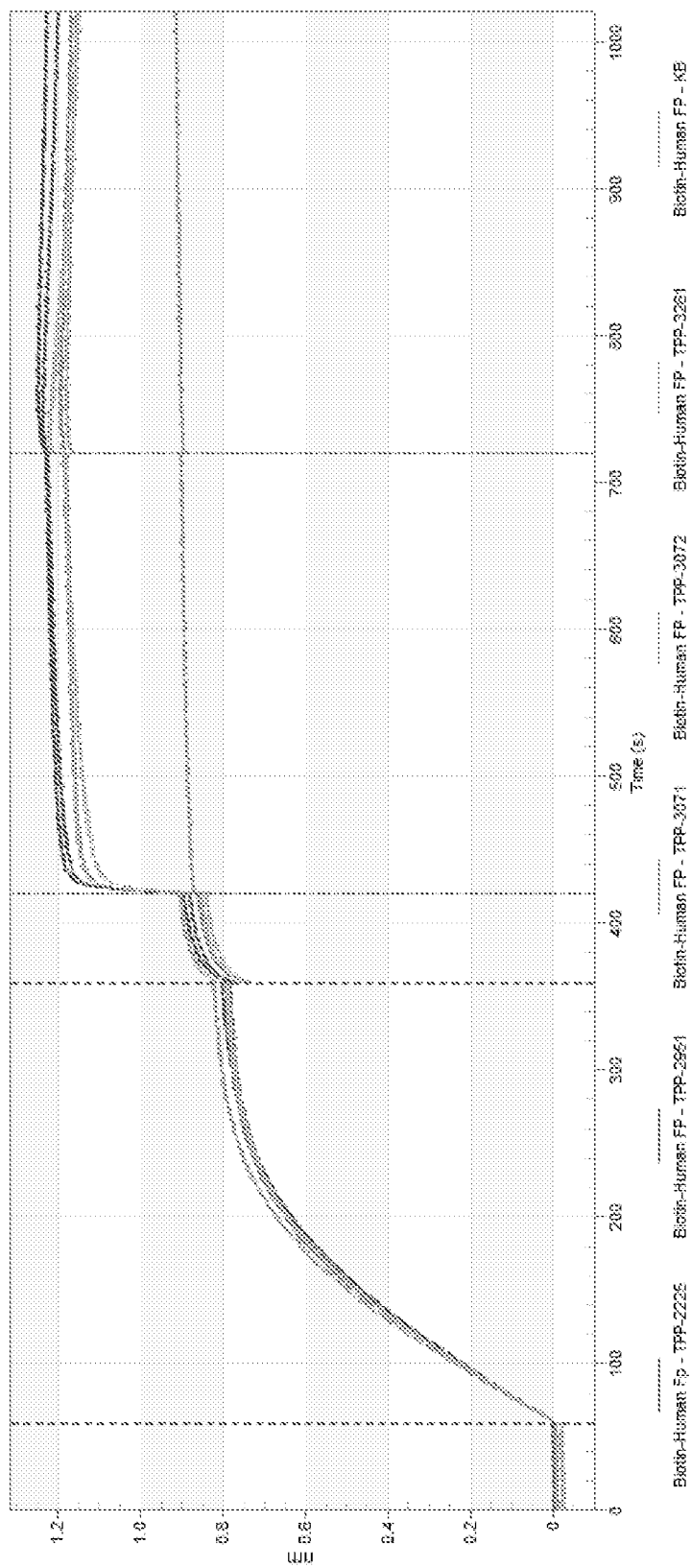
FIG. 7 shows the binding affinity of selected anti-properdin bispecific antibodies to biotinylated properdin using a properdin capture method.

FIG. 7 shows kinetic binding measurements performed on an Octet instrument (Forté Bio Inc.). All washes, dilutions, and measurements were performed in Kinetic buffer (FortéBio cat 185032) with the plate shaking at 1000 rpm. Streptavidin Biosensors (Forté Bio Cat:18-5019 lot: 1405301) were equilibrated in Kinetic buffer for 10 min and then loaded with 50 nm of biotinylated human properdin. For the association phase, 10 μg/mL of selected anti-properdin antibody or kinetics buffer blank was added to the biosensors preloaded with biotinylated human properdin, respectively. Results show binding of TPP-2225, TPP-2591, TPP-3071, TPP-3072, TPP-3261 to human properdin. The results show strong binding by all constructs to human properdin.

Figure 8A:
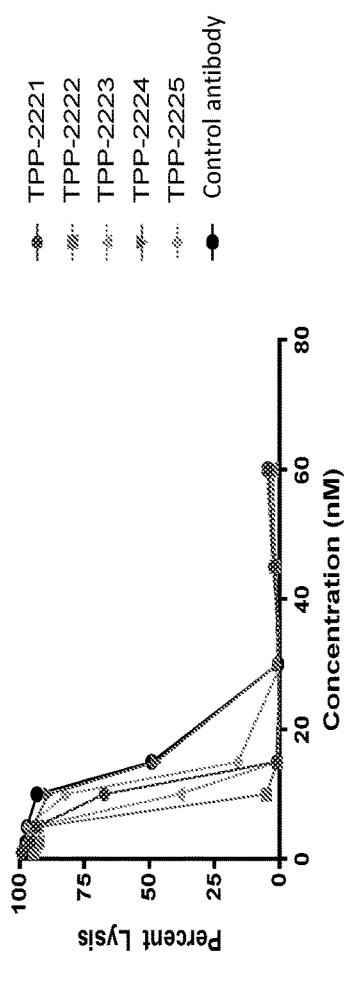
FIG. 8A and FIG. 8B show selected anti-properdin bispecific antibodies inhibit activity of human and cynomolgus properdin in an alternative complement pathway hemolysis assay. An anti-properdin antibody was used as the control.
Figure 8B:
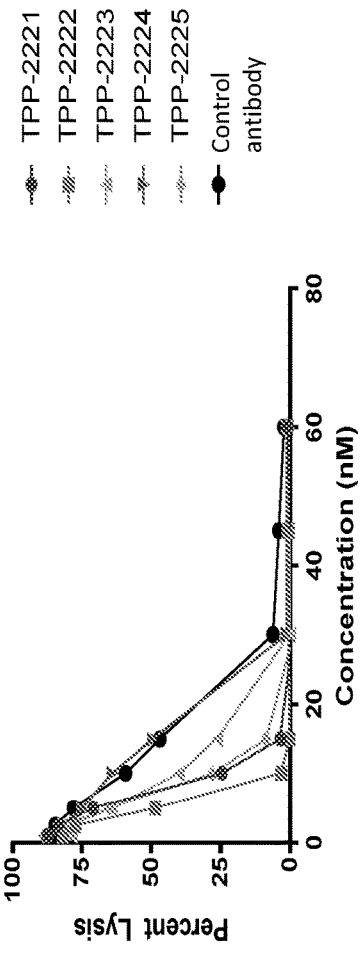

FIG. 8A-FIG. 8B show results of alternative complement pathway-mediated hemolysis assays based on the formation of a terminal complement-complex on the surface of the rabbit red blood cell (rRBC). As a result of the formation of this complex, the rRBCs are lysed. Agents that inhibit the formation of complement complexes are expected to inhibit cellular lysis. Various bispecific anti-properdin antigen binding constructs were tested to evaluate the effect on cellular lysis mediated by alternative complement activation. An "assay plate" was prepared by diluting 40% normal human serum with Gelatin veronal buffer (GVB) supplemented with 10 mM EGTA and 10 mM MgCl$_2$ (e.g., 1600 μL normal human serum into 2400 μLGVB supplemented with 10 mM EGTA and 10 mM MgCl$_2$). 50 μL of this solution was distributed into each well of the assay plate (polystyrene). Next, the dilution plate (polypropylene) was prepared by adding 50 μL/well of 2× mAbs (e.g., anti-properdin Fab) in GVB supplemented with 10 mM EGTA and 10 mM MgCl$_2$ at a concentration ranging from 0-100 nM to appropriate wells. As a positive control rabbit red blood cells were incubated in distilled water (100% lysis of cells) and for the negative control the red blood cells were incubated in GVB with 10 mM EDTA and 10 mM MgCl$_2$, respectively (0% lysis of cells).

Figure 9A:
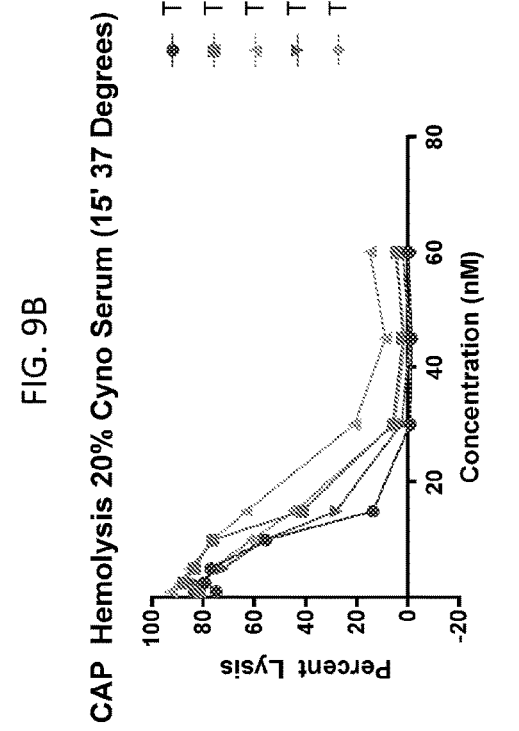
FIG. 9A and FIG. 9B show selected anti-properdin bispecific antibodies inhibit activity of human and cynomolgus properdin in an alternative complement pathway hemolysis assay.
Figure 9B:
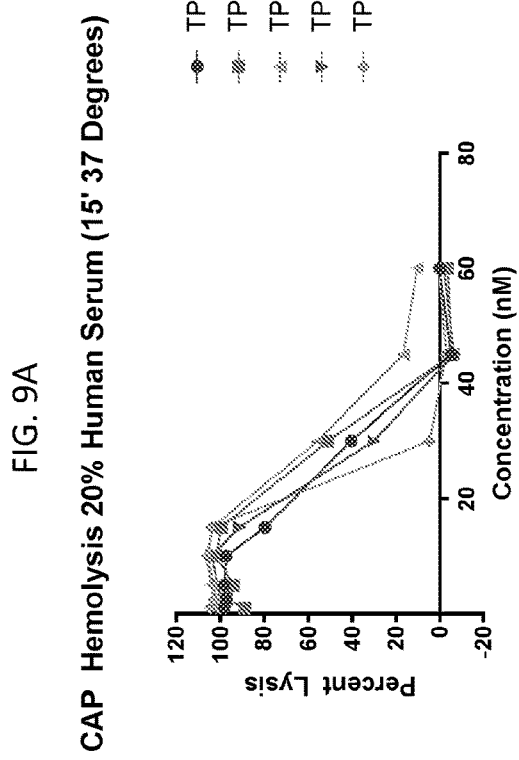
Figure 10A:
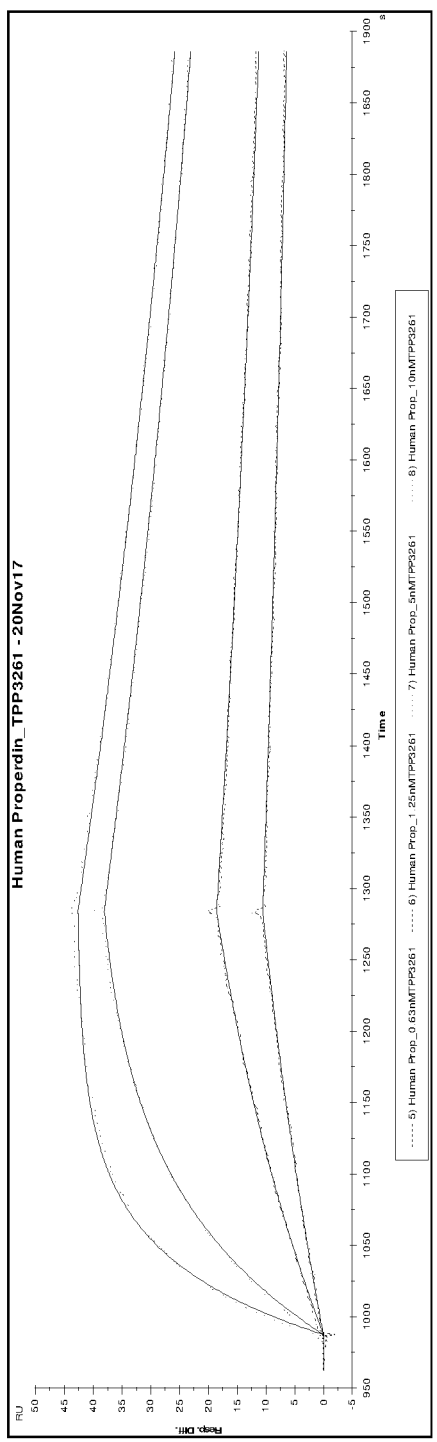
FIG. 10A and FIG. 10B show the binding affinity of selected anti-properdin bispecific antibodies to biotinylated properdin using a properdin capture method.
Figure 10B:
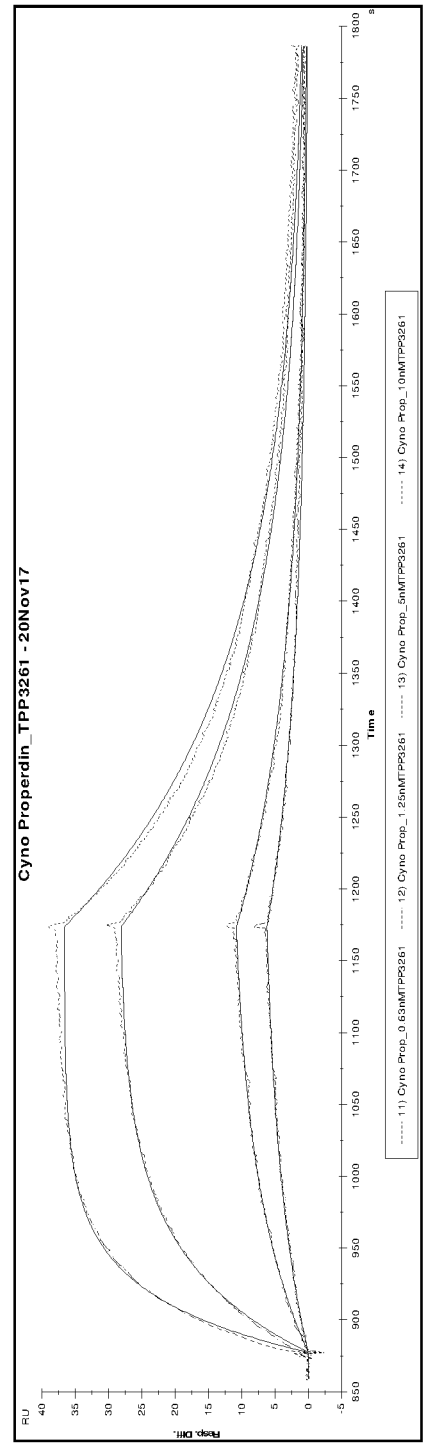
Figure 11A:
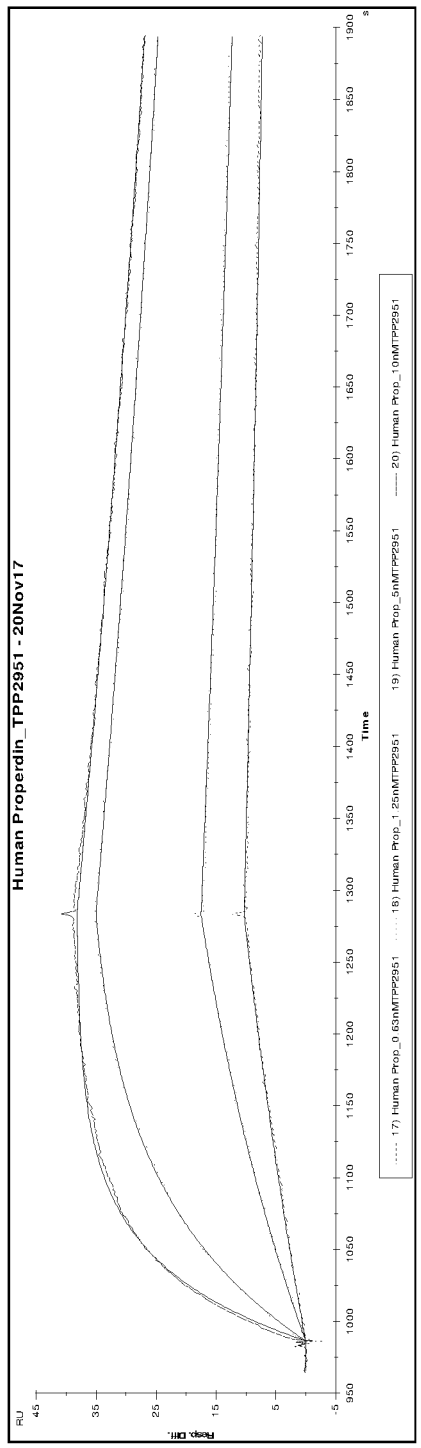
FIG. 11A and FIG. 11B show the binding affinity of selected anti-properdin bispecific antibodies to biotinylated properdin using a properdin capture method.
Figure 11B:
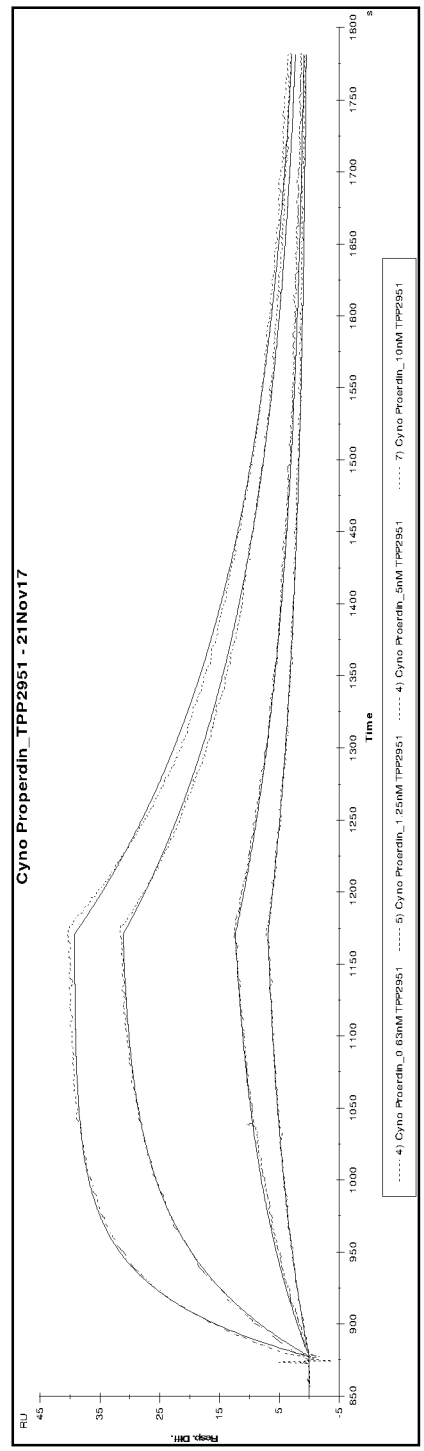
Figure 12A:
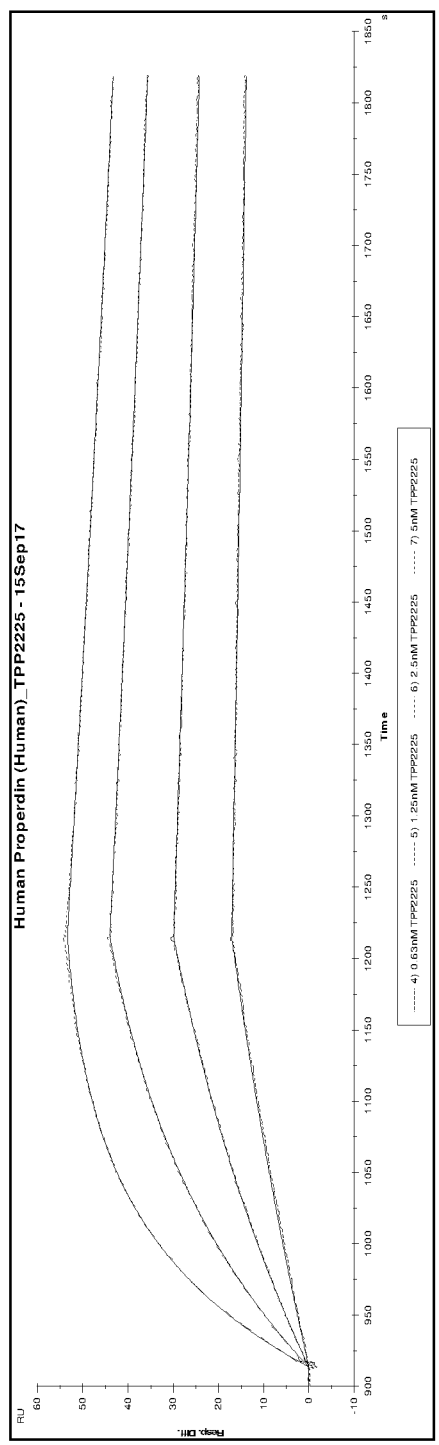
FIG. 12A and FIG. 12B show the binding affinity of selected anti-properdin bispecific antibodies to biotinylated properdin using a properdin capture method.
Figure 12B:
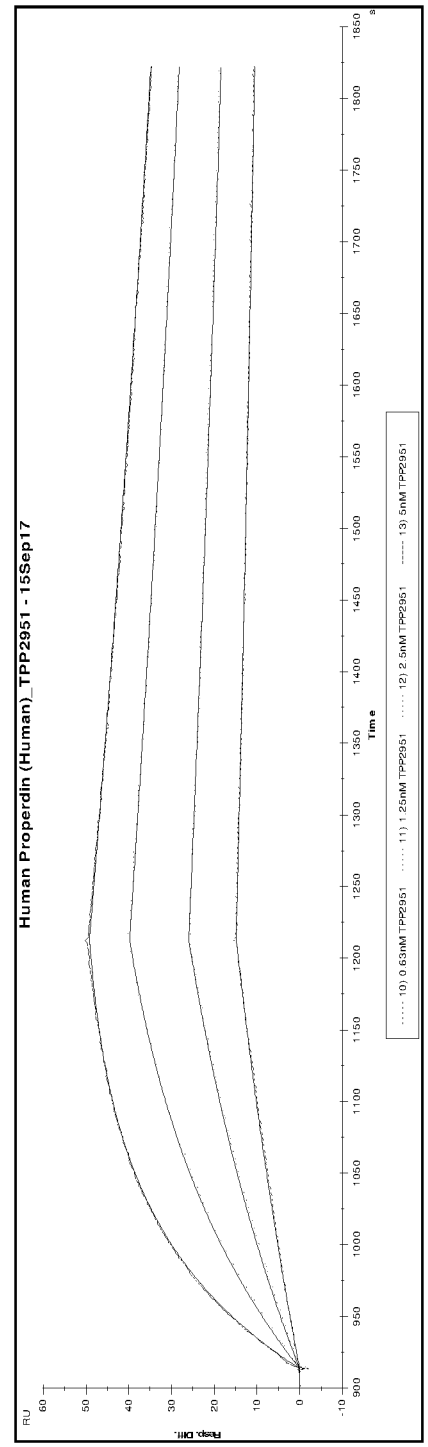

50 μL/well was transferred from the dilution plate to assay plate. The assay plate was left at room temperature while proceeding to the next step. 400 μL of rRBCs were washed 4 times, each with 1 mL of GVB supplemented with 10 mM EGTA and 10 mM MgCl$_2$. rRBCs were spun at 2600 rpm for 1 minute after each wash. After the final wash, rRBCs were resuspend to a volume of 400 μL by adding 300 μL GVB supplemented with 10 mM EGTA and 10 mM MgCl$_2$. 50 μL of washed rRBCs were resuspended to 1 mL with GVB supplemented with 10 mM EGTA and 10 mM MgCl$_2$. 30 μL of this dilute solution was added to 100 μL of the prepared sample in the assay plate, yielding 1.5×10$^6$ cells/well. The plate was incubated for 30 minutes at 37° C. The plate was then centrifuged at 1000×g for 5 min and 85 μL of the supernatant was transferred to a flat bottom 96 well plate. Hemolysis was determined by measuring OD at 415 nm. A progressive decrease in light scatter (due to the lysis of intact cells) was measured at 415 nm as a function of concentration. For the calculation, the total inhibition was calculated at each concentration of the anti-properdin antibody construct and the results were expressed as a percentage of unlisted controls. FIG. 8A-FIG. 8B show hemolysis mediated by TPP-2221, TP-2222, TPP-2223, TP-2224, and TP-2225 in human (FIG. 8A) and cynomolgus (FIG. 8B) serum. The control antibody is an anti-properdin antibody. FIG. 9A-FIG. 9B show hemolysis mediated by TPP-2225, TPP-2951, TPP-3261, TPP-3071, and TPP-3072 in human (FIG. 9A) and cynomolgus (FIG. 9B) serum.

FIG. 10A-FIG. 10B, FIG. 11A-FIG. 11B, and FIG. 12A-FIG. 12B show the binding kinetics of TPP-3261, TPP-2951, and TPP-2225 to human and cynomolgus properdin.

The binding affinities and IC50 values are shown for each construct in the following Tables 5-9.

TABLE 5

Binding kinetics of bispecific constructs

| Molecule | IC50 (nM) | Description |
|---|---|---|
| Anti-properdin control | 14.6-15.4 | Anti-properdin |
| TPP-2221 | 7.1-8.4 | LVP058_hG2-G4 |
| TPP-2222 | 5.1-5.8 | LVP058_hG1_noC1q |
| TPP-2223 | 8.4-13.4 | Anti-properdin hG1_noC1q |
| TPP-2224 | 13.9-15.8 | LVP058-anti-Alb |
| TPP-2225 | 11.6-12.9 | anti-Alb-LVP058 |

TABLE 6

Binding kinetics of bispecific constructs

| Molecule | Affinity pH 7.4 (nM) | Human IC50 (nM) | Cynomolgus IC50 (nM) | Description |
|---|---|---|---|---|
| TPP-2225 | 1.72E-10 | 20.04 to 64.49 | 11.19 to 12.3 | Non-humanized (G4S)3 Linker |
| TPP-2951 | 3.01E-10 | — | 13.76 to 15.89 | Humanized (7 back mutations) |
| TPP-3261 | 4.85E-10 | 28.82 to 30.96 | 14.8 to 23.83 | Humanized (3 back mutations) |
| TPP-3071 | — | 22.28 to 29.36 | 10.66 to 14.58 | Non-humanized (G4D)2 G4 Linker |
| TPP-3072 | — | — | 13.06 to 18.65 | Non-humanized (G4E)2 G4 Linker |

TABLE 7

Binding kinetics of bispecific constructs

| Molecule | Human Properdin | | Cynomolgus Properdin | | Human Albumin | | Cynomolgus Albumin | |
|---|---|---|---|---|---|---|---|---|
|  | pH 7.4 | pH 6.0 | pH 7.4 | pH 6.0 | pH 7.4 | pH 6.0 | pH 7.4 | pH 6.0 |
| TPP-2225 | 1.72E-10 | 2.571E-9 | 1.979E-9 | No fit | 7.74e-10 | 6.46e-10 | 7.07e-9 | 2.30e-9 |
| TPP-2951 | 3.01E-10 | | 2.33E-9 | | | | | |
| TPP-3261 | 4.85E-10 | | 3.08E-9 | | | | | |

TABLE 8

Binding kinetics of bispecific constructs.

| Molecule | Properdin Type | $k_a$ (1/Ms) | $k_d$ (1/s) | $K_D$ (M) | Chi$^2$ | Comments |
|---|---|---|---|---|---|---|
| TPP3261 | Human | 1.72e6 | 8.34e-4 | 4.85e-10 | 0.07 | Good Fit |
| TPP3261 | Cynomolgus | 1.91e6 | 5.87e-3 | 3.08e-9 | 0.24 | Good Fit |
| TPP2951 | Human | 1.78e6 | 5.74e-4 | 3.22e-10 | 0.06 | Good Fit |
| TPP2951 | Cynomolgus | 1.82e6 | 4.26e-3 | 2.33e-9 | 0.17 | Good Fit |

TABLE 9

Binding kinetics of bispecific constructs.

| Molecule | Properdin Type | $k_a$ (1/Ms) | $k_d$ (1/s) | $K_D$ (M) | Chi$^2$ | Comments |
|---|---|---|---|---|---|---|
| TPP2225 | Human | 2.03e6 | 3.49e-4 | 1.72e-10 | 0.04 | Good Fit |
| TPP2951 | Human | 1.88e6 | 5.67e-4 | 3.01e-10 | 0.05 | Good Fit |

Other Embodiments

All publications, patents, and patent applications mentioned in this specification are herein incorporated by reference to the same extent as if each independent publication or patent application was specifically and individually indicated to be incorporated by reference.

It will be understood that the compositions and methods described herein are capable of further modification(s), and this description is intended to include any variations, uses or adaptations following, in general, the principles disclosed herein—including such departures from the present disclosure that come within known or customary practice within the art that may be applied to the essential features hereinbefore set forth, and follows in the scope of the claims.

The invention claimed is:

1. An isolated monovalent antibody or antibody fragment thereof, wherein the antibody or antibody fragment thereof binds human properdin, wherein the antibody or antibody fragment thereof comprises 3 CDRs with the following sequences:

```
a) a CDR-H1 comprising the amino acid sequence
                                      (SEQ ID NO: 16)
   GRISSIIHMA;

b) a CDR-H2 comprising the amino acid sequence
                                      (SEQ ID NO: 12)
   RVGTTVYADSVKG;
   and c) a CDR-H3 comprising the amino acid sequence
                                      (SEQ ID NO: 17)
   LQYEKHGGADY.
```

2. A pharmaceutical composition comprising the isolated monovalent antibody or antibody fragment thereof of claim 1, as an active ingredient, and a pharmaceutically acceptable carrier.

3. The antibody or fragment thereof of claim 1, wherein the antibody or antibody fragment thereof is linked to a second monovalent antibody or antibody fragment thereof by a poly-glycine linker, wherein the poly-glycine linker comprises a GGGGE (SEQ ID NO: 64) sequence.

4. The antibody or fragment thereof of claim 3, wherein the second monovalent antibody or fragment thereof specifically binds albumin.

5. The antibody or fragment thereof of claim 4, wherein the second monovalent antibody or antibody fragment thereof is linked to the N-terminus of the antibody or antibody fragment thereof that binds human properdin.

6. An antibody construct that specifically binds human properdin and albumin, wherein the antibody construct comprises six CDR sequences of SEQ ID NO: 51.

7. An isolated antibody construct comprising the sequence:

```
                                              (SEQ ID NO: 51)
EVQLVESGGGLVKPGGSLRLSCAASGRPVSNYAAAWFRQAPGKEREFVSA

INWQKTATYADSVKGRFTISRDNAKNSLYLQMNSLRAEDTAVYYCAAVFR

VVAPKTQYDYDYWGQGTLVTVSSGGGGEGGGGEGGGGEVQLLESGGGLVQ

PGGSLRLSCAASGRISSIIHMAWFRQAPGKERELVSEISRVGTTVYADSV

KGRFTISRDNSKNTLYLQMNSLKPEDTAVYYCNALQYEKHGGADYWGQGT

LVTVSS.
```

* * * * *